US007503896B2

United States Patent
Miele et al.

(10) Patent No.: US 7,503,896 B2
(45) Date of Patent: Mar. 17, 2009

(54) METHOD AND APPARATUS FOR THE NONINVASIVE ASSESSMENT OF HEMODYNAMIC PARAMETERS INCLUDING BLOOD VESSEL LOCATION

(75) Inventors: Frank R. Miele, San Diego, CA (US); Ronald Mucci, Westwood, MA (US); Gail D. Baura, San Diego, CA (US)

(73) Assignee: Tensys Medical, Inc., San Diego, CA (US)

( * ) Notice: Subject to any disclaimer, the term of this patent is extended or adjusted under 35 U.S.C. 154(b) by 474 days.

(21) Appl. No.: 09/815,982

(22) Filed: Mar. 22, 2001

(65) Prior Publication Data

US 2002/0055680 A1 May 9, 2002

Related U.S. Application Data

(63) Continuation-in-part of application No. 09/342,549, filed on Jun. 29, 1999, now Pat. No. 6,471,655.

(51) Int. Cl.
*A61B 8/00* (2006.01)
(52) U.S. Cl. ................ 600/454; 600/301; 600/485; 600/500
(58) Field of Classification Search ......... 600/437–472, 600/301, 485, 500
See application file for complete search history.

(56) References Cited

U.S. PATENT DOCUMENTS

| 3,527,197 | A | 9/1970 | Ware et al. |
|---|---|---|---|
| 3,601,120 | A | 8/1971 | Massie et al. |
| 3,617,993 | A | 11/1971 | Massie et al. |
| 3,663,932 | A | 5/1972 | Mount et al. |
| 3,791,378 | A | 2/1974 | Hochbert et al. |
| 3,885,551 | A | 5/1975 | Massie |
| 4,109,647 | A | 8/1978 | Stern et al. |

(Continued)

FOREIGN PATENT DOCUMENTS

DE 4218319 A1 6/1992

(Continued)

OTHER PUBLICATIONS

Drzewiecki, G. (1995) "Noninvasive Assessment of Arterial Blood Pressure and Mechanics," The Biomedical Engineering Hanbook CRC Press, Boca Raton, FL, pp. 1196-1211.

(Continued)

*Primary Examiner*—Ruth S Smith
*Assistant Examiner*—Jonathan G Cwern
(74) *Attorney, Agent, or Firm*—Gazdzinski & Associates, PC

(57) ABSTRACT

A method and apparatus for determining the mean arterial blood pressure (MAP) of a subject during tonometric conditions. In one embodiment, the apparatus comprises one or more pressure and ultrasound transducers placed over the radial artery of a human subject's wrist, the latter transmitting and receiving acoustic energy so as to permit the measurement of blood velocity during periods of variable compression of the artery. In another aspect of the invention, a wrist brace useful for measuring blood pressure using the aforementioned apparatus is disclosed. In yet another aspect of the invention, backscattered acoustic energy is used to identify the location of the blood vessel of interest, and optionally control the position of measurement or treatment equipment with respect thereto.

32 Claims, 48 Drawing Sheets

U.S. PATENT DOCUMENTS

| | | | |
|---|---|---|---|
| 4,127,114 A | | 11/1978 | Bretscher |
| 4,154,231 A | | 5/1979 | Russell |
| 4,239,047 A | | 12/1980 | Griggs, III et al. |
| 4,249,540 A | | 2/1981 | Koyama et al. |
| 4,269,193 A | * | 5/1981 | Eckerle ................ 600/485 |
| 4,318,413 A | * | 3/1982 | Iinuma et al. ............. 600/441 |
| 4,349,034 A | | 9/1982 | Ramsey, III |
| 4,476,875 A | | 10/1984 | Nilsson et al. |
| 4,566,462 A | | 1/1986 | Janssen |
| 4,584,880 A | * | 4/1986 | Matzuk ................ 73/609 |
| 4,590,948 A | | 5/1986 | Nilsson |
| 4,596,254 A | | 6/1986 | Adrian et al. |
| 4,630,612 A | * | 12/1986 | Uchida et al. ............. 600/441 |
| 4,651,747 A | | 3/1987 | Link |
| 4,660,564 A | | 4/1987 | Benthin et al. |
| 4,719,923 A | | 1/1988 | Hartwell et al. |
| 4,721,113 A | * | 1/1988 | Stewart et al. ............. 600/449 |
| 4,733,668 A | * | 3/1988 | Torrence ................ 600/437 |
| 4,754,761 A | | 7/1988 | Ramsey, III et al. |
| 4,771,792 A | | 9/1988 | Seale |
| 4,802,488 A | * | 2/1989 | Eckerle ................ 600/485 |
| 4,867,170 A | | 9/1989 | Takahashi |
| 4,869,261 A | | 9/1989 | Penaz |
| 4,901,733 A | | 2/1990 | Kaida et al. |
| 4,924,871 A | | 5/1990 | Honeyager |
| 4,960,128 A | | 10/1990 | Gordon et al. |
| 5,030,956 A | | 7/1991 | Murphy |
| 5,065,765 A | * | 11/1991 | Eckerle et al. ............. 600/485 |
| 5,072,733 A | | 12/1991 | Spector et al. |
| 5,094,244 A | | 3/1992 | Callahan et al. |
| 5,119,822 A | | 6/1992 | Niwa |
| 5,158,091 A | | 10/1992 | Butterfield et al. |
| 5,163,438 A | | 11/1992 | Gordon et al. |
| 5,170,796 A | | 12/1992 | Kobayashi |
| 5,238,000 A | | 8/1993 | Niwa |
| 5,240,007 A | | 8/1993 | Pytel et al. |
| 5,241,964 A | | 9/1993 | McQuilkin |
| 5,261,412 A | | 11/1993 | Butterfield et al. |
| 5,273,046 A | | 12/1993 | Butterfield et al. |
| 5,280,787 A | * | 1/1994 | Wilson et al. ............. 600/456 |
| 5,289,823 A | * | 3/1994 | Eckerle ................ 600/492 |
| 5,327,893 A | | 7/1994 | Savic |
| 5,363,849 A | * | 11/1994 | Suorsa et al. ............. 600/454 |
| 5,368,039 A | | 11/1994 | Moses |
| 5,409,010 A | | 4/1995 | Beach et al. |
| 5,439,001 A | | 8/1995 | Butterfield et al. |
| 5,450,852 A | | 9/1995 | Archibald et al. |
| 5,467,771 A | | 11/1995 | Narimatsu et al. |
| 5,479,928 A | | 1/1996 | Cathignol et al. |
| 5,494,043 A | | 2/1996 | O'Sullivan et al. |
| 5,495,852 A | | 3/1996 | Stadler et al. |
| 5,551,434 A | | 9/1996 | Iinuma |
| 5,590,649 A | | 1/1997 | Caro et al. |
| 5,617,867 A | | 4/1997 | Butterfield et al. |
| 5,634,467 A | | 6/1997 | Nevo |
| 5,640,964 A | | 6/1997 | Archibald et al. |
| 5,642,733 A | | 7/1997 | Archibald et al. |
| 5,649,542 A | | 7/1997 | Archibald et al. |
| 5,669,388 A | * | 9/1997 | Vilkomerson ............. 600/455 |
| 5,701,898 A | * | 12/1997 | Adam et al. ............. 600/454 |
| 5,718,229 A | * | 2/1998 | Pesque et al. ............. 600/441 |
| 5,720,292 A | | 2/1998 | Poliac |
| 5,722,414 A | | 3/1998 | Archibald et al. |
| 5,738,103 A | | 4/1998 | Poliac |
| 5,749,364 A | | 5/1998 | Sliwa et al. |
| 5,785,654 A | | 7/1998 | Iinuma et al. |
| 5,797,850 A | | 8/1998 | Archibald et al. |
| 5,832,924 A | | 11/1998 | Archibald et al. |
| 5,833,618 A | | 11/1998 | Caro et al. |
| 5,848,970 A | | 12/1998 | Voss et al. |
| 5,855,557 A | | 1/1999 | Lazenby |
| 5,876,346 A | | 3/1999 | Corso |
| 5,895,359 A | | 4/1999 | Peel, III |
| 5,904,654 A | | 5/1999 | Wohltmann et al. |
| 5,908,027 A | | 6/1999 | Butterfield et al. |
| 5,916,180 A | | 6/1999 | Cundari et al. |
| 5,938,618 A | | 8/1999 | Archibald et al. |
| 5,941,828 A | | 8/1999 | Archibald et al. |
| 5,964,711 A | | 10/1999 | Voss et al. |
| 5,993,394 A | | 11/1999 | Poliac |
| 6,017,314 A | | 1/2000 | Poliac |
| 6,027,452 A | | 2/2000 | Flaherty et al. |
| 6,099,477 A | | 8/2000 | Archibald et al. |
| 6,132,382 A | | 10/2000 | Archibald et al. |
| 6,159,157 A | | 12/2000 | Archibald et al. |
| 6,176,831 B1 | * | 1/2001 | Voss et al. ................ 600/485 |
| 6,228,034 B1 | * | 5/2001 | Voss et al. ................ 600/485 |
| 6,241,679 B1 | | 6/2001 | Curran |
| 6,245,022 B1 | | 6/2001 | Archibald et al. |
| 6,258,031 B1 | | 7/2001 | Sunagawa et al. |
| 6,267,728 B1 | | 7/2001 | Hayden |
| 6,340,349 B1 | | 1/2002 | Archibald et al. |
| D458,375 S | | 6/2002 | Thede |
| 6,443,905 B1 | * | 9/2002 | Nissila et al. ............. 600/490 |
| 6,447,456 B1 | * | 9/2002 | Tsubata ................ 600/455 |
| 6,471,646 B1 | | 10/2002 | Thede |
| 6,471,655 B1 | | 10/2002 | Baura |
| 6,514,211 B1 | | 2/2003 | Baura |
| 6,554,774 B1 | * | 4/2003 | Miele ................ 600/485 |
| 6,558,335 B1 | | 5/2003 | Thede |
| 6,589,185 B1 | | 7/2003 | Archibald et al. |
| 6,676,600 B1 | * | 1/2004 | Conero et al. ............. 600/438 |

FOREIGN PATENT DOCUMENTS

| | | |
|---|---|---|
| EP | 284 095 B1 | 3/1988 |
| EP | 0 342 249 A1 | 5/1988 |
| EP | 0299 827 A1 | 6/1988 |
| EP | 0595 666 B1 | 9/1993 |
| EP | 0 603 666 A2 | 12/1993 |
| EP | 0818 176 A1 | 7/1996 |
| WO | WO 84 00290 | 2/1984 |
| WO | WO 92 07508 | 5/1992 |
| WO | WO 95/00074 | 1/1995 |
| WO | WO 95 13014 | 5/1995 |
| WO | WO 98 25511 A | 6/1998 |

OTHER PUBLICATIONS

Boashash, B., et al. (1987) "An Efficient Real-Time Implementation of the Wigner-Ville Distribution," IEEE Trans ASSP 35:1611-1618.

Drzewiecki, G.M., et al. (1985) Generalization of the Transmural Pressure-Area Relation for the F emoral Artery, 7$^{th}$ Annual IEEE EMBS Conference 507.

Hoeks, A.P.G., et al. (1985) Transcutaneous Detection of Relative Changes in Artery Diameter, Ultrasound in Med and Bio 11:51-59.

Carson, E.R., et al. (1983) "The Mathematical Modeling of Metabolic and Endocrine Systems: Model Formulation, Identification, and Validation," John Wiley & Sons, NY, pp. 185-189.

Anderson, E.A., et al (1989) "Flow-Mediated and Reflex Changes in Large Peripheral Artery Tone in Humans," Circulation 79:93-100.

Hartley, C.J., et al. (1991) "An Ultrasonic Method for Measuring Tissue Displacement: Technical Details and Validation for Measuring Myocardial Thickening," IEEE Trans Biomed, 38:735-747.

Cariou, Alain, et al. (1998) "Noninvasive Cardiac Output Monitoring by Aortic Blood Flow Determination: Evaluation of the Sometec Cynemo-3000 System," Critical Care Medicine, vol. 26, No. 12, pp. 2066-2072.

Advertisement for HemoSonic™ 100 by Arrow International—licensed under U.S. Patent 5,479,928 listed above.

U.S. Appl. No. 09/815,080 entitled "Method and Apparatus For Assessing Hemodynamic Parameters within the Circulatory System of a Living Subject," filed Mar. 22, 2001.

\* cited by examiner (PART 1 OF 3)

(PART 2 OF 3)

(PART 3 OF 3)

| |
|---|
| -1 |
| -1 |
| 0 |
| 2 |
| 4 |
| 6 |
| 6 |
| 2 |
| -6 |
| -16 |
| -25 |
| -26 |
| -16 |
| 10 |
| 50 |
| 98 |
| 143 |
| 176 |
| 188 |
| 176 |
| 143 |
| 98 |
| 50 |
| 10 |
| -16 |
| -26 |
| -25 |
| -16 |
| -6 |
| 6 |
| 6 |
| 6 |
| 4 |
| 2 |
| 0 |
| -1 |
| -1 |

FIG. 26

METHOD AND APPARATUS FOR THE NONINVASIVE ASSESSMENT OF HEMODYNAMIC PARAMETERS INCLUDING BLOOD VESSEL LOCATION

This application is a continuation-in-part of U.S. application Ser. No. 09/342,549, now U.S. Pat. No. 6,471,655 entitled "Method And Apparatus For The Noninvasive Determination Of Arterial Blood Pressure" filed Jun. 29, 1999, and assigned to the Applicant herein.

RELATED APPLICATIONS

This application is related to U.S. Pat. No. 6,514,211 entitled "Method And Apparatus For The Noninvasive Determination Of Arterial Blood Pressure" filed Jan. 21, 2001, and U.S. Pat. No. 7,048,691 entitled "Method and Apparatus for Assessing Hemodynamic Parameters within the Circulatory System of a Living Subject" filed contemporaneously herewith, both assigned to the Assignee hereof.

BACKGROUND OF THE INVENTION

1. Field of the Invention

This invention relates generally to methods and apparatus for monitoring the hemodynamic parameters of a living subject, and specifically to the non-invasive monitoring of arterial blood pressure using acoustic techniques.

2. Description of the Related Art

Three well known techniques have been used to non-invasively monitor a subject's arterial blood pressure waveform, namely, auscultation, oscillometry, and tonometry. Both the auscultation and oscillometry techniques use a standard inflatable arm cuff that occludes the subject's brachial artery. The auscultatory technique determines the subject's systolic and diastolic pressures by monitoring certain Korotkoff sounds that occur as the cuff is slowly deflated. The oscillometric technique, on the other hand, determines these pressures, as well as the subject's mean pressure, by measuring actual pressure changes that occur in the cuff as the cuff is deflated. Both techniques determine pressure values only intermittently, because of the need to alternately inflate and deflate the cuff, and they cannot replicate the subject's actual blood pressure waveform. Thus, true continuous, beat-to-beat blood pressure monitoring cannot be achieved using these techniques.

Occlusive cuff instruments of the kind described briefly above generally have been effective in sensing long-term trends in a subject's blood pressure. However, such instruments generally have been ineffective in sensing short-term blood pressure variations, which are of critical importance in many medical applications, including surgery.

The technique of arterial tonometry is also well known in the medical arts. According to the theory of arterial tonometry, the pressure in a superficial artery with sufficient bony support, such as the radial artery, may be accurately recorded during an applanation sweep when the transmural pressure equals zero. The term "applanation" refers to the process of varying the pressure applied to the artery. An applanation sweep refers to a time period during which pressure over the artery is varied from overcompression to undercompression or vice versa. At the onset of a decreasing applanation sweep, the artery is overcompressed into a "dog bone" shape, so that pressure pulses are not recorded. At the end of the sweep, the artery is undercompressed, so that minimum amplitude pressure pulses are recorded. Within the sweep, it is assumed that an applanation occurs during which the arterial wall tension is parallel to the tonometer surface. Here, the arterial pressure is perpendicular to the surface and is the only stress detected by the tonometer sensor. At this pressure, it is assumed that the maximum peak-to-peak amplitude (the "maximum pulsatile") pressure obtained corresponds to zero transmural pressure. This theory is illustrated graphically in FIG. 1. Note that in FIG. 1, bone or another rigid member is assumed to lie under the artery.

One prior art device for implementing the tonometry technique includes a rigid array of miniature pressure transducers that is applied against the tissue overlying a peripheral artery, e.g., the radial artery. The transducers each directly sense the mechanical forces in the underlying subject tissue, and each is sized to cover only a fraction of the underlying artery. The array is urged against the tissue, to applanate the underlying artery and thereby cause beat-to-beat pressure variations within the artery to be coupled through the tissue to at least some of the transducers. An array of different transducers is used to ensure that at least one transducer is always over the artery, regardless of array position on the subject. This type of tonometer, however, is subject to several drawbacks. First, the array of discrete transducers generally is not anatomically compatible with the continuous contours of the subject's tissue overlying the artery being sensed. This has historically led to inaccuracies in the resulting transducer signals. In addition, in some cases, this incompatibility can cause tissue injury and nerve damage and can restrict blood flow to distal tissue.

Prior art tonometry systems are also quite sensitive to the orientation of the pressure transducer on the subject being monitored. Specifically, such systems show a degradation in accuracy when the angular relationship between the transducer and the artery is varied from an "optimal" incidence angle. This is an important consideration, since no two measurements are likely to have the device placed or maintained at precisely the same angle with respect to the artery.

Perhaps the most significant drawback to arterial tonometry systems in general is their inability to continuously monitor and adjust the level of arterial wall compression to an optimum level of zero transmural pressure. Generally, optimization of arterial wall compression has been achieved only by periodic recalibration. This has required an interruption of the subject monitoring function, which sometimes can occur during critical periods. This disability severely limits acceptance of tonometers in the clinical environment.

It is also noted that the maximum pulsatile theory described above has only been demonstrated to date in excised canine arteries, and not in vivo. See, for example, Drzewiecki, G. M, et al, "Generalization of the transmural pressure-area relation for the femoral artery", $7^{th}$ *Annual IEEE EMBS Conference,* 1985, pp. 507-510. Accordingly, the maximum peak-to-peak amplitude in vivo may not occur at the arterial pressure at which the transmural pressure equals zero. In fact, during anecdotal studies performed by the applicant herein using two prior art tonometry systems (with which several hundred applanation sweeps were recorded under numerous test conditions), the maximum pulsatile theory described above never yielded measured mean arterial pressure (MAP) that was consistently similar to the average of two cuff pressure measurements taken immediately before and after the sweep. These factors suggest that prior art maximum pulsatile theory devices may produce significant errors in measured MAP.

Yet another disability with prior art tonometry systems is the inability to achieve imprecise placement of the tonometric sensors over the artery being measured. Similarly, even if properly placed at the outset of a measurement, the movement of the subject during the measurement process may require that the sensors be repositioned periodically with respect to the artery, a capability that prior art tonometric systems do not possess. Proper sensor placement helps assure that representative data is obtained from the subject during measurement, and that accurate results are obtained.

Based on the foregoing, there is a clear need for an apparatus, and related method, for non-invasively and continually monitoring a subject's arterial blood pressure, with reduced susceptibility to noise and subject movement, and relative insensitivity to placement of the apparatus on the subject. Such an improved apparatus and method would also obviate the need for frequent recalibration of the system while in use on the subject. Furthermore, it would be desirable to make certain components of the apparatus in contact with the subject disposable, thereby allowing for the cost effective replacement of these components at regular intervals.

SUMMARY OF THE INVENTION

The invention disclosed herein addresses the foregoing needs by providing an improved apparatus and method for non-invasively monitoring the arterial blood pressure of a subject.

In a first aspect of the invention, an improved method for measuring the mean arterial blood pressure in a subject is disclosed. In one embodiment, the method comprises placing both a pressure transducer and ultrasonic transducer over an artery of the subject; varying the pressure applied to the artery to compress (applanate) the artery from a state of overcompression to a state of undercompression; measuring the arterial pressure via the aforementioned pressure transducer as a function of time; generating acoustic pulses via the ultrasonic transducer; measuring at least one parameter (such as the blood velocity and time-frequency distribution as a function of time using the frequency shifts produced by the pulses); and correlating the at least one parameter to the mean arterial pressure (MAP).

In a second aspect of the invention, the foregoing acoustic pulses are used to assist in placement of the transducers on the subject's wrist so as to maximize the signal-to-noise ratio associated with the blood pressure measurement. In one embodiment, the amplitude of echoes received by the ultrasonic transducer is measured by an ultrasound receiver circuit as the transducer is moved transversely across the artery of interest; the transducer is positioned using a fuzzy logic control circuit such that the amplitude of the echoes is minimized.

In a third aspect of the invention, an improved tonometric apparatus useful for non-invasively and continuously measuring the mean arterial pressure (MAP) in a subject is disclosed. In one embodiment, the apparatus includes both a pressure transducer and an ultrasonic transducer which, in conjunction with supporting signal processing circuitry, measure both the arterial applanation and arterial blood velocity, respectively. These transducers are mated to the interior surface of the subject's wrist. The transducers and their associated processing circuitry track the blood velocity in the radial artery during applanation sweeps; i.e., the time period beginning when the artery is overcompressed, and ending when the artery is undercompressed, by emitting acoustic pulses and measuring the Doppler shift in the returns or reflections of the acoustic energy from cells present in the blood. The time-frequency distribution is determined from the velocity data, as calculated by an algorithm running on a digital signal processor (DSP). The time at which the time-frequency distribution is maximized corresponds to the time at which the transmural pressure equals zero, and the mean pressure read by the pressure transducer equals the MAP. The measurements of applanation and blood velocity using the apparatus are largely unaffected by the orientation of the transducers on the subject's wrist.

In a fourth aspect of the invention, an improved applanation and transverse positioning motor assembly is disclosed for use with the above described tonometric apparatus. In one embodiment, the assembly includes a first motor for applanation (compression) of the artery in response to fuzzy logic signals from a control circuit, as well as a second motor operatively connected to an ultrasonic receiver (and associated fuzzy logic control circuit) for transverse positioning of the transducer(s) over the artery. The motor assembly is coupled to the transducers and rigidly received within a wrist brace described below such that the applanation motor exerts compressive force against the subject's artery via reaction force against the wrist brace.

In a fifth aspect of the invention, an improved method and apparatus are disclosed for estimating catheter diastolic blood pressure intermittently, and estimating catheter systolic and diastolic pressure continuously. In one embodiment, the method comprises estimating the catheter diastolic blood pressure intermittently; comparing the estimated catheter diastolic pressure to the sensed diastolic pressure to determine a scaling factor; applying the scaling factor to the sensor waveform; and catheter systolic and diastolic blood pressures estimated continuously.

In a sixth aspect of the invention, an improved method for the location of a blood vessel within the tissue of a living subject is disclosed. The method generally comprises generating acoustic energy; transmitting the acoustic energy into the tissue of the subject in the vicinity of a blood vessel; receiving at least a portion of the energy backscattered by the blood vessel; detecting at least one artifact associated with the blood vessel based on the backscattered energy; and determining the location of the blood vessel based at least in part on the detected artifact. In one exemplary embodiment, the blood vessel comprises the radial artery of a human being, and the acoustic energy comprises ultrasonic energy transmitted into the artery via the interior region of the subject's wrist/forearm. Energy backscattered from the artery walls and lumen is received by an ultrasonic transducer and analyzed using an integrated power metric to identify the location of, and/or optimal position of, the transducer with respect to the artery.

In another embodiment, integrated power and/or signal level is analyzed as a function of depth within the tissue to detect the location of the lumen. The location of the artery walls is then determined relative to the lumen, thereby allowing measurement of the diameter of the artery. The position of transducer relative to the artery is adjusted so as to maximize the wall separation (diameter), thereby effectively maintaining the transducer (and any associated applanation device) directly atop the artery. The algorithm may also be adjusted to maintain the transducer in any other desired orientation with respect to the blood vessel; e.g., with a fixed offset, with an offset which varies as a function of the diameter of the blood vessel, etc., or to control the position of the transducer based on other parameters such as signal quality, the presence of cystic components or clutter, and the like.

These and other features of the invention will become apparent from the following description of the invention, taken in conjunction with the accompanying drawings.

BRIEF DESCRIPTION OF THE DRAWINGS

FIG. 3b is a block diagram illustrating a first embodiment of the method of estimating the time-frequency distribution used in conjunction with the method of FIG. 3a.

FIG. 26 is a table listing an exemplary set of (FIR) coefficients used in the quadrature demodulation and filtering method of the present invention.

FIG. 30c is a graphical representation of the normalized integrated power function according to the plateau method of FIG. 30a.

FIG. 30d is a graphical representation of the plateau detection metric used in conjunction with the method of FIG. 30a.

DETAILED DESCRIPTION OF THE INVENTION

Reference is now made to the drawings wherein like numerals refer to like parts throughout.

It is noted that while the invention is described herein in terms of a method and apparatus for monitoring arterial blood pressure suitable for use on the radial artery (i.e., wrist) of a human subject, the invention may also conceivably be embodied or adapted to monitor arterial blood pressure at other locations on the human body, as well as monitoring blood pressure on other warm-blooded species. All such adaptations and alternate embodiments are considered to fall within the scope of the claims appended hereto.

Figure 1:
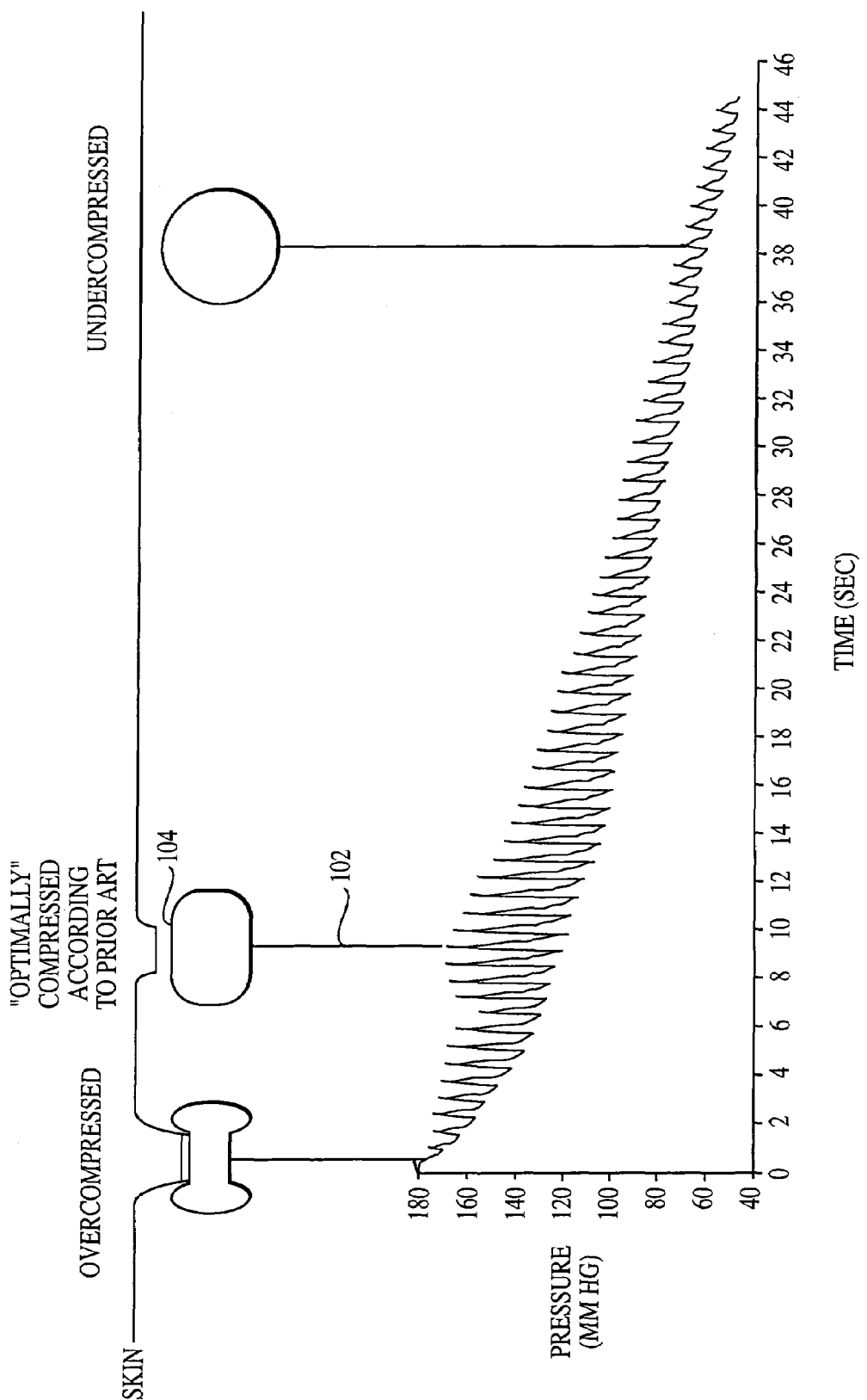
FIG. 1 is a composite graph illustrating the cross-sectional shape of an artery as a function of applied pressure and time, as correlated to blood pressure waveforms, according to prior art arterial tonometry theory.
Figure 2:
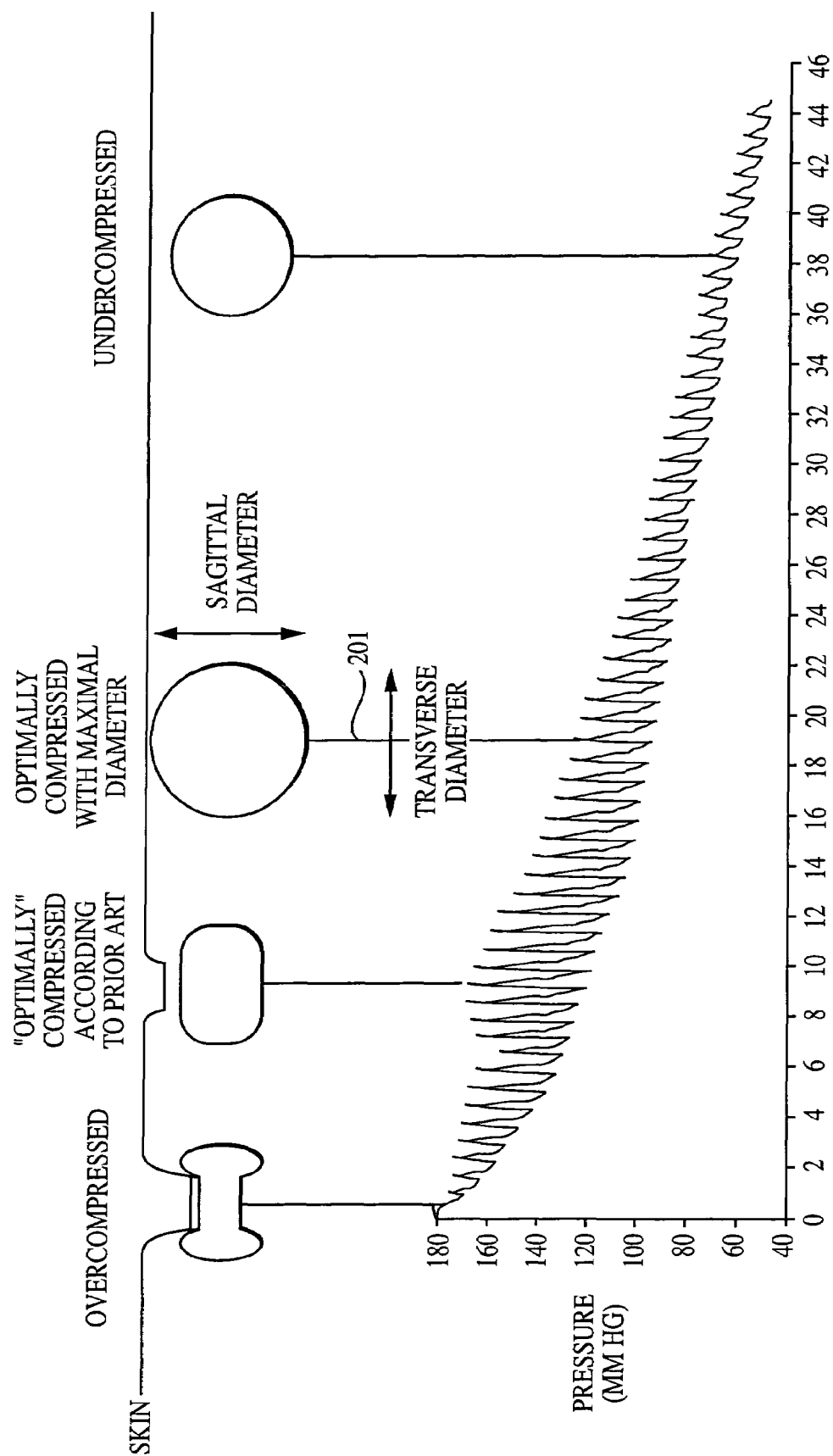
FIG. 2 is a composite graph illustrating the cross-sectional shape of an artery as a function of applied pressure and time, illustrating the hypothesized mechanism behind the maximum time-frequency distribution applanation concept of the present invention.

Referring now to FIGS. 1 and 2, the hypothesized maximum arterial diameter applanation concept of the present invention is described. Under the prior art tonometry theory previously described with respect to FIG. 1, the maximum pulsatile pressure is assumed to correspond to the state of zero transmural pressure; i.e., the point in time 102 when the arterial pressure is perpendicular to the arterial wall surface 104 and is the only pressure detected by the tonometer pressure transducer (not shown). Hence, prior art tonometry systems utilizing this theory measure the maximum peak-to-peak blood pressure within the artery, and correlate this pressure to a state of zero transmural pressure.

In the invention disclosed herein, however, the optimum applanation is found by evaluating one or more other parameters rather than detecting the maximum pulsatile pressure as in the prior art; i.e., in one embodiment, the invention estimates the maximum time-frequency distribution during an applanation sweep. The maximum time-frequency distribution may be indicative of, inter alia, the maximum arterial diameter. As used herein, the term "diameter" includes the actual diameter of a blood vessel measured in a particular dimension or direction and at a particular point in time, as well as any related parameters calculated based on the actual diameter to include, without limitation, mean diameter calculated over a particular time interval, mean diameter as a function of position on the blood vessel, and maximum diastolic diameter (Appendix A). In the maximum time-frequency method of the present invention, it is hypothesized that the optimum applanation occurs at that point in time 201 during the applanation sweep when the external applied pressure has decreased sufficiently so that internal pressure may oppose it, allowing the sagittal arterial diameter to transiently increase to its maximum as a consequence of reactive hyperemia. This phenomenon may occur at the true mean arterial pressure, during which the transmural pressure equals zero, as shown in FIG. 2.

Method of Measuring Mean Arterial Pressure (MAP)

Figure 3A:
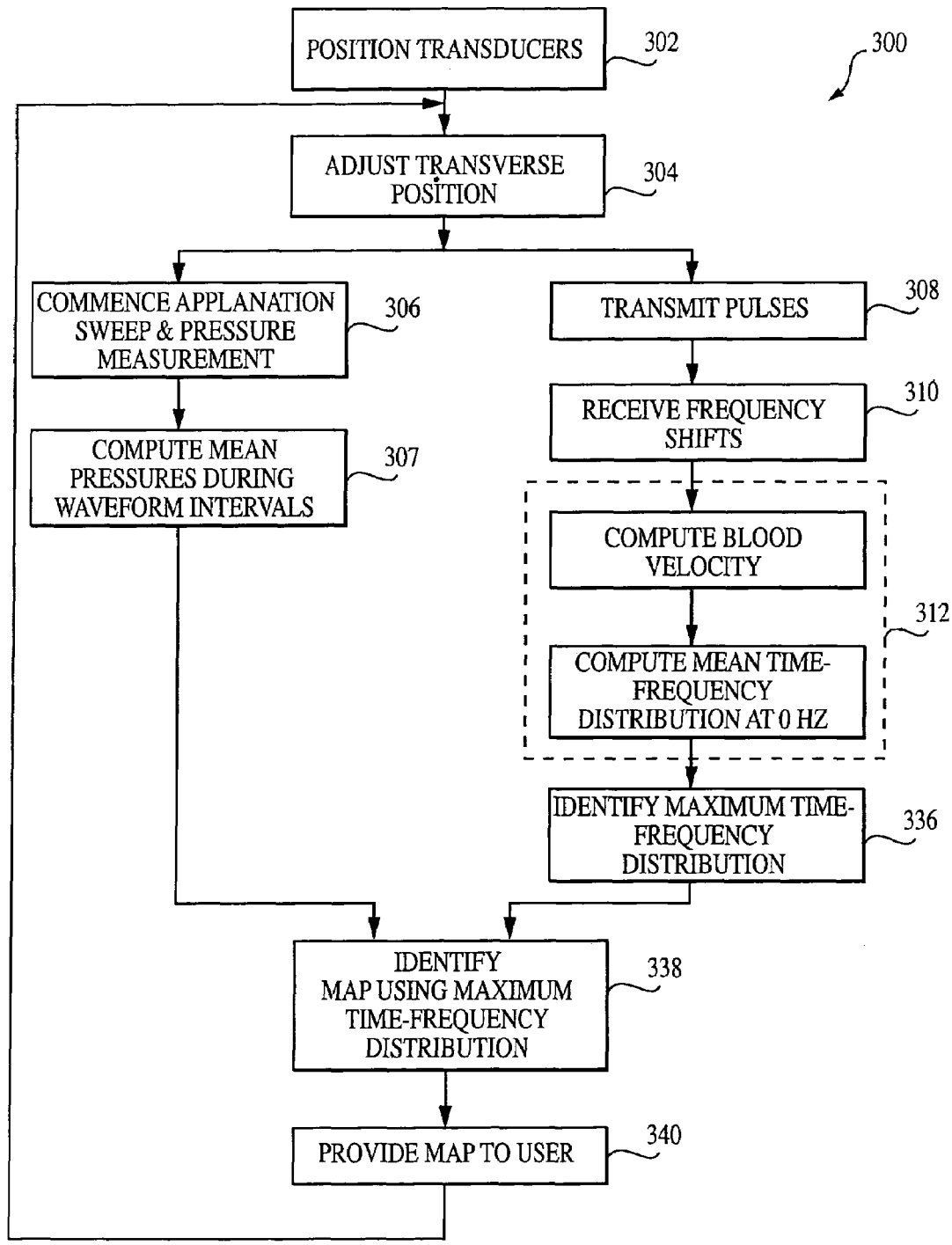
FIG. 3a is a block diagram illustrating one embodiment of the method of measuring arterial blood pressure according to the present invention.

Referring now to FIG. 3a, one embodiment of the maximum time-frequency method of measuring mean arterial pressure according to the present invention is described. In the method 300 of FIG. 3a, pressure and ultrasonic transducers (described in greater detail below with reference to FIGS. 5, 6, and 7) are first positioned generally atop the radial artery of the subject in step 302. As is well known in the medical sciences, the radial artery in the human being runs longitudinally along the inner surface of the wrist and forearm below the surface tissue. Very precise transverse positioning of the ultrasonic and pressure transducers is accomplished in step 304 by generating a series of acoustic pulses, which produce echoes via interaction with tissue and/or red blood cells present in the artery. In one embodiment, the amplitude of these echoes is measured as a function of position, and the transverse position of the transducer element is adjusted so that the amplitude is minimized. At the position overlying the center of the artery, the echoes are mostly absorbed by the blood, as compared to absorption by tissue. Exact positioning over the artery increases the signal-to-noise ratio (SNR) and therefore accuracy of the blood pressure measurement. Other embodiments of locating the blood vessel and positioning the apparatus of the invention with respect thereto are described subsequently herein in greater detail with respect to FIGS. 20-35.

Next, in step 306, a decreasing applanation sweep of the selected artery is commenced. The applanation sweep begins by overcompressing the artery against the underlying bone (or other rigid member) using the aforementioned pressure transducer such that a cross section similar to that shown in FIG. 2 is obtained. As the sweep progresses, the compression of the artery is gradually reduced until the artery is ultimately not compressed at all. During the progression of the applanation sweep, the pressure within the artery during each heartbeat is measured using the pressure transducer, and the mean value of each pressure waveform computed in step 307. Concurrently with the applanation sweep of step 306, acoustic pulses are generated and transmitted into the artery using the ultrasonic transducer in step 308. These pulses are reflected by various structures or entities within the artery (such as the artery walls, and the red blood cells within the subject's blood), and subsequently received as frequency shifts by the ultrasonic transducer in step 310. Next, in step 312, the blood velocity and time-frequency distribution are calculated using the received frequency shifts. Specifically, the frequencies of those echoes reflected by blood cells within the blood flowing in the artery will differ from that of the transmitted acoustic pulses due to the motion of the blood cells. This well-known "Doppler shift" in frequency is used to calculate the blood velocity. Other components of the transmitted pulse are reflected by effectively stationary objects (such as the arterial walls 104); the phase of these echoes is used to calculate the time-frequency distribution. The calculation of the blood velocity and time-frequency distribution are described in greater detail below with respect to FIGS. 3b and 3c. The mean time-frequency distribution at 0 Hz is computed during each heartbeat in step 312. In step 336, the mean time-frequency distribution measurements obtained in step 312 are analyzed to locate the maximum mean time-frequency value occurring during the applanation sweep; the mean arterial pressure corresponding to the maximum time-frequency distribution is then identified in step 338. This mean arterial pressure value is then provided to the user as the MAP in step 340.

Figure 3B:
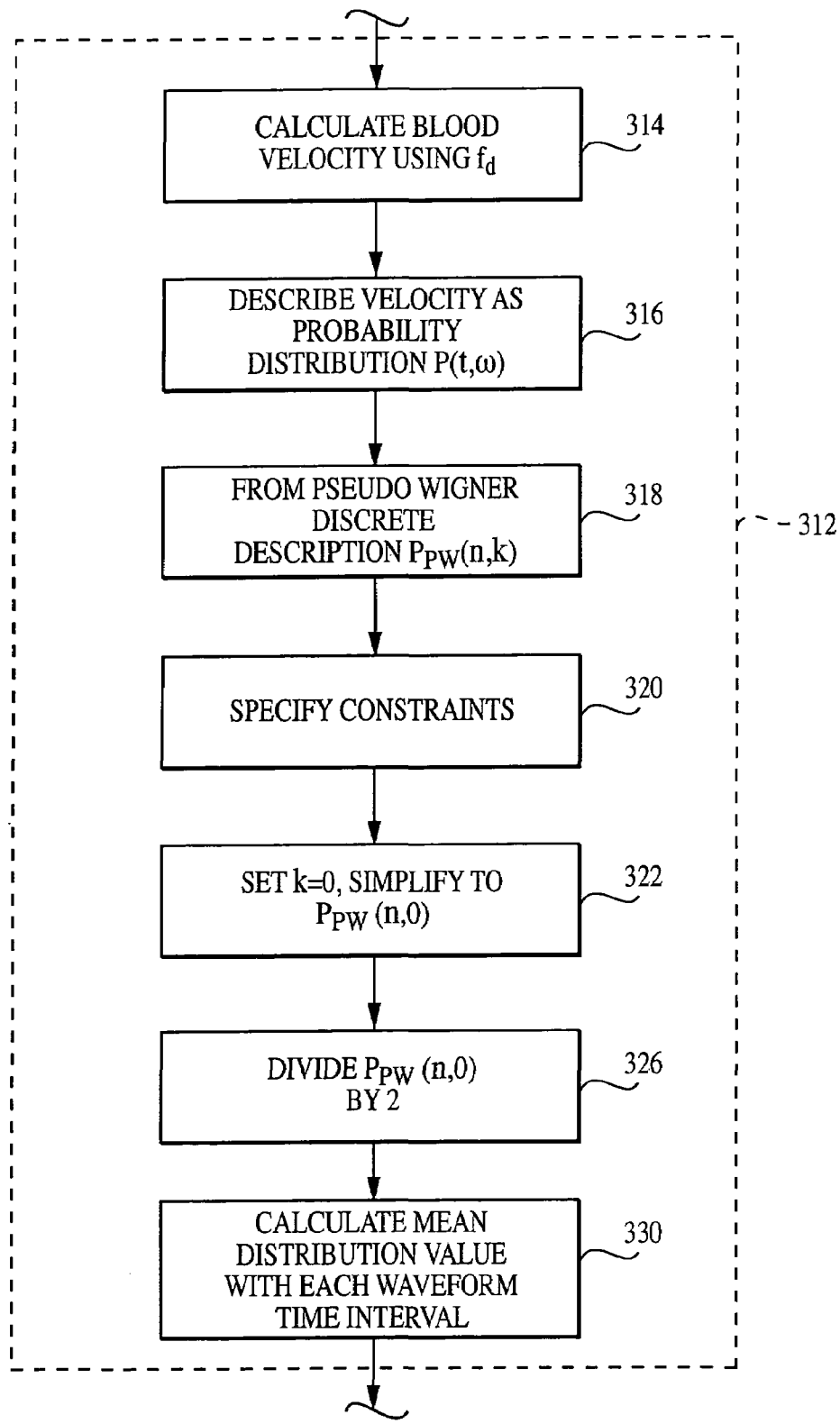

Referring now to FIG. 3b, a first embodiment of the method of determining blood velocity and time-frequency distribution according to the invention is described. As shown in FIG. 3b, the first sub-step 314 of step 312 comprises using the Doppler frequency, $f_d$, and Eqn. 1 to obtain the mean blood velocity, $|\bar{v}|$:

$$|\overline{v}| = \frac{f_d c}{2f_0 \cos\theta},\qquad \text{(Eqn. 1)}$$

where $f_o$ is the transmitted signal frequency, $\theta$ is the transmission angle of the acoustic energy referenced to a vector normal to the longitudinal axis of the artery, and c is the speed of sound in soft tissue.

In the embodiment of FIG. 3b, a time-frequency representation of the type well known in the mathematical arts is calculated for the blood velocity. A time-frequency representation is a two-dimensional mapping of the fraction of the energy of a one-dimensional signal at time, t, and angular frequency, 107. This joint energy density, P(t, ω), is commonly referred to as a "probability distribution" or "distribution", referring to its historical utility in quantum mechanics. This distribution is described in sub-step 316 of FIG. 3 using the form shown in Eqn. 2:

$$P(t, \omega) = \frac{1}{4\pi^2}\int\int \lambda(\theta, \tau) u^*(\theta - 0.5\tau) u(\theta + 0.5\tau) e^{-j\theta t - j\tau\omega} d\theta d\tau, \qquad \text{(Eqn. 2)}$$

where dθ and dτ are dummy integration variables, $\lambda(\theta, \tau)$ is a two-dimensional function known as a "kernel", and u(t) is the input signal. The simplest distribution is the Wigner or Wigner-Ville distribution, which uses a kernel of $\lambda(\theta, \tau)=1$. Note that Eqn. 2 uses continuous time, t, while an actual implementation of the distribution requires discrete time, n. Next, using discrete frequency, k, the discrete time description of the Wigner distribution (also known as a Pseudo Wigner distribution) is formed per sub-step 318 of FIG. 3b, as shown in Eqn. 3.

$$P_{PW}(n, k) = 2\sum_{\tau=-L}^{+L} e^{-j4\pi k\tau/N} u^*(n-\tau) u(n+\tau), \qquad \text{(Eqn. 3)}$$

where $$k = \frac{\omega}{2\pi}, u(t)$$

and its complex conjugate are sample-limited to {−K/2,+K/2}, K is even, and N=K+1. Next, in sub-step 320, a rectangular window is specified, so that L=K/2−|n|. See, e.g., Boashash, B., et al, "An efficient real-time implementation of the Wigner-Ville distribution", *IEEE Trans ASSP,* 35:1611-1618, 1987, which is incorporated herein by reference in its entirety.

In sub-step 322, a frequency of k=0 Hz is selected, and the Pseudo Wigner calculation simplified to the form of Eqn. 4:

$$P_{PW}(n, 0) = 2\sum_{\tau=-L}^{+L} u^*(n-\tau) u(n+\tau). \qquad \text{(Eqn. 4)}$$

Eqn. 4 is equivalent to direct integration of the autocorrelation of a signal, scaled by a factor of 2. Autocorrelation is well known in the signal processing arts. In sub-step 326, Eqn. 4 is divided by a factor of 2. Lastly, in sub-step 330, the mean distribution value is calculated for each heartbeat or pressure waveform time interval.

It is noted that various features in the time-frequency distribution calculated using the method 300 of FIG. 3a can be emphasized by specifying a different kernel. For example, using the kernel $\lambda(\theta, \tau) = e^{-\theta^2 \tau^2 /\sigma}$, where σ is a parameter, to calculate the Choi-Williams distribution, the time-frequency fluctuations within each heartbeat would be reduced. Feature analysis at other frequencies is also possible since similar mean distributions are calculated, but at the expense of more complicated computations. This flexibility in feature selection further enhances the utility of the time-frequency distribution in the present embodiment.

Figure 4A:
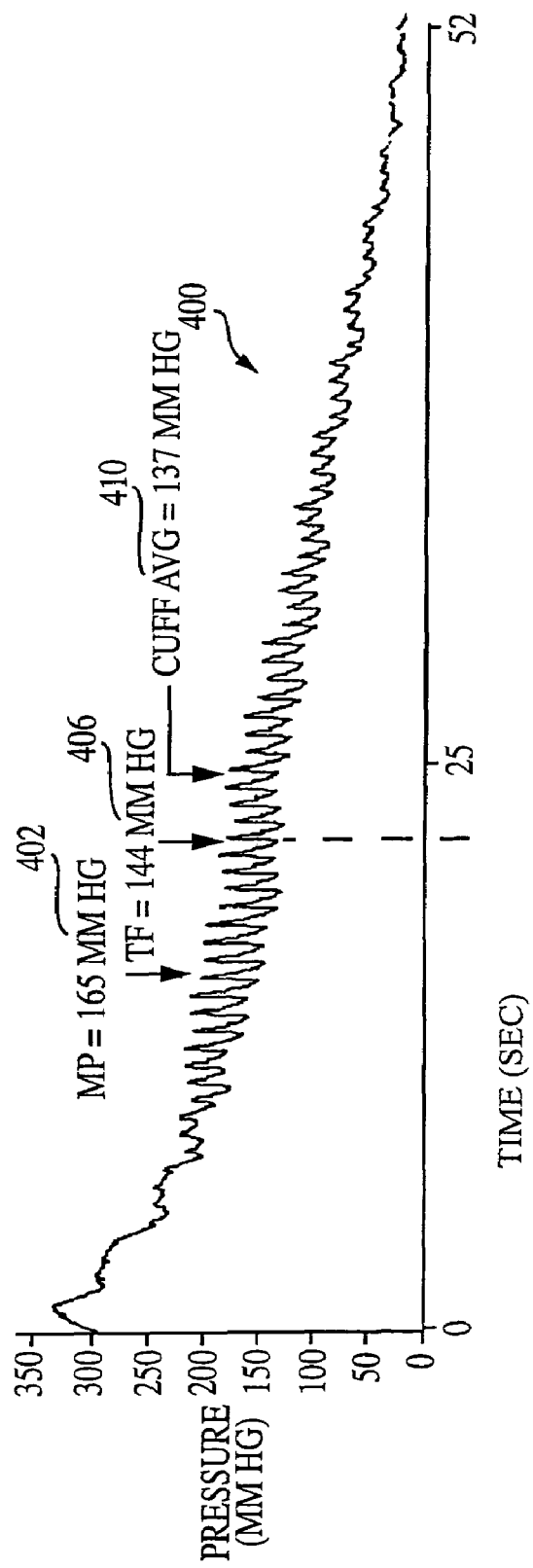
FIGS. 4a-4c are exemplary plots illustrating the relationship between pressure and time, blood velocity and time, and time-frequency distribution and time, respectively, based on typical data obtained using the method of FIGS. 3a-3b.
Figure 4B:
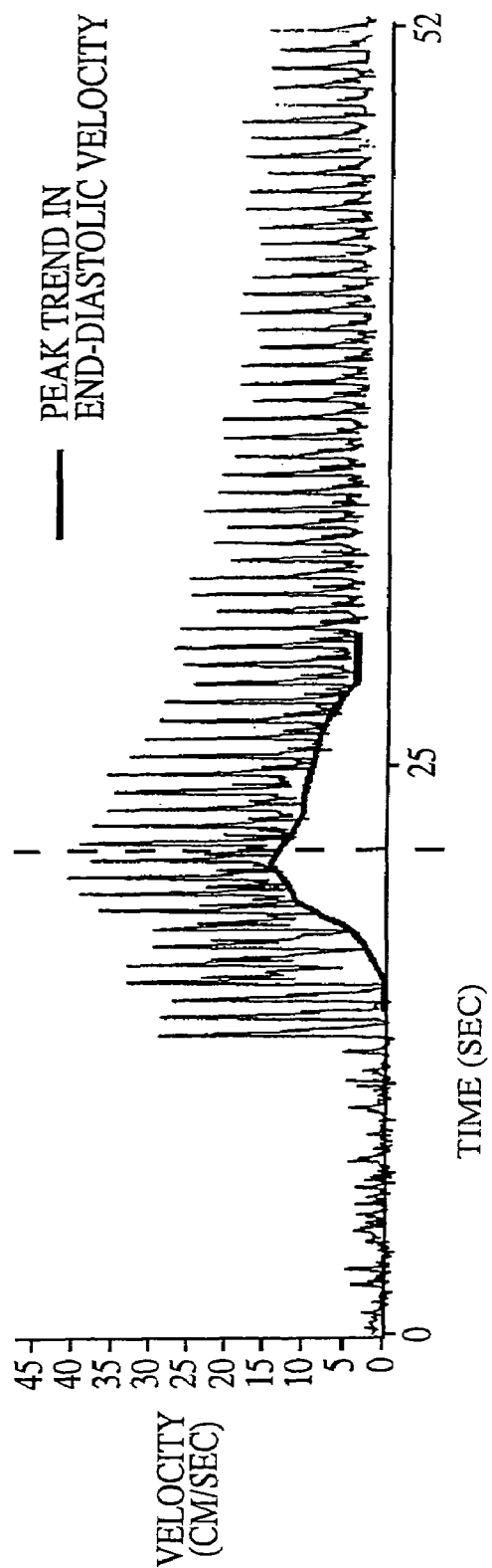
Figure 4C:
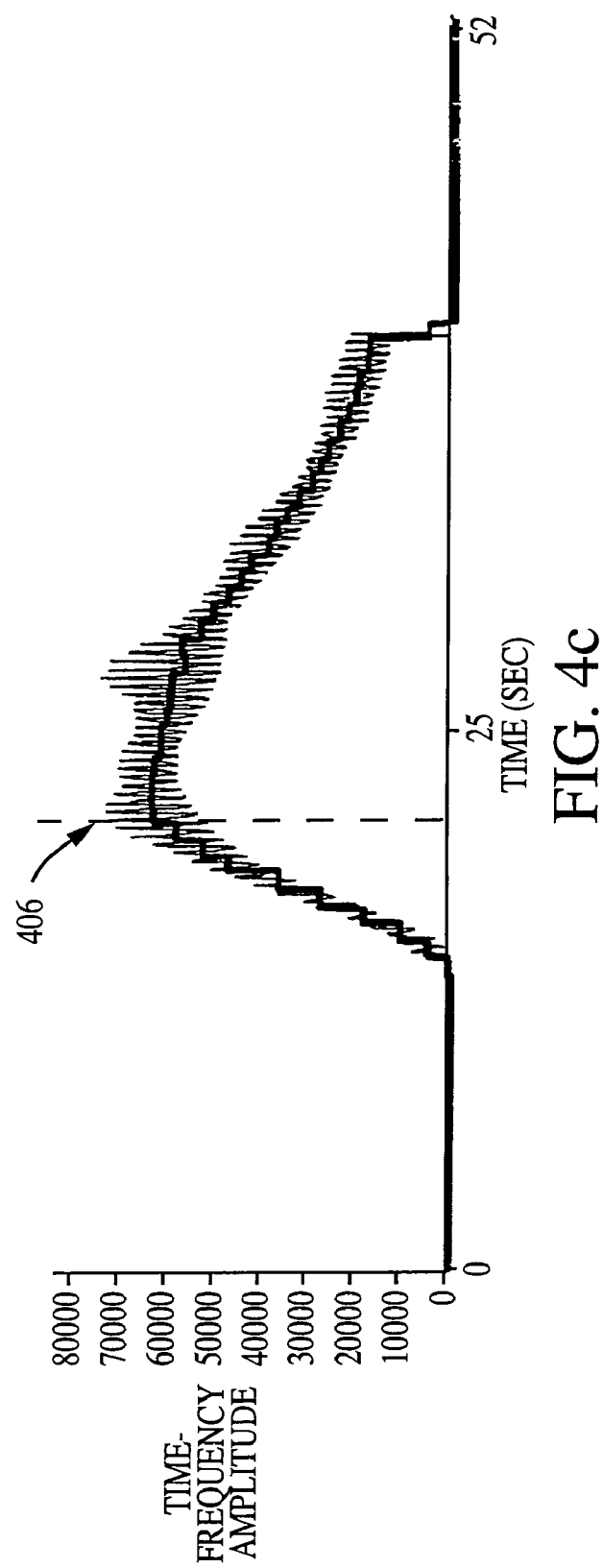

FIGS. 4a-4c are exemplary plots illustrating the relationship between measured radial arterial blood pressure and time (FIG. 4a), radial blood velocity and time (FIG. 4b), and the Pseudo Wigner distribution and time (FIG. 4c), based on typical data obtained using the method of FIG. 3a. The characteristic peak in the Pseudo Wigner distribution results from a large peak trend in the baseline of the blood velocity signal, also known as the end-diastolic velocity (FIG. 4b). In other arteries such as the brachial and femoral arteries, it is known that a similar peak trend in the end-diastolic velocity can be induced after complete arterial occlusion with a cuff for several minutes, followed by complete cuff release. The transient increase in blood flow that follows a brief arterial occlusion is called reactive hyperemia. This transient increase in blood flow and end-diastolic velocity is known to induce a transient increase of 19% in brachial arterial diameter. See, e.g., Anderson, E., et al, "Flow-mediated and reflex changes in large peripheral artery tone in humans", *Circulation,* 79:93-100, 1989, which is incorporated herein by reference in its entirety.

While the radial artery is not compressed by a cuff at the beginning of a decreasing applanation sweep, its flow is completely occluded by the pressure/ultrasound sensor. As the compression decreases during the course of a sweep, reactive hyperemia and its signature peak trend in end-diastolic velocity are induced. The accompanying transient increase in arterial diameter occurs transversely across the artery, but is probably initially prevented sagitally (top to bottom) by the external pressure exerted by the sensor. However, as this external pressure decreases during the sweep to the true mean arterial pressure, the opposing pressure within the artery becomes sufficient that the sagittal arterial diameter may also now increase. The increase in sagital arterial diameter would occur when the transmural pressure equals zero.

The peak in the Pseudo Wigner distribution at a frequency of 0 Hz may indicate when this sudden arterial diameter increase occurs. From Eqn. 1, it is known that the mean blood velocity is proportional to the Doppler shift frequency. The angular frequency of the received wave, $\omega_d$, is found using Eqn. 5:

$$\omega_d = 2\pi f_d. \qquad \text{(Eqn. 5)}$$

The angular frequency $\omega_d$ is integrated; this integration results in the phase of the detected signal echo, φ, as illustrated in Eqn. 6:

$$\phi = \int \omega_d dt. \qquad \text{(Eqn. 6)}$$

As is well known in the art, the low frequencies in the phase echo are proportional to the relative arterial diameter of the artery, d. See, e.g., Hoeks, A. P. G., et al, "Transcutaneous detection of relative changes in artery diameter" *Ultrasound Med & Biol,* 11:51-59, 1985. The phase φ of the detected echo is a function of the time delay between reflection from the near and far arterial walls. Because the time delay depends only on the time difference between reflections from the two arterial walls, the measurement is insensitive to transmission angle. Note that only the relative arterial diameter changes from an initial diameter value during overcompression can be estimated. The relative arterial diameter d is therefore related to the phase using Eqn. 7:

$$d = \frac{\phi c}{4\pi f_o} = \frac{c}{f_o} \int f_d dt = \cos\theta \int |\bar{v}| dt. \quad \text{(Eqn. 7)}$$

Referring back to the Pseudo Wigner distribution calculation at 0 Hz in Eqn. 4, this discrete summation is equivalent to the continuous integral in Eqn 7. As the constant 2 in Eqn. 4 and $\cos\theta$ in Eqn. 7 are only scale factors and $u(n) \equiv |\bar{v}(n)|$, the Pseudo Wigner distribution at 0 Hz is equivalent to the proportional squared relative arterial diameter. Therefore, the peak distribution may occur at the sudden change in sagittal arterial diameter when MAP is reached (FIG. 2). The distribution is smooth, rather than discontinuous at the peak, because the time-frequency distribution acts as a smoothing filter.

Figure 3C:
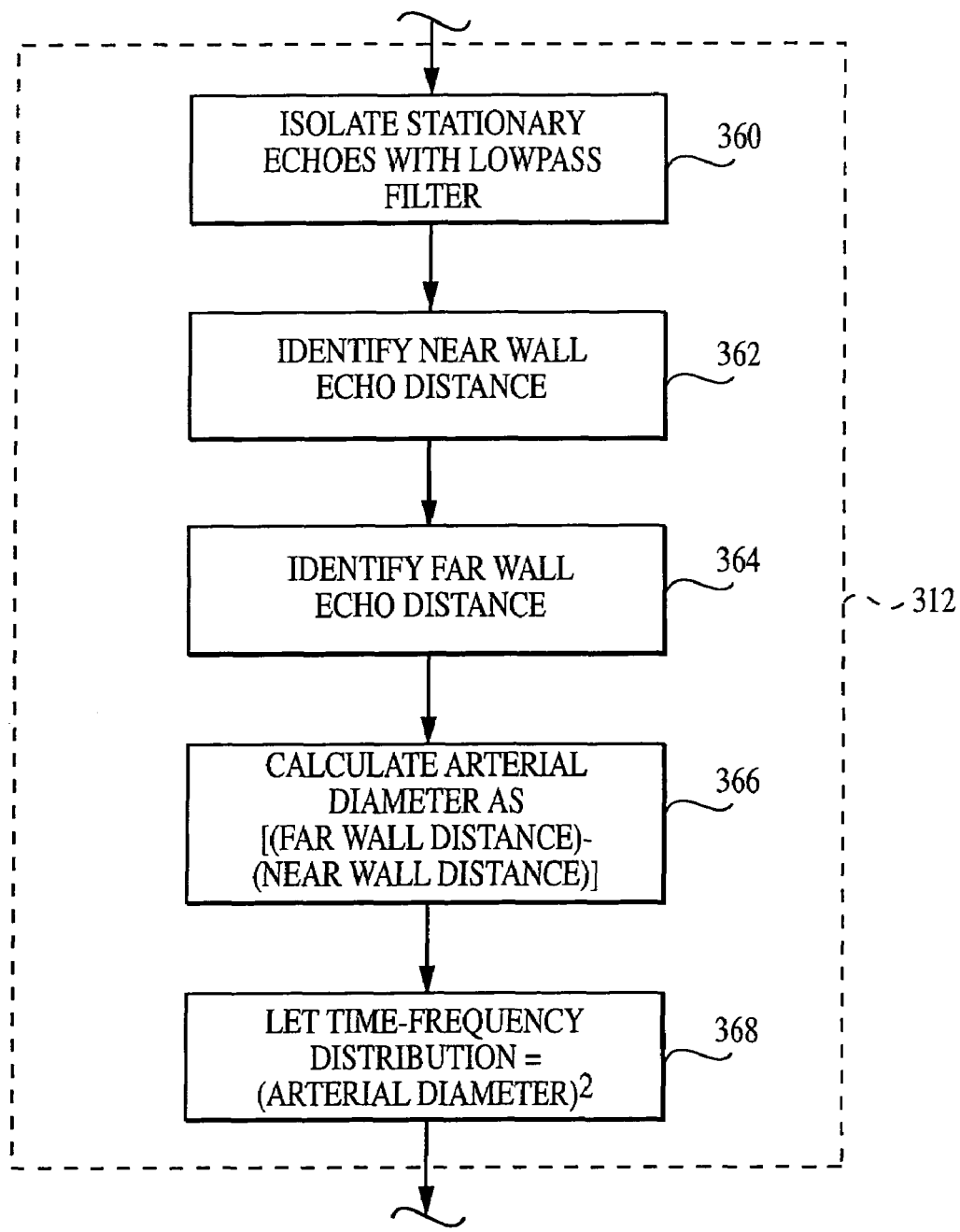
FIG. 3c is a block diagram illustrating a second embodiment of the method of estimating the time-frequency distribution.

Based on this maximum arterial diameter hypothesis, a second embodiment of the method of calculating blood velocity and arterial diameter in conjunction with step 312 of FIG. 3a is now described with respect to FIG. 3c. Rather than calculate the maximum mean time-frequency distribution, diameter changes can be calculated by monitoring the sagittal near and far walls directly. First, stationary echoes are obtained in step 360 using a lowpass filter. The sagittal near and far wall echoes are identified in steps 362 and 364, respectively, and the distance between them is used to calculate the arterial diameter over time in step 366. Finally, in step 368, the time-frequency distribution is equated to the square of the arterial diameter. Note that while this method of calculating the arterial diameter may detect a sudden diametric change more quickly than the time-frequency based method illustrated in FIG. 3b, it is also more complicated because the near and far walls must be continuously detected. See also the discussion of FIGS. 5a and 5b below, which illustrate two exemplary ultrasound filter circuits useful in performing the analysis of FIG. 3c.

It is noted that many variations of the methods described above with reference to FIGS. 3a-3c may be utilized consistent with the invention. Specifically, certain steps are optional and may be performed or deleted as desired. For example, a discrete frequency other than k=0 may be used in step 322. Similarly, other steps (such as additional data sampling or mathematical analysis for example) may be added to the foregoing embodiments. Additionally, the order of performance of certain steps may be permuted, or performed in parallel (or series) if desired. The foregoing methods of FIGS. 3a-3c are therefore merely illustrative of the broader methods of the invention disclosed herein.

The application of the method of FIGS. 3a-3b to typical data is set forth in Appendix A hereto, and illustrated in the exemplary plots of FIGS. 4a-4c. As shown in FIG. 4a, the measured arterial blood pressure 400 generally declines with time, due to reduced applanation of the artery. Note that at some time after beginning the applanation sweep, in this example after approximately 15 seconds, the maximum pulsatile pressure (i.e., the largest peak-to-peak pressure difference) is experienced. At this point, the mean arterial blood pressure (MAP) 402 is approximately 165 mm Hg. At some further time, in this example after approximately 21 seconds, the mean time-frequency distribution (FIG. 4c) is maximized, and the MAP 406 (FIG. 4a) is approximately 144 mm Hg. At a third time, in this example after approximately 24 seconds, the MAP measured during tonometric applanation 410 is closest to the average MAP measured using a prior art oscillometry device, at 137 mm Hg. Hence, based on the data presented in FIG. 4a, prior art maximum pulsatile techniques are substantially less accurate than the "maximum time-frequency" method of the present invention. More significantly, the maximum time-frequency method disclosed herein provides an excellent approximation of the actual mean arterial pressure (as measured by an oscillometry device). Note that noninvasive oscillometry measurement itself possesses an error when compared to the invasive gold standard measurement that utilizes an intra-arterial pressure catheter.

It should also be noted that the "maximum mean time-frequency" method disclosed herein is substantially insensitive to the orientation of the ultrasonic transducer with respect to the artery. As further detailed in Appendix A, numerous anecdotal measurements obtained by the applicant herein showed little variation under a broad range of angular pitch (i.e., rotation around an axis transverse to the longitudinal axis of the artery being measured) and roll (i.e., rotation around the longitudinal axis of the artery) values. It will be readily appreciated that such insensitivity affords great advantages to the user, since consistent results may be obtained with essentially no consideration to the angular position of the tonometric sensor(s).

Figure 5A:
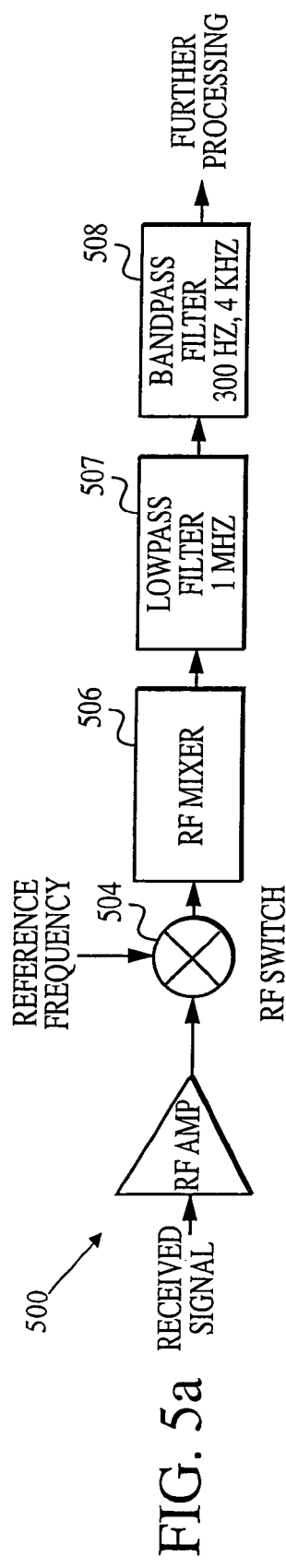
FIGS. 5a-5b are functional block diagrams of two embodiments of ultrasound filter circuits useful for measurement of Doppler shift frequencies and stationary echoes.
Figure 5B:
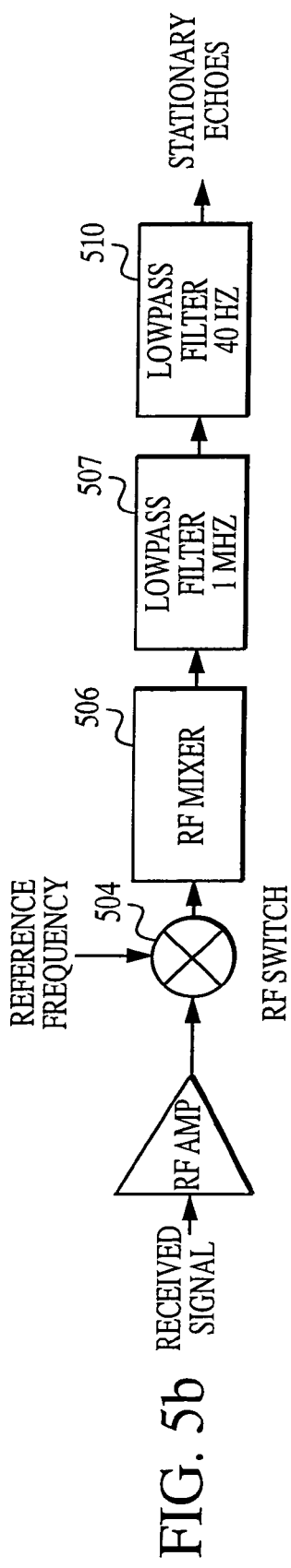

Referring now to FIGS. 5a-5b, two exemplary embodiments of the Doppler ultrasound filtering circuit used in conjunction with the method of FIG. 3c are described. In the embodiment 500 of FIG. 5a, the received signal is amplified, and supplied to a radio frequency (RF) switch 504. The switch gates the signal to the RF mixer 506, which mixes the gated bursts with the original transmission frequency. Through this demodulation scheme, the Doppler shift frequencies are isolated. A lowpass filter of 1 MHz 507 is applied to remove the signal sideband frequencies and noise, although it will be appreciated that other filter frequencies may be used. A bandpass filter 508 with a cutoff frequencies of 300 Hz and 4 kHz is then applied to remove unwanted echoes from stationary tissue such as arterial walls. The output of the bandpass filter is further processed to obtain the mean Doppler shift frequencies.

In the embodiment of FIG. 5b, for direct calculation of arterial diameter, this bandpass filter can be replaced by a lowpass filter 510 with a cutoff of 40 Hz that isolates stationary echoes. The near and far walls would be identified from the stationary echoes and used to calculate changes in arterial diameter.

Arterial Blood Pressure Measuring Apparatus

Figure 6:
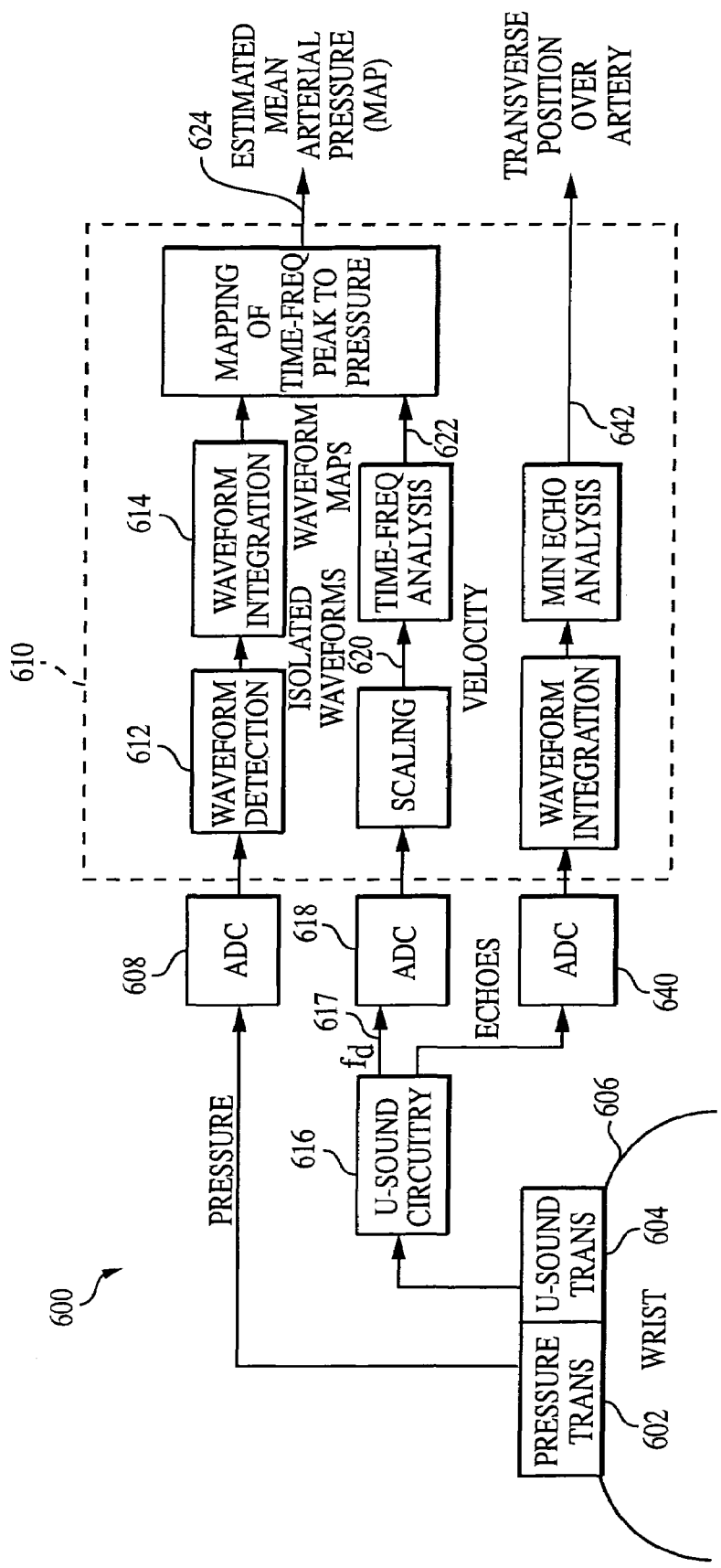
FIG. 6 is a functional block diagram of one embodiment of the arterial blood pressure monitoring device of the present invention.

Referring now to FIG. 6, one embodiment of the blood pressure measuring system according to the invention is described. As shown in FIG. 6, the system 600 comprises pressure and ultrasonic transducers 602, 604 which are placed in contact with the skin of the subject 606 during use. The pressure transducer 602 of the present embodiment is a silicon transducer of the type well known in the electrical arts, although other may be used. It will be recognized that the term "transducer" as used herein is meant to include any type of sensor capable of sensing or receiving one parameter and generating or transmitting a signal based thereon, or alternatively capable of receiving a signal and generating some physical response thereto.

Pressure applied to the face of the transducer is converted to an electrical signal bearing a known relationship thereto. The pressure transducer 602 is connected to a first analog-to-digital converter (ADC) 608, which converts the analog signal generated by the pressure transducer 602 to a digital representation. In the present embodiment, a 12-bit ADC is used, although it will be appreciated that other types may be substituted. The digitized pressure signal is then supplied to a digital signal processor (DSP) 610. Within the processor, each pressure waveform is detected using wavelet transforms 612. Wavelet transforms are known to those skilled in the art to easily detect edges, or in this case the onset of new waveforms, while noise is present. Each isolated waveform is then integrated to determine its mean arterial pressure value 614.

The ultrasonic transducer 604 generates and transmits an acoustic wave based on a first electrical signal applied thereto, and subsequently generates a second electrical signal upon receiving pressure waves in the form of echoes resulting from the transmitted acoustic waves. The first electrical signal is generated via an ultrasonic driving and receiving circuit 616, which is described in greater detail with reference to FIG. 7. The driving and receiving circuit 616 generates electrical pulses which, when applied to the transducer 604, produce acoustic energy having a frequency on the order of 8 MHz, a pulse width or duration of approximately 8 microseconds, and a pulse repetition interval (PRI) of approximately 16 us, although other values of frequency, pulse width, and PRI may be used. Hence, the transducer 604 of the present embodiment emits an 8 microsecond pulse, which is followed by an 8 microsecond "listen" period, every 16 microseconds. The echoes from these pulses are received by the ultrasonic transducer 604 during the listen period. The ultrasonic transducer 604 of the present embodiment is a silicon strain gauge or ceramic piezoelectric device of the type well known in the art, although other types may be substituted. The transducer 604 converts the received acoustic signal to an electrical signal, which is then supplied to the receiving section of the ultrasonic driver and receiver circuit 616, which contains two receiver circuits. The output of the first receiver circuit is an analog signal representative of the Doppler frequency $f_d$ of the echo received by the transducer 604. The analog output 617 is then converted to a digital representation by a second ADC 618, and supplied to the DSP 610. Within the DSP, the digitized Doppler frequency is scaled to compute the blood velocity 620 within the artery $|\bar{v}|$ based on the Doppler frequency $f_d$, as described above. The time-frequency distribution of the blood velocity 622 is then computed. Finally, the DSP maps in time the peak of the time-frequency distribution to the corresponding pressure waveform to produce the estimated MAP 624, based on the method of FIG. 3a described above.

The output of the ultrasonic receiver circuit 616 is an analog echo signal proportional to absorption of the transmitted frequencies by blood or tissue. This analog signal is converted to a digital representation by a third ADC 640 and supplied to the DSP 610. Within the DSP, each group of echoes, generated for a different transversal position, is integrated to determine a mean value 642. The mean echo values are compared to determine the minimum value, which is caused by direct positioning over the artery.

The use of such algorithms running on digital signal processing devices (such as the DSP 610) to perform mathematical calculations is well known in the signal processing arts, and accordingly will not be described further herein. The DSP's output signal is then converted to a form useful to the user such as a digital or analog display, computer data file, or audible indicator.

Figure 7:
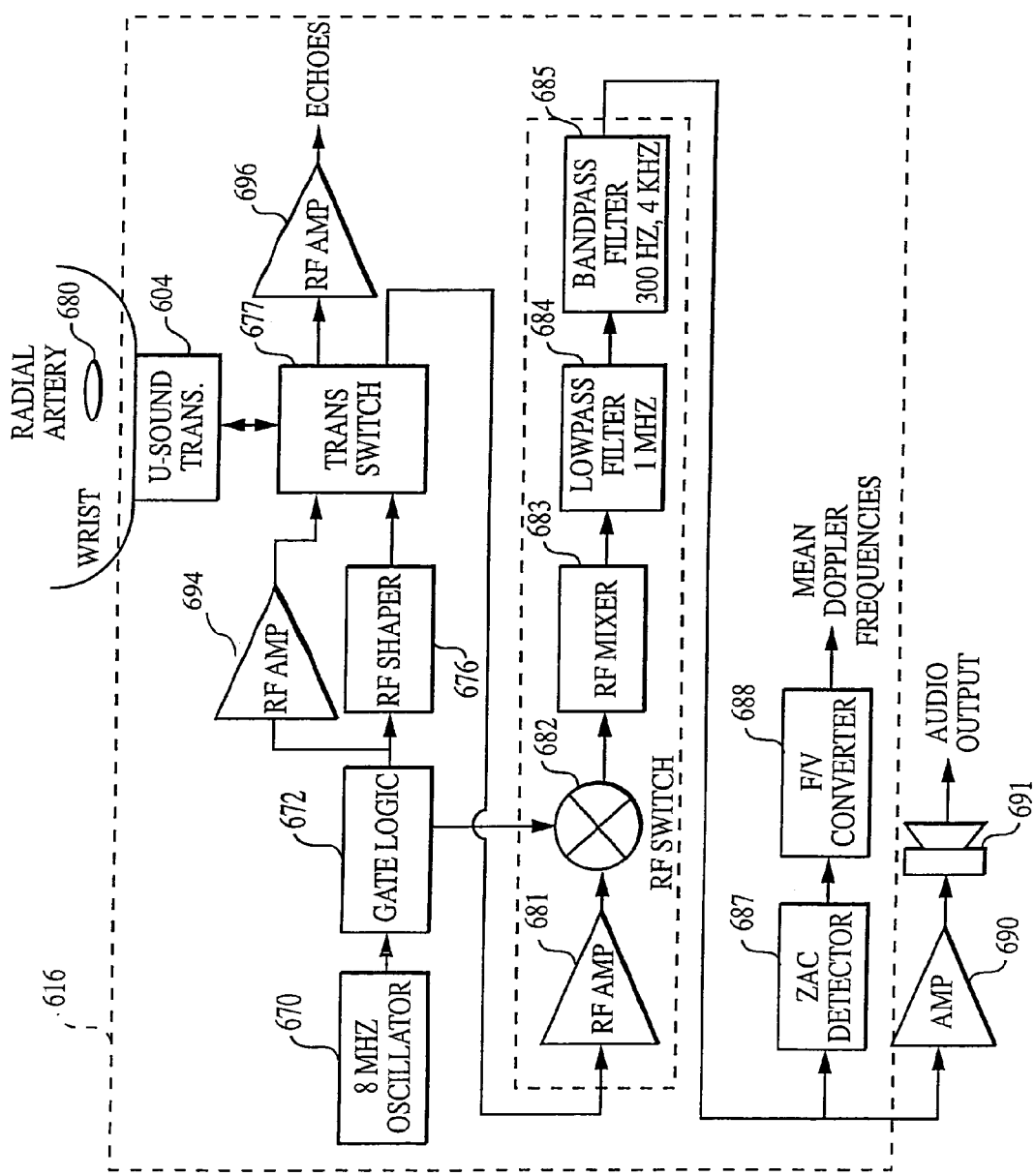
FIG. 7 is a block diagram of one embodiment of the ultrasound receiver circuit used in conjunction with the blood pressure monitoring device of FIG. 6.

Referring now to FIG. 7, which incorporates the ultrasonic filtering circuit of FIG. 5a, one embodiment of the ultrasonic driver and receiver circuit 616 is now described. As shown in FIG. 7, an oscillator 670 generates a continuous square wave signal, having a fixed frequency of 8 MHz, for coupling to a gate logic circuit 672 and to an RF mixer 683. The gate logic circuit transmits 8 us bursts of the 8 MHz signal, interrupted by 8 microsecond dead times. An RF shaper circuit 676 converts the resulting series of square wave bursts from the gate logic circuit 672 into corresponding sine wave bursts, for application through a transducer switch 677, to the ultrasonic transducer 604. The transducer switch 677 routes ultrasonic signals for both applanation and transverse positioning. The ultrasonic transducer 604 is thereby conditioned to transmit a succession of 8 MHz bursts of sonic energy into the adjacent wrist tissue.

In use, the transmitted bursts of sonic energy are scattered by red blood cells flowing through the subject's radial artery 680, and a portion of the scattered energy is directed back toward the ultrasonic transducer 604. The time required for the return energy to reach the ultrasonic transducer varies according to the speed of sound in the tissue and according to the depth of the artery. Typical transit times are in the range of 6 to 7 microseconds.

The ultrasonic transducer 604 is used to receive the reflected ultrasound energy during the dead times between the successive transmitted bursts. For the applanation application, the ultrasonic transducer therefore produces a received signal, of relatively low magnitude, and this received signal is coupled to an RF amplifier 681 for amplification. The amplified signal is then supplied to an RF switch 682, which gates the signal to the RF mixer 683 only during the dead times between successive transmitted bursts. The RF mixer 683 mixes these gated bursts with the original 8 MHz signal received from the oscillator.

The frequency of the ultrasonic transducer's transmit signal will differ from that of the return signal, because the scattering red blood cells within the radial artery are moving. Thus, the return signal, effectively, is frequency modulated by the blood flow velocity. The signal output by the RF mixer 683, therefore, will incorporate the 8 MHz fundamental frequency, as well as sum and difference frequencies of the transmit and return signals. This output signal is supplied to a lowpass filter 684 with cutoff frequency of 1 MHz, for removal of the 8 MHz fundamental frequency, as well as any higher-order harmonics from the difference frequencies. A bandpass filter 685 that ranges from 300 Hz to 4 KHz then removes all signal components other than those components representing the actual blood velocity.

The signal output from the bandpass filter 685 is supplied to a zero-axis crossing detector 687, which functions to produce a pulse each time the signal crosses a zero axis. These pulses are supplied to a frequency-to-voltage converter circuit 688, which produces a DC output signal indicative of the mean Doppler frequencies. The signal output by the bandpass filter 685 is also supplied to an audio amplifier 690, and in turn to a speaker 691, to enable an operator to hear a representation of the Doppler signals and thereby to determine when the transducer is located approximately over the radial artery.

The output of the gate logic circuit is also amplified via an amplifier 694, and when transverse positioning is desired, switched to the ultrasonic transducer 604. The received echoes are coupled to an RF amplifier 696 and output for further processing to determine minimum echo value as a function of position.

It is noted that while the embodiment of FIGS. 5a and 7 utilizes a preselected pulse duration of 8 microseconds and pulse repetition interval of 16 microseconds, other acoustic sampling techniques may be used in conjunction with the invention. For example, in a second embodiment, the ultrasonic driver and receiver circuit (not shown), the acoustic pulses are range-gated with a more complex implementation of the gate logic. As is well known in the signal processing arts, range-gating is a technique by which the pulse-to-pulse interval is varied based on the receipt of range information from earlier emitted and reflected pulses. Using this technique, the system may be "tuned" to receive echoes falling within a specific temporal window which is chosen based on the range of the echo-producing entity in relation to the acoustic source. The delay time before the gate is turned on determines the depth of the sample volume. The amount of time the gate is activated establishes the axial length of the sample volume. Thus, as the acoustic source (in this case the ultrasonic transducer 604) is tuned to the echo-producing entity (red blood cells, or arterial walls), the pulse repetition interval is shortened such that the system may obtain more samples per unit time, thereby increasing its resolution. It will be recognized that other acoustic processing techniques may also be used, all of which are considered to fall within the scope of the claims appended hereto.

Figure 8:
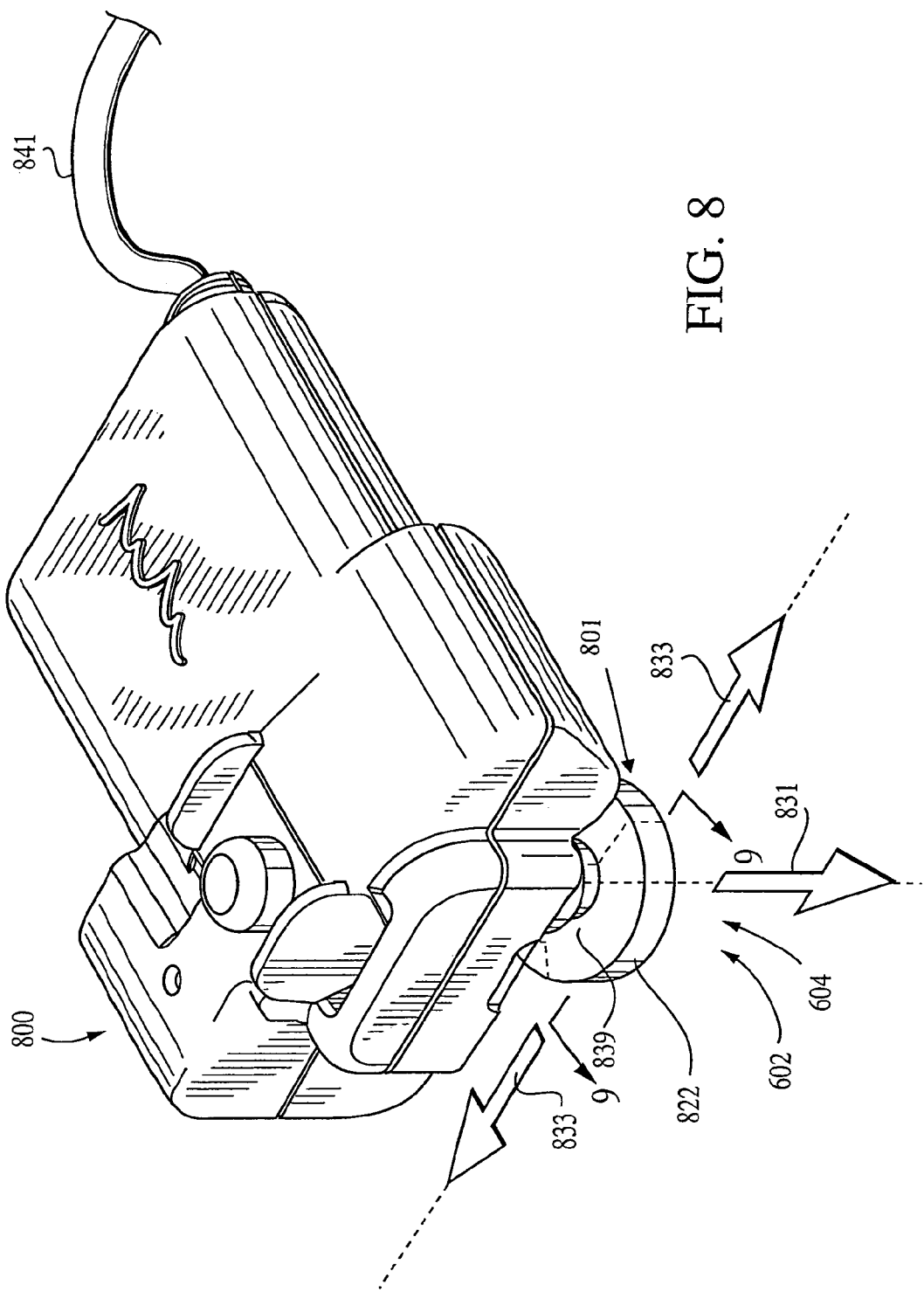
FIG. 8 is a perspective view of one embodiment of the applanation and transverse positioning assembly of the invention.
Figure 9:
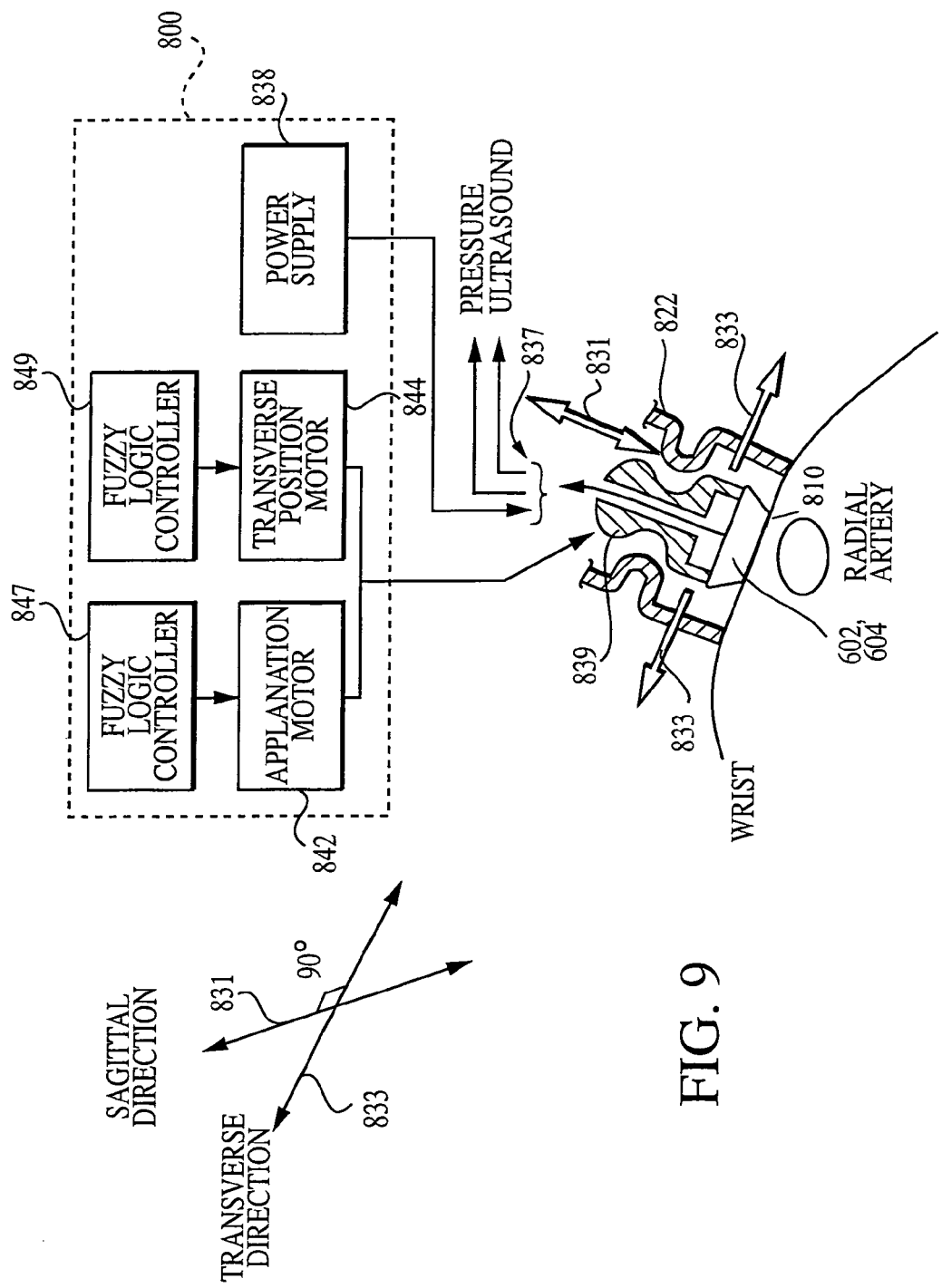
FIG. 9 is a cross-sectional view, including functional block diagram, of the blood pressure measurement system of the invention, taken along lines 9-9 of FIG. 8.

Referring now to FIGS. 8 and 9, one embodiment of the applanation and transverse positioning device 800 of the invention is illustrated. It is noted herein that FIG. 9 represents a cross-sectional view (including functional block diagram) of the blood pressure measurement system of the embodiment of FIG. 8, taken along lines 9-9 of FIG. 8. The device 800 is adapted to receive a transducer housing element 822 in the lower extensive portion thereof. The transducer housing element contains the aforementioned pressure and ultrasonic transducers 602, 604 therein, the latter physically being combined into a single transducer element, although other configurations including a tandem ultrasonic/pressure configuration (not shown), or an array of multiple pressure and/or ultrasonic transducers, may be used. The transducers 602, 604 are free to move within the housing 822 in the sagittal direction 831 and the transverse direction 833 with respect to the artery, as driven by the applanation and positioning motors 842, 844. The housing element 822 of the present embodiment contacts the wrist skin circumferentially around the transducers 602, 604 which move with respect to the housing element 822 and the skin, although it will be appreciated that a variety of different configurations and methods may be used. For example, a substantially compliant housing which conforms to the tissue of the subject, yet allows the transducers 602, 604 to move in the desired directions within an aperture therein, may be substituted. When adhered to the wrist using the wrist brace disclosed herein in FIG. 10 (or other retaining mechanism), the active surface of the transducers 602, 604 is in variable contact with the skin of the wrist, and roughly flush with the bottom edge of the housing element 822. The top of the transducers 602, 604 include an electrical connection 837 to the power supply 838 of the applanation and transverse positioning assembly 800, as well as to circuitry for processing the pressure and ultrasound signals from the transducers. The transducers are also coupled via a mechanical connection 839 to the motors of the applanation and transverse positioning assembly 800, such that the position of the transducers 602, 604 is varied in the sagittal and transverse directions by the applanation and transverse positioning motors 842, 844, respectively. While a ball-and-socket arrangement is illustrated for the mechanical connection 839 between the transducers 602, 604 and the motors, it will be appreciated that a variety of different arrangements (such as an articulated joint or sliding coupling) may be used. Collectively, the housing element 822 and the applanation and transverse positioning assembly 800 comprise a coupling device, which maintains the transducers 602, 604 properly coupled to the subject's wrist when mounted in the wrist brace of FIG. 10. The transducers 602, 604 move in the sagittal direction 831 within the housing element 822 as urged by the applanation motor 842 so as to compress the radial artery to varying degrees during blood pressure measurement. The transverse positioning motor 844 moves the transducers in the transverse direction 833 within the housing element 822 during transverse positioning (described below). In the present embodiment, the applanation motor is controlled by a fuzzy logic control circuit 847 of the type well known in the art so as to perform applanation sweeps, which vary the degree of arterial compression, although other control schemes may be used. For example, the applanation of the artery may be performed so as to maintain the transmural pressure at or near zero. Alternatively, the applanation motor may be modulated by the control circuit in a periodic or continuous fashion such that the artery is compressed according to a desired profile, such as a sinusoid. Such control and modulation schemes are described in Applicant's two U.S. Pat. Nos. 6,228,034 and 6,176,831, both entitled "Apparatus and Method for Non-Invasively Monitoring a Subject's Arterial Blood Pressure" and filed Jul. 20, 1998, which are incorporated herein by reference in their entirety.

The transverse positioning motor 844 of the assembly 800 is used to position the transducers 602, 604 directly over the artery of interest. Specifically, the ultrasonic emissions of the ultrasonic transducer 604 are substantially normal to the surface of the subject's skin and are used to generate echoes, which are reflected from the blood and tissues. These echoes are received by the transducer 604 and analyzed so as to determine their amplitude as a function of transverse position of the transducer over the artery. As with the applanation motor 842 described above, the transverse positioning motor 844 is controlled via a fuzzy logic control circuit 849 which signals the motor 844 to adjust the transverse position of the transducer such that the amplitude of the echoes (and SNR) is optimized. Alternatively, the user may manually position the transducer 604 using manual control circuitry based on an indication of the relative strength of the blood velocity echoes, such as may be provided to the user by an audible or visual representation thereof. For example, the audio output of the speaker 691 (FIG. 7), whose frequency is proportional to the amplitude of the received echoes, may be used to position the transducer 604. Many such control schemes for the transverse positioning motor are possible, all being within the scope of the claims appended hereto.

Figure 10:
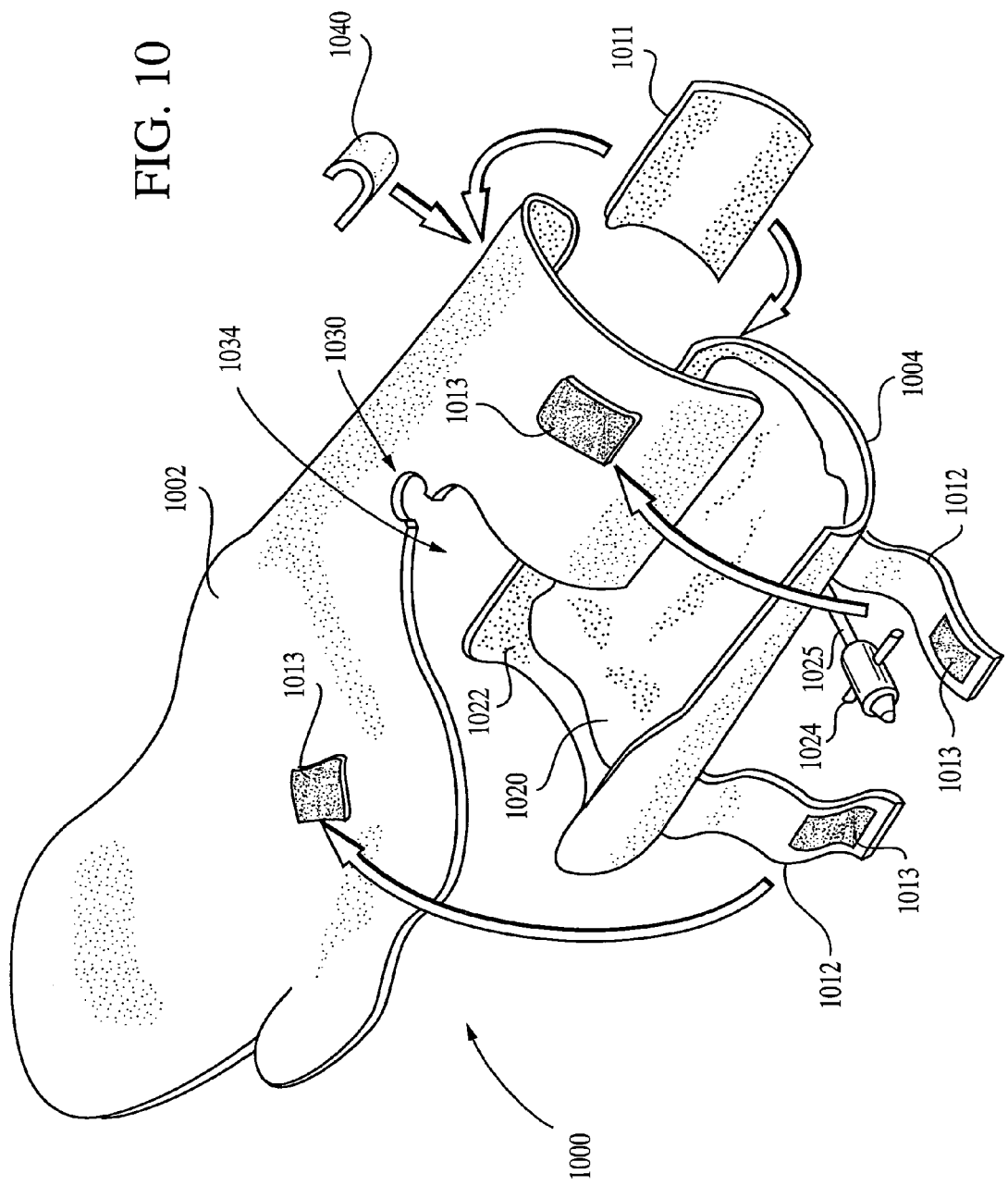
FIG. 10 is an exploded perspective view of one embodiment of the wrist brace of the present invention.
Figure 11:
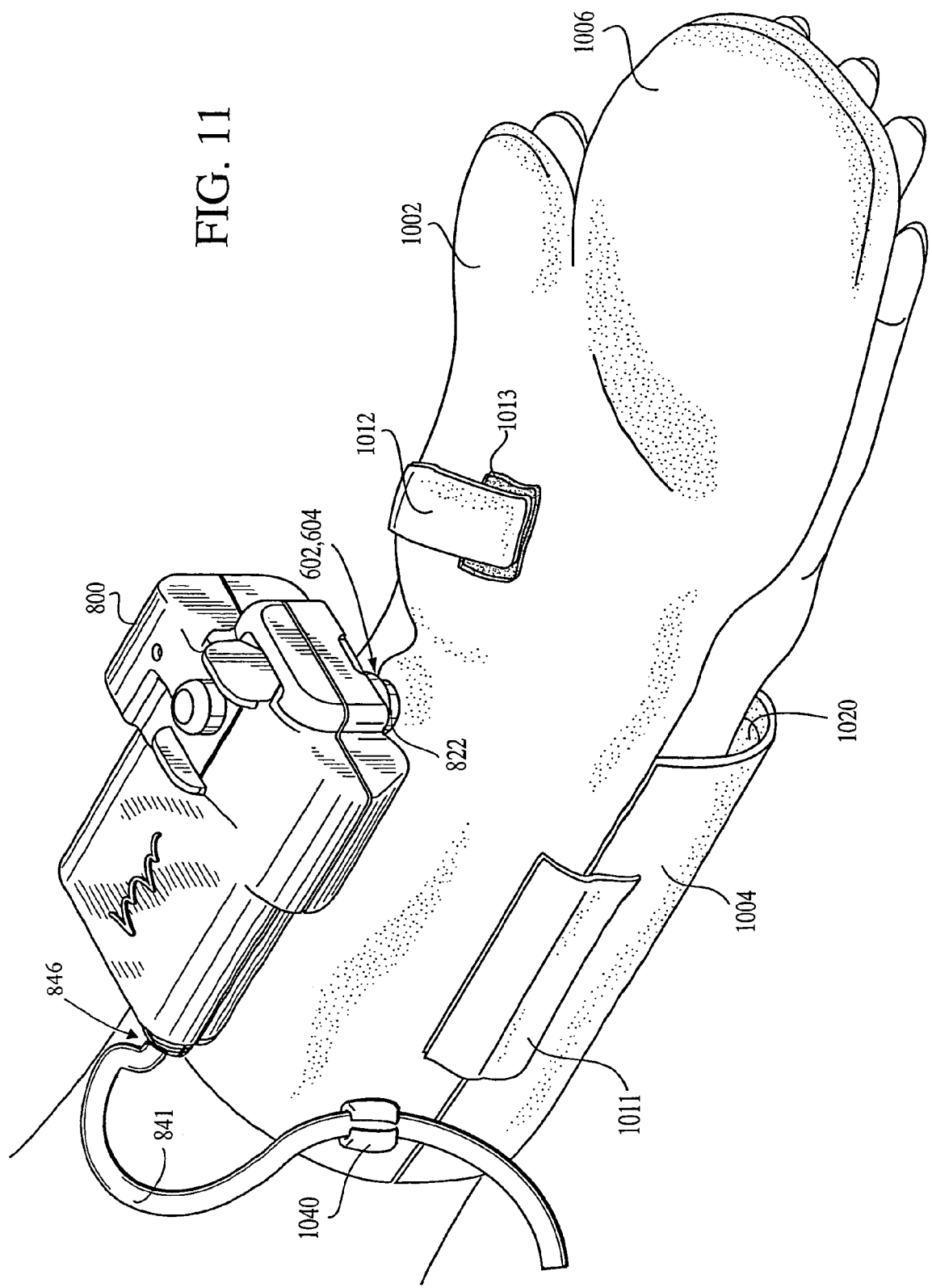
FIG. 11 is a perspective view of the wrist brace of FIG. 10 shown fitted to the wrist of a subject, and having the applanation and positioning assembly of FIG. 8 mounted thereon.

Referring now to FIGS. 10 and 11, the wrist brace 1000 of the invention is now described. In the embodiment of FIG. 10, the brace 1000 comprises an upper brace element 1002 and lower brace element 1004, which are adapted to fit the inner and outer wrist surfaces of the subject, respectively. As used herein, the terms "upper" and "lower" and "inner" and "outer" are merely descriptive of the orientation of the brace elements 1002, 1004 as illustrated in FIG. 10, and are in no way limiting as to the position or use of the brace. The upper brace element 1002 includes an extending portion 1006, which receives the inner surfaces of the subject's hand, as best shown in FIG. 11. The extending portion 1006 is contoured such that the subject's hand is retained in a natural, relaxed position, thereby increasing the time that the brace 1000 may be worn without discomfort. The upper and lower elements 1002, 1004 are joined on one common edge by a flexible fabric or polymer hinge 1011 which is fastened to both elements 1002, 1004. One or more straps 1012 are also fitted to the upper and lower elements 1002, 1004 such that when the brace 1000 is fitted to the subject's wrist and hand, the straps 1012 permit the upper and lower elements to be secured together firmly. In the present embodiment, the straps 1012 include fasteners 1013 such as Velcro tabs, although other arrangements such as mechanical clasps, snaps, slings, adhesives, or the like may be used. Likewise, the straps 1012 may be replaced partially or entirely with clasps or other similar fastening devices. It will be recognized that literally any means of maintaining the upper brace element 1002 in a substantially fixed position with respect to the lower brace element 1004 may be substituted for the straps 1012 shown in FIGS. 10 and 11.

The upper and lower brace elements 1002, 1004 are advantageously formed using a partially flexible polymer material, thereby allowing for low manufacturing cost, excellent ruggedness, and some degree of compliance with the shape of the subject's tissue. Note, however, that sufficient rigidity of these components is required to accommodate the reaction forces generated by the applanation and transverse positioning assembly 800 shown in FIG. 8 above. Specifically, the applanation and transverse positioning assembly 800 is rigidly mounted to the upper brace element 1002, as shown in FIG. 11. In one embodiment, the housing element 822 fits within an opening 1034 formed within the upper brace element 1002 adjacent to the recess 1030 such that the assembly 800 can be easily placed and "snapped into" wrist brace 1000. In a first alternative embodiment (not shown), the housing element 822 is formed within the upper brace element 1002 such that the transducers 602, 604 fit within a central aperture formed within the element 822, and the applanation and positioning assembly 800 snaps on to the outer portion of the upper brace element 1002 directly above the transducer housing element 822. In a second alternative embodiment (not shown), the applanation and positioning assembly 800 is formed directly within the upper brace element 1002. In a third alternative embodiment (also not shown), the transducer elements 602, 604 and housing element 822 are disposed within the brace 1000, with the applanation and transverse positioning assembly 800 being removably mounted thereon. It will be recognized that many other alternative configurations are possible.

The electrical cabling 841 associated with the assembly 800 is also optionally received within a routing clip 1040 mounted on the exterior of the upper brace element 1002, thereby reducing the mechanical stress on the rigid mount 846 from the cabling 841 to some degree.

The lower brace element 1004 of the present embodiment also optionally includes an inflatable bladder 1020, which is received within and fastened to the interior surface 1022 of the lower brace element 1004. The bladder 1020 is formed of a flexible material (such as a plastic or rubber) so that it can comply with the shape of the subject's wrist, and accommodate varying degrees of inflation. As used herein, the term "inflation" is meant to include inflation of the bladder 1020 by gaseous and/or liquid substances. The bladder 1020 includes a stopcock 1024 and tube 1025, which allow the user to adjust the inflation of the bladder 1020 when required. The bladder may also be connected to an automatic inflation regulating system (not shown), which dynamically adjusts the inflation of the bladder 1020 to maintain optimal positioning and/or comfort for the subject. Alternatively, the bladder 1020 may be replaced by a substantially compliant pad (not shown), such as one made of foam rubber, which will at least partially adapt its shape to that of the subject's wrist, yet maintain the wrist firmly within the brace. It can be appreciated that many such alternative embodiments are possible.

Referring again to FIG. 11, the installation and positioning of the embodiment of FIGS. 8-10 is described. The wrist brace 1000 is first fitted to the arm of the subject by the clinician such that the opening 1034 and recess 1030 in the upper brace element 1002 are located roughly atop the pulse and the radial artery. The bladder 1020 is adjusted as needed to firmly maintain the position of the brace 1000. Next, the applanation and transverse positioning assembly 800 is snapped into the recess 1030, retaining it in position. The clinician verifies that the bottom of the housing element 822 is touching the skin of the subject's wrist, and is oriented roughly normal to the wrist tissue. The electrical cabling 841 is snapped into the routing clip 1040 as well. Lastly, the ultrasonic transducer (not shown) is energized and a signal applied thereto such that acoustic waves are transmitted into the artery and surrounding tissue; echoes resulting from reflection of these waves off of the blood velocity are used (as previously described) to drive the transverse positioning control circuit and motor so as to optimize the placement of the transducer over the artery. Applanation sweeps of the artery may then be conducted, as described with respect to FIG. 3a herein.

Estimation of Catheter Systolic and Diastolic Pressures Using a Scaling Factor

Referring now to FIGS. 12-18, the method and apparatus for estimating the catheter systolic and diastolic blood pressures is described.

Figure 12:
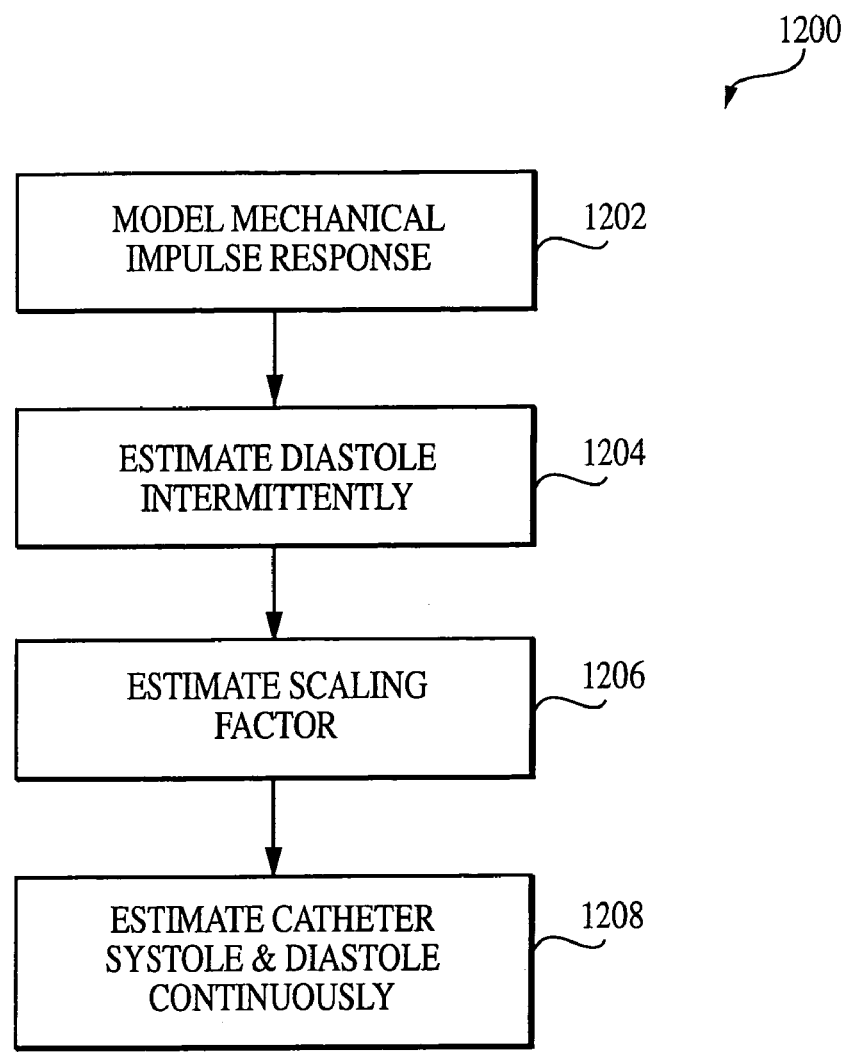
FIG. 12 is a block diagram illustrating one exemplary embodiment of the method of estimating catheter systolic and diastolic blood pressures according to the invention.

As illustrated in FIG. 12, the method 1200 generally comprises the steps of: modeling a mechanical impulse response within the subject per step 1202; estimating diastolic pressure intermittently per step 1204; estimating a scaling factor between the sensed and catheter pressure waveform per step 1206, and estimating the catheter systolic and diastolic blood pressures continuously per step 1208. These steps are described in greater detail with reference to FIGS. 13-18 below.

Mechanical Impulse Response

A mechanical impulse response exists between the true invasive or "catheter" arterial pressure and the tonometric pressure sensed at the radial artery as previously described; i.e., when the artery has been sufficiently compressed or applanated such that the sensed mean arterial pressure (MAP) equals the true MAP. To analyze the nature of this mechanical impulse response (step 1202 of FIG. 12), the impulse response is modeled as a linear controlled, autoregressive (ARX) model of the type known in the mathematical arts as illustrated in Eqn. 8.

$$\sum_{i=0}^{N} a_1 y_{servo}(n-i) = \sum_{i=0}^{M} b_i u(n-i), \quad (8)$$

where:

n=a discrete time sample, u(n)=the catheter arterial pressure, $y_{servo}(n)$=the pressure from a sensor positioned at the radial artery with sufficient pressure applied so that the sensed MAP equals the catheter MAP, $a_i$=feedback coefficient, $b_i$=feedforward coefficient, N=number of feedback coefficients and model order, and M=number of feedforward coefficients.

Figure 13:
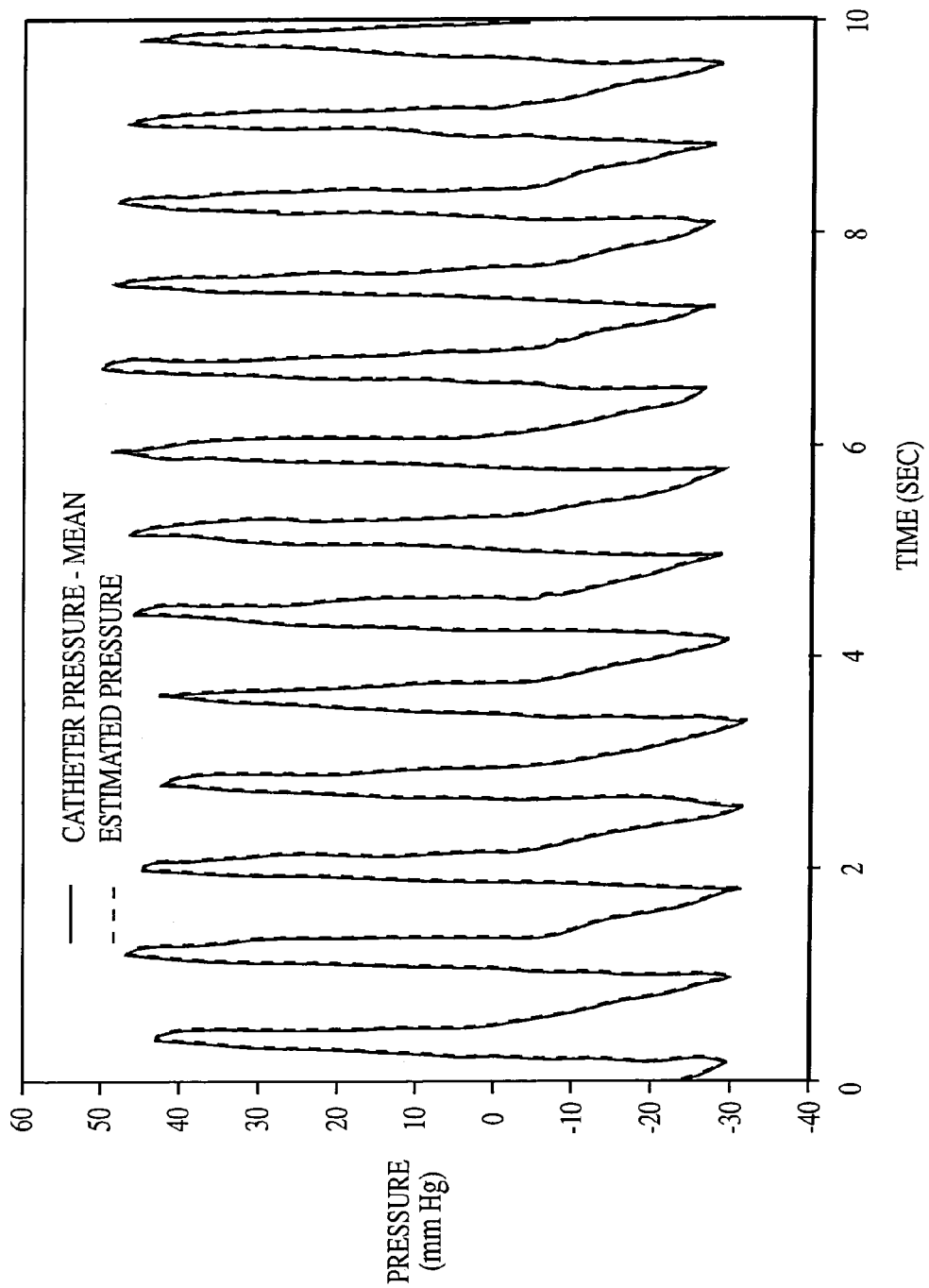
FIG. 13 is a graph illustrating the relationship between estimated catheter pressure (using zeroeth order linear autoregression model) and actual measured catheter pressure for a typical subject.

In this model, $a_0$ is chosen to be equal to 1, although other values may be used. The mean arterial pressure values obtained from the subject(s) are subtracted from their respective data sets, and fit to the ARX model, using various combinations of N and M. The optimum model order N is determined using standard criteria well known to those skilled in the art. Specifically, in the illustrated embodiment, the Akaike Final Prediction Error Criterion, standard deviations associated with identified parameter estimates (precision of estimates), and residuals between the estimated and catheter waveforms are used, although it will be recognized that other criteria may be substituted. In the present embodiment, a zeroeth order model with one feedforward coefficient is chosen. Appendix B provides exemplary anecdotal data illustrating the foregoing process. FIG. 13 graphically illustrates the fit between the catheter data and the aforementioned zeroeth order model for an exemplary subject (subject No. 2 from Appendix B).

The results of Applicant's anecdotal testing as described in Appendix B hereto indicate that the pressure sensed at the radial artery may be attenuated by a significant fraction in comparison to catheter pressure. However, while energy is lost due to the aforementioned mechanical impulse response, the catheter frequency characteristics are preserved. Therefore, the catheter systolic and diastolic pressures may advantageously be estimated using a single derived scaling factor (step 1206 of FIG. 12). In the present embodiment of the invention, this scaling factor is derived by first estimating the catheter mean and diastolic pressures, and then calculating the attenuation based on the difference between i) the estimated mean pressure minus the estimated diastolic pressure, and ii) the measured mean pressure minus the measured diastolic pressure. The estimated mean is determined by the time-frequency method and apparatus as previously described herein. Similarly, an estimate of diastolic pressure is obtained by processing the blood velocity waveforms during a decreasing applanation sweep to determine a corresponding pressure waveform whose mean corresponds to an estimate of the true diastolic pressure. The "measured" values are obtained through servo operation around the mean, as described in greater detail below.

Estimate of Diastolic Pressure

Referring now to FIGS. 14a-16, the method of estimating diastolic pressure according to the invention is described. FIGS. 14a-14d illustrate arterial pressure, blood velocity, time frequency signal and wavelet transform respectively as a function of sample number (time). As indicated above, an estimate of diastolic pressure is obtained by processing the blood velocity waveforms during a decreasing applanation sweep to determine a corresponding pressure waveform whose mean corresponds to an estimate of the true diastolic pressure. It has been observed that during the course of this decreasing applanation sweep such as that illustrated in FIG. 14a, the blood velocity contains an end-diastolic component that transiently rises and falls; see FIGS. 14b and 14c. This feature of the velocity may be related to the changes in flow characteristics or changes in arterial diameter. In particular, the time 1402 at which the end-diastolic velocity first "settles" to its final value after transiently increasing (i.e., "settling point") can indicate when the mean pressure applied externally above the radial artery is an estimate of the true diastolic pressure within the artery.

Figure 15:
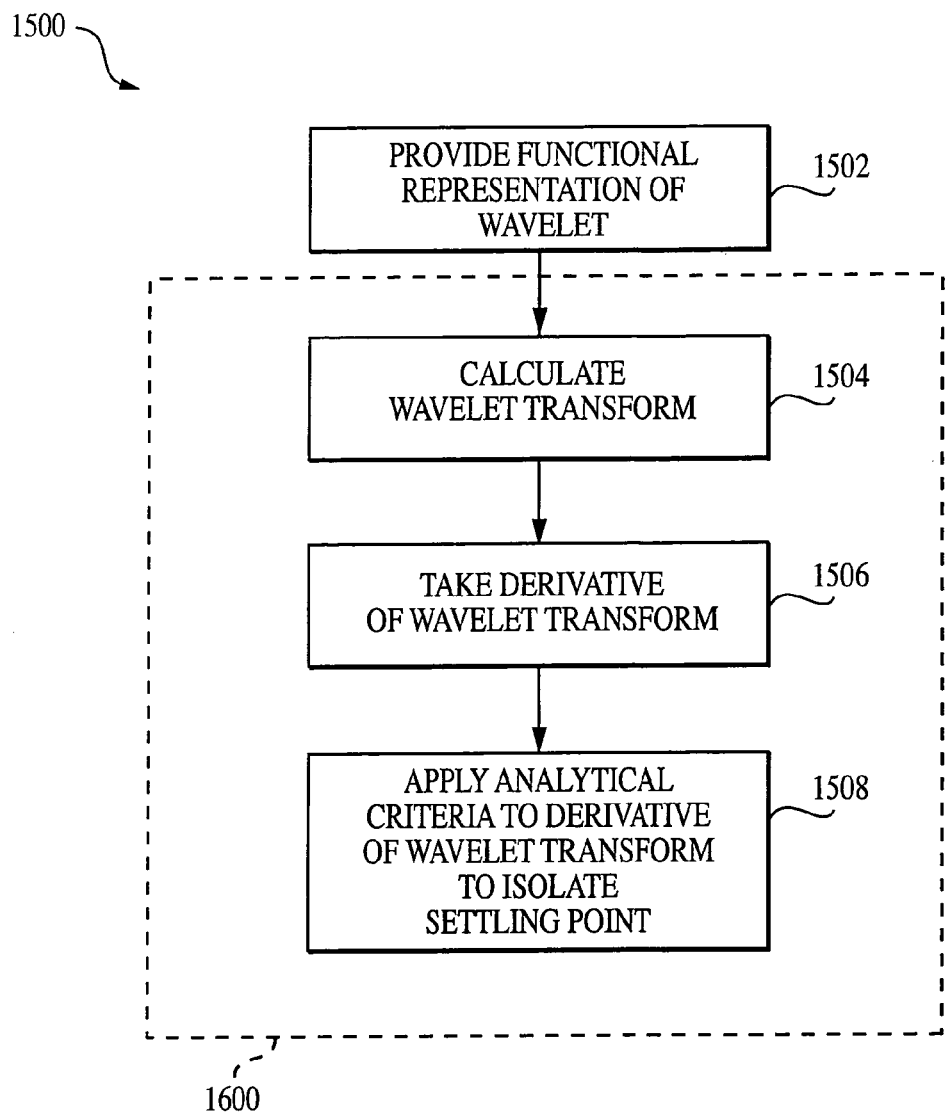
FIG. 15 is a block diagram illustrating one exemplary embodiment of the method of estimating diastolic blood pressure according to the invention.

In general, the process of mathematically isolating this settling point in the time domain is complex, yet can be simplified through processing in the time-scale domain. The generalized method of isolating the settling point according to the invention is illustrated in FIG. 15. As shown in FIG. 15, the method 1500 comprises providing a functional representation of a wavelet in step 1502; calculating a transform of the wavelet in step 1504; taking a derivative of the wavelet transform in step 1506; and applying a set of analytical criteria to the derivative of the wavelet transform in order to isolate the setting point in step 1508.

Figure 16:
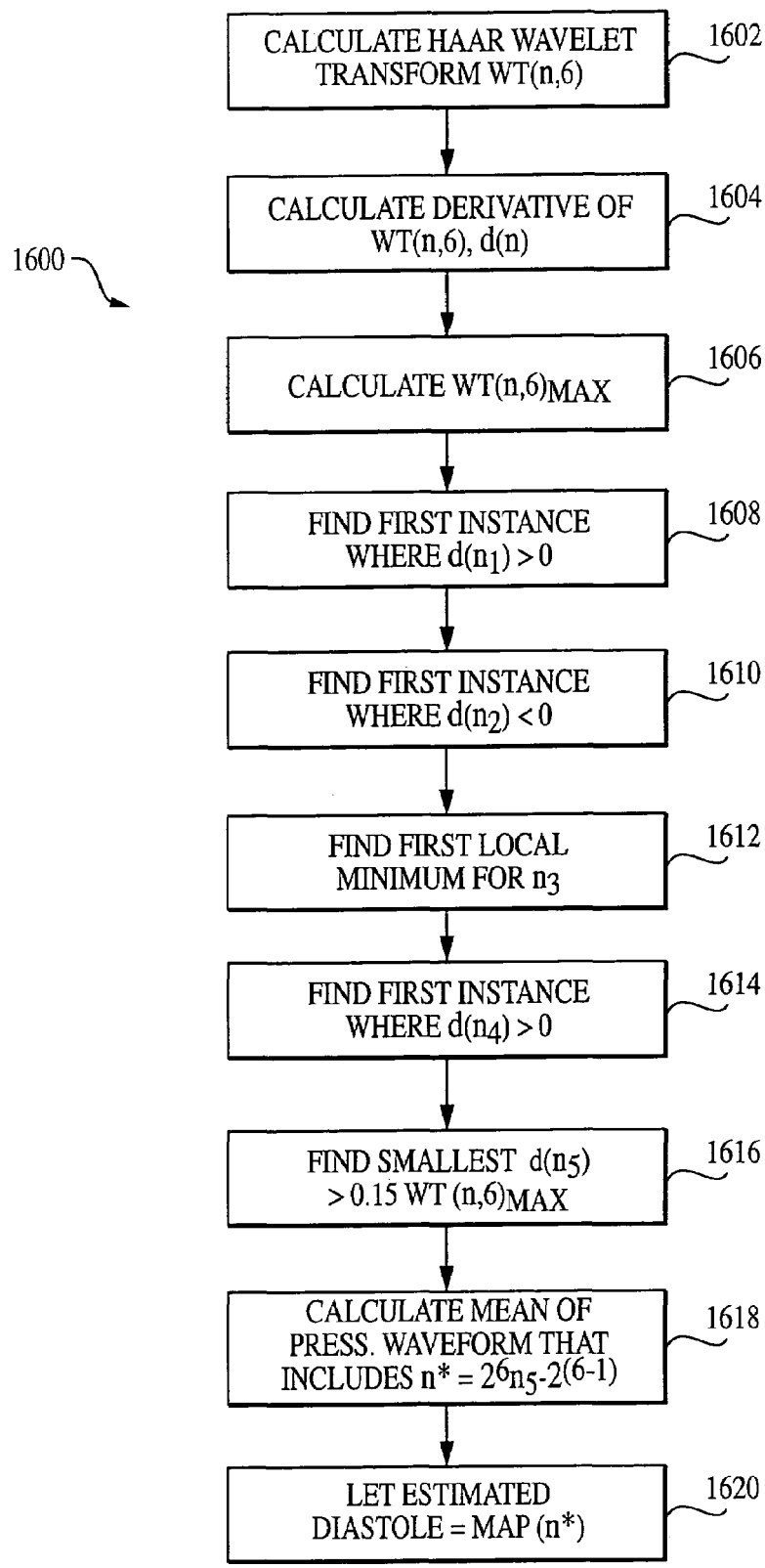
FIG. 16 is a block diagram illustrating one exemplary embodiment of the method of isolating the "settling point" within an applanation sweep according to the invention.

FIG. 16 illustrates one specific embodiment 1600 of the method 1500 of isolating the settling point. In this embodiment, the approximation coefficients of a Haar wavelet transform of scale 6 are calculated in order to enable the essential features of the end-diastolic velocity to be isolated. This transform, WT(n,6), is calculated in step 1602 as set forth in Eqn. 9 below:

$$WT(n,6) = \frac{1}{2^6} \sum_{j=0}^{L-1} x(j)\phi_h\left(\frac{j-h}{2^6}\right), \quad (9)$$

where x(n) is the blood velocity signal, L is the length of the signal (i.e., the total number of samples in the blood velocity signal), and $\phi_h(n)$ is the Haar scaling function as is well known in the mathematical arts. The Haar scaling function is defined as $$\phi_h(n) = \begin{cases} 1, & 0 \le k < 1 \\ \text{otherwise} \end{cases} \quad (10)$$

Figure 14A:
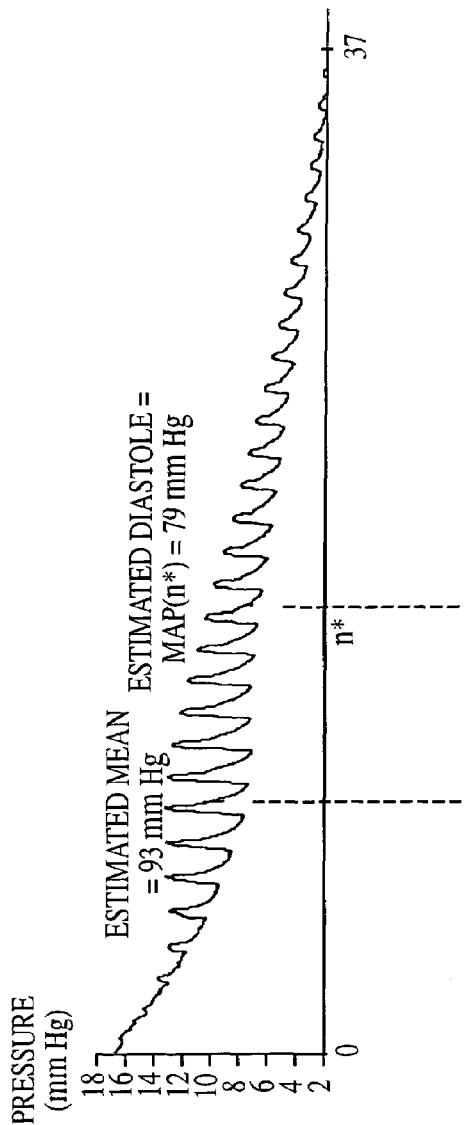
FIGS. 14a-d are graphs representing the estimated arterial blood pressure, blood velocity, time-frequency distribution, and wavelet transform/derivative, respectively, of a typical test subject.
Figure 14B:
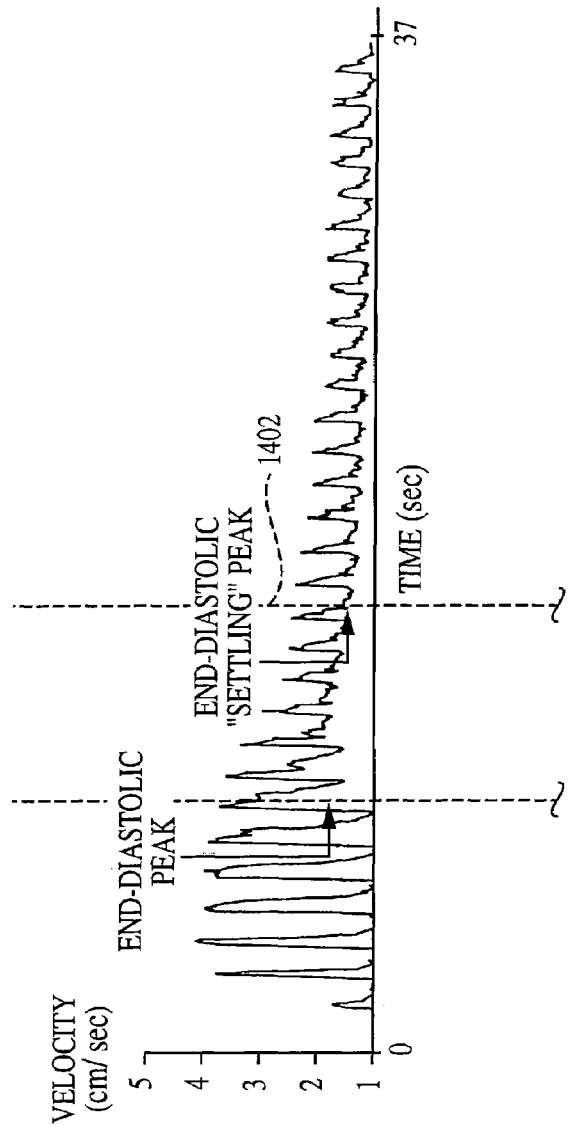

Note that the length of the wavelet transform is $\frac{1}{2}^6 = \frac{1}{64}$ the length L of the input signal. Hence, in essence, the transform functions as a low pass filter as illustrated in FIGS. 14b and 14d.

Next, to isolate the settling point, the derivative of the wavelet transform, d(n), is calculated and processed in step 1604 of FIG. 16. First, $WT(n,6)_{max}$ is calculated in step 1606. Next, starting with the first sample, the first instance where the derivative $d(n_1)$ is greater than zero ($d(n_1)>0$) is found in step 1608. Starting with sample $n_1$, the first instance where $d(n_2)<0$ is then found per step 1610. Starting from sample $n_2$, the first local minimum at sample $n_3$ is found in step 1612. In step 1614, and starting from sample $n_3$, the first instance where $d(n_4)>0$ is found. Next, in step 1616, the smallest value of $d(n_5)>0.15 \, WT(n,6)_{max}$ is found within the range $n_3<n<n_4$. The mean of the pressure waveform that includes sample $n^*=2^6 n_5 - 2^{6-1}$ is then calculated in step 1618. The estimated diastolic pressure is then determined as the value of MAP($n^*$) in step 1620.

Figure 14C:
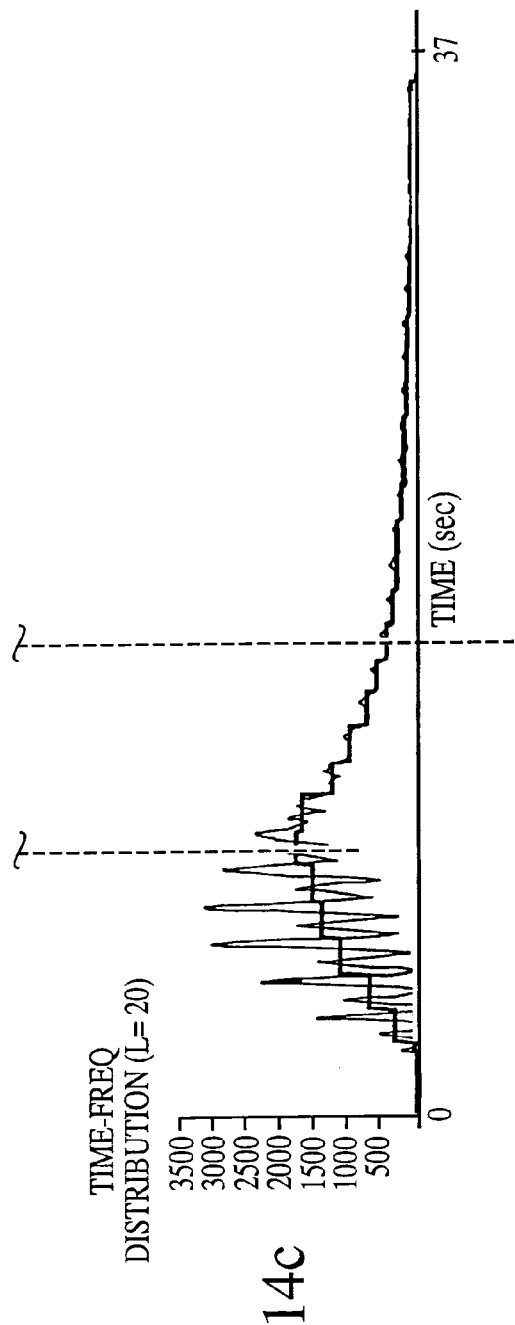
Figure 14D:
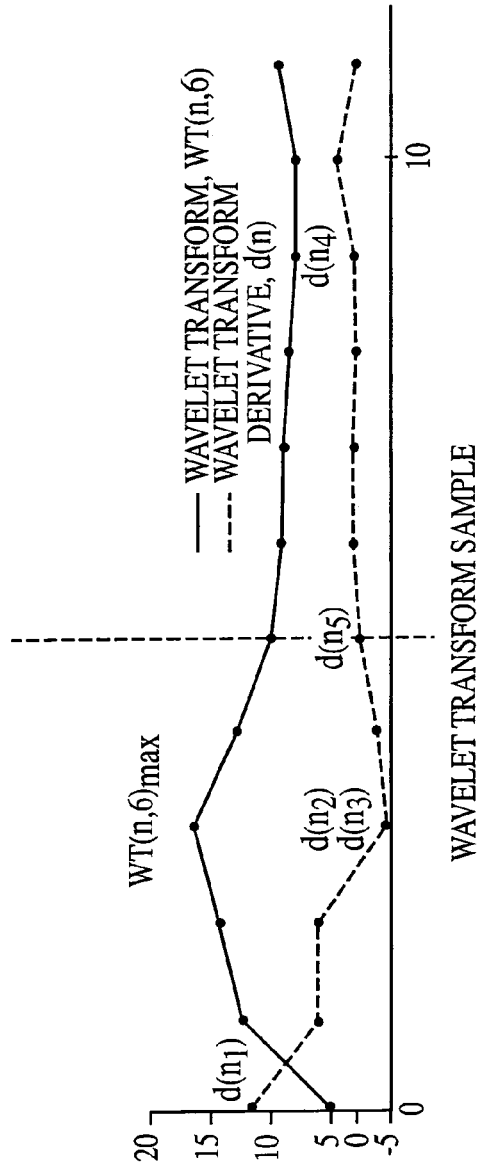

FIG. 14d illustrates the relationship of the wavelet transform WT(n,6) and derivative thereof, d(n), as related to the arterial pressure (FIG. 14a), blood velocity (FIG. 14b), and time frequency distribution (FIG. 14c).

While the embodiment illustrated in FIG. 16 and described above involves the application of a Haar wavelet transform, it will be recognized that other types of transforms and mathematical operations may be substituted consistent with the present invention to isolate the "settling point" associated with the end diastolic velocity; hence, the use of a Haar transform is merely illustrative.

Derivation of Scaling Factors

Based on the foregoing information, a first scaling factor, $F_1$, may be derived using the following equation:

$$F_1 = \frac{MAP(n') - MAP(n^*)}{MAP(n') - Diastole(n')}, \quad (11)$$

where n' is the sample identified by the time-frequency algorithm during which the measured MAP corresponds to the catheter MAP, and n* is the sample identified by the wavelet algorithm during which the measured MAP corresponds to the catheter diastole. For the waveforms associated with the zeroeth order model previously described (see Appendix B), $$F_1 = \frac{1}{b_0}.$$

In one embodiment, this scaling factor is only calculated intermittently during a calibration sweep.

While the catheter pressure is not changing significantly, the applanation may be fixed at a low, constant externally applied pressure. During this "steady state" condition, the measured MAP, $MAP_{ss}$, and measured diastolic pressure, $Diastole_{ss}$, will not change significantly. A second, "steady state" scaling factor, $F_2$, can therefore be derived using the following equation:

$$F_2 = \frac{MAP(n') - MAP(n^*)}{MAP_{ss} - Diastole_{ss}}. \quad (12)$$

Fuzzy Logic Controller and MAP Servo

As previously discussed with respect to FIGS. 8 and 9 above, one embodiment of the invention includes one or more fuzzy logic controllers (circuits) 847, 849. The fuzzy logic controller employed in the applanation motor control circuit 847 is used to servo the MAP, and possesses two inputs and one output. The two input signals of this embodiment of the control circuit 847 are based on the time-frequency signal previously described herein. Other numbers and types of inputs may conceivably be used, however, as is well understood in the art.

To calculate this time-frequency signal, the blood velocity is first acquired at a first sampling frequency $f_1$, thereby resulting in a digitized signal. In the illustrated embodiment, the blood velocity is sampled at a frequency of 400 Hz using a National Instruments ADC, Model No. DaQCard-AI-16E-4, resulting in digitized data with 12 bit resolution. It will be recognized, however, that other sampling frequencies, data conversion devices, and digital data resolution values may be substituted with equal success. The digitized data is then decimated by a factor of 20 to obtain 20 Hz data. The Pseudo-Wigner distribution at 0 Hz is calculated using Eqn. 4 above, with L=window length=5. The mean time-frequency signal is then calculated for each waveform.

The embodiment of the controller described herein seeks to maximize the mean time-frequency signal on a per-waveform (beat) basis, although other criteria may conceivably be used. The mean time-frequency signal is proportional to the end-diastolic blood velocity. The mean time-frequency signal for each waveform is passed to the fuzzy logic controller 847 as the first input. A second input to the controller 847 is derived as the difference between the current and last mean time-frequency inputs. The fuzzy logic controller 847 calculates the number of applanation steps to output as a multiple of 50 steps, ranging from −400 to +400 steps (38,400 nominal steps=1 inch). If the difference input is positive (+), the output signal directs the applanation motor to continue in the same direction for a calculated number of steps. If the difference input is negative (−), the output signal directs the applanation motor to change direction for a calculated number of steps. The input and output membership functions of the controller are typical functions of the type well known in the controller arts with 5 overlapping trapezoids, although it will be recognized that other types of membership functions may be used. Fuzzification of the illustrated embodiment uses the standard AND rule; defuzzification uses the standard centroid method.

The shift in end-diastolic velocity that is the basis of the mean time-frequency signal previously described has been anecdotally observed by the Applicant herein to be continuously present in anesthetized operating room subjects during two hour studies. Appendix C describes these observations in greater detail.

Scaling During MAP Servo

Figure 17:
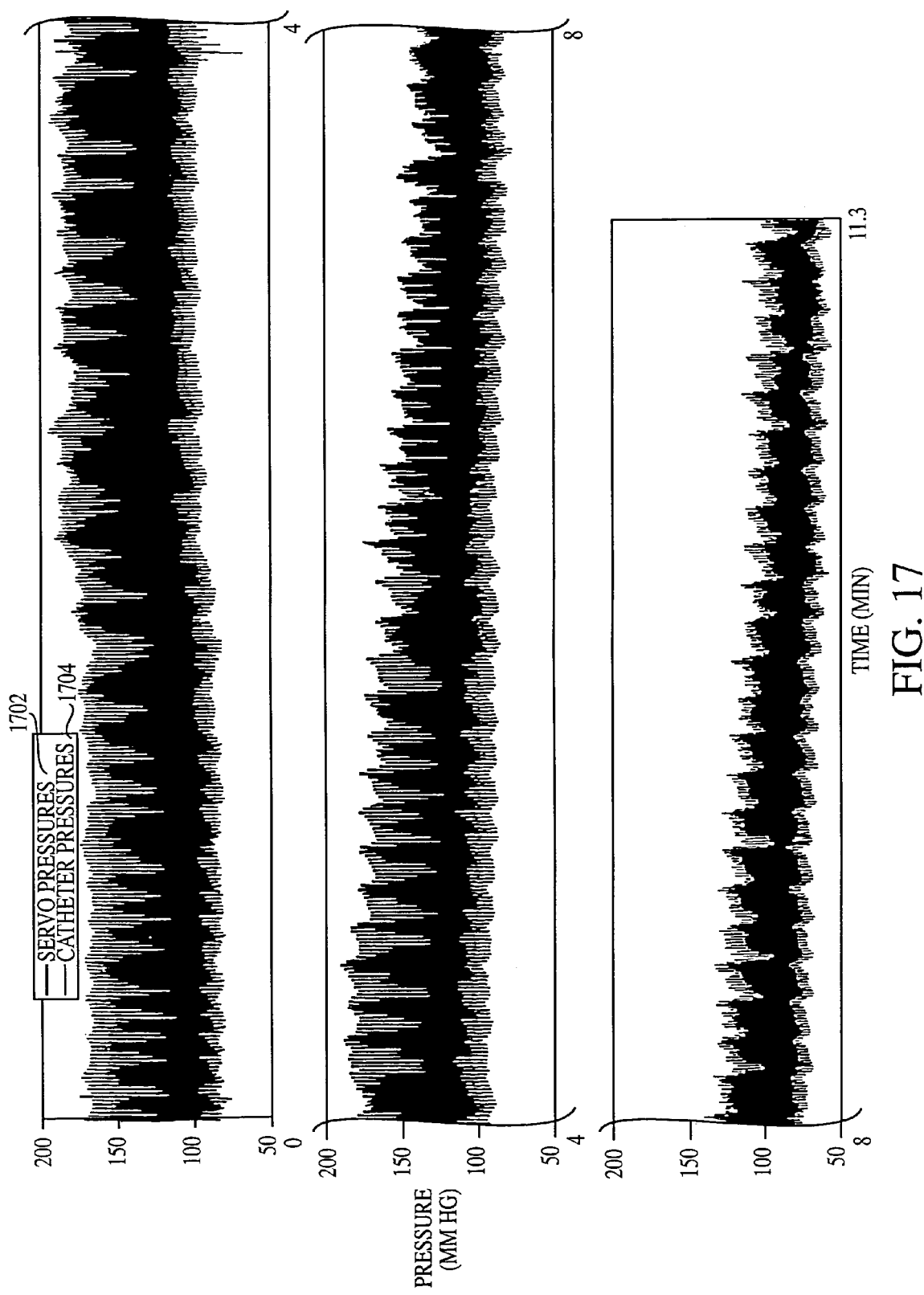
FIG. 17 is a graph illustrating the response of the servo algorithm of the invention to the time-variant arterial (catheter) blood pressure of a test subject.
Figure 18:
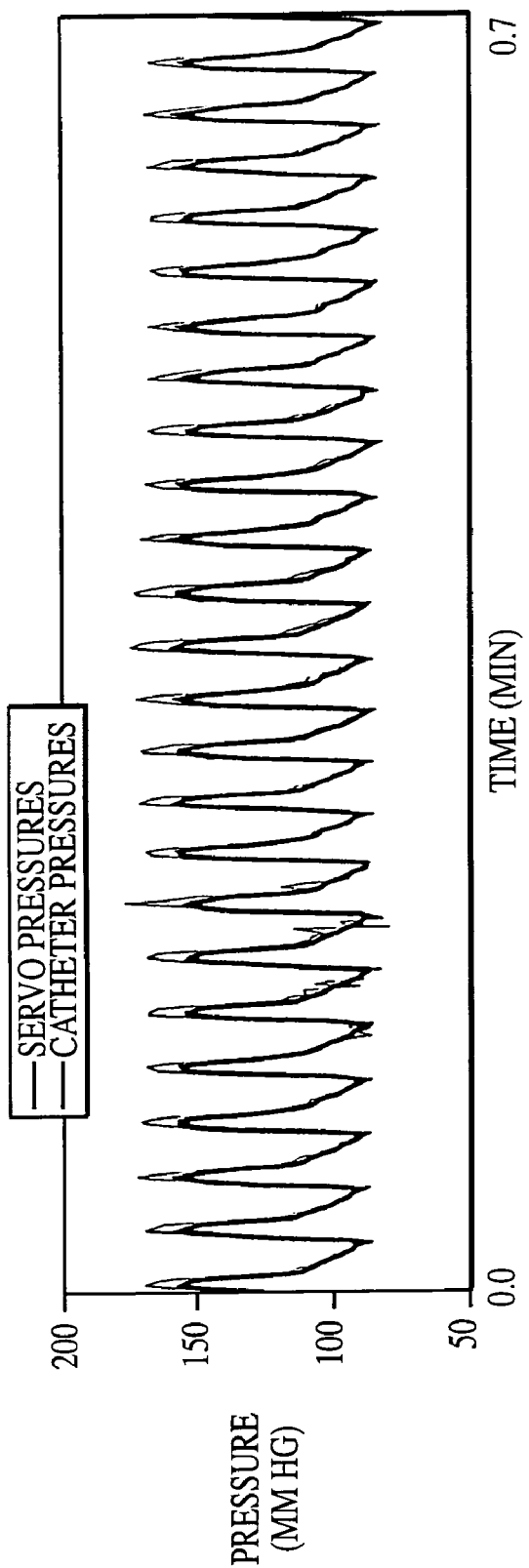
FIG. 18 is a graph illustrating three selected portions of the servo algorithm response of FIG. 17 in detail.
Figure 18:
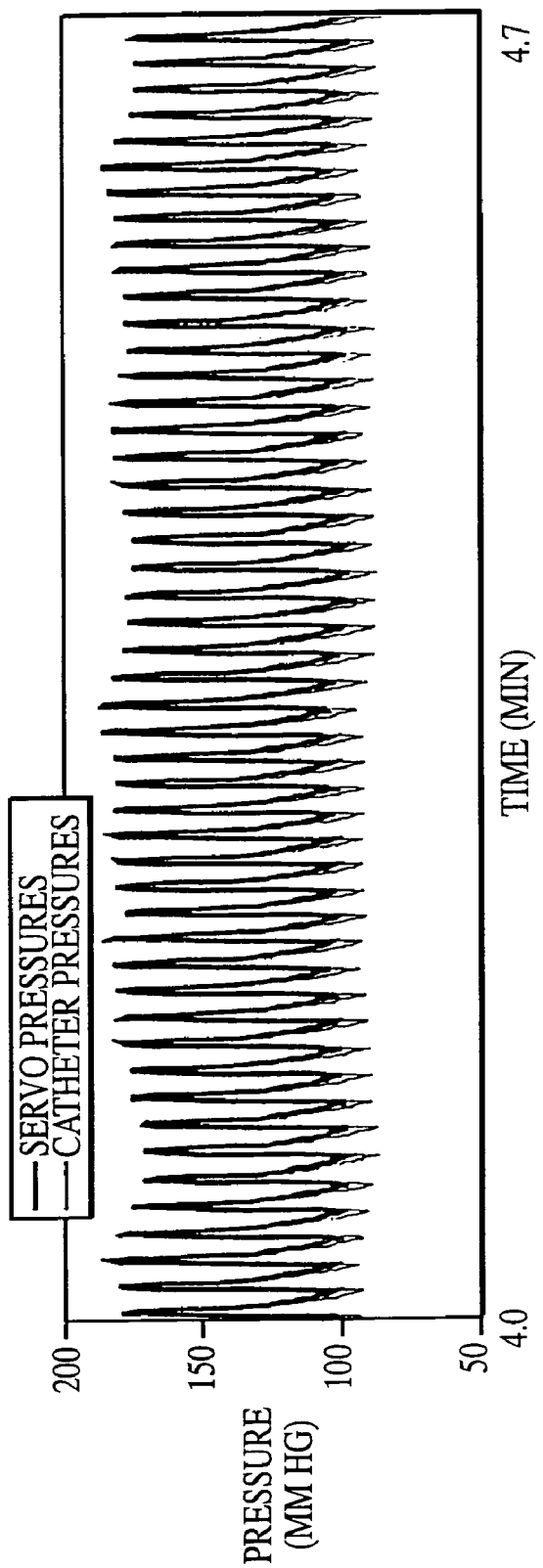
Figure 18:
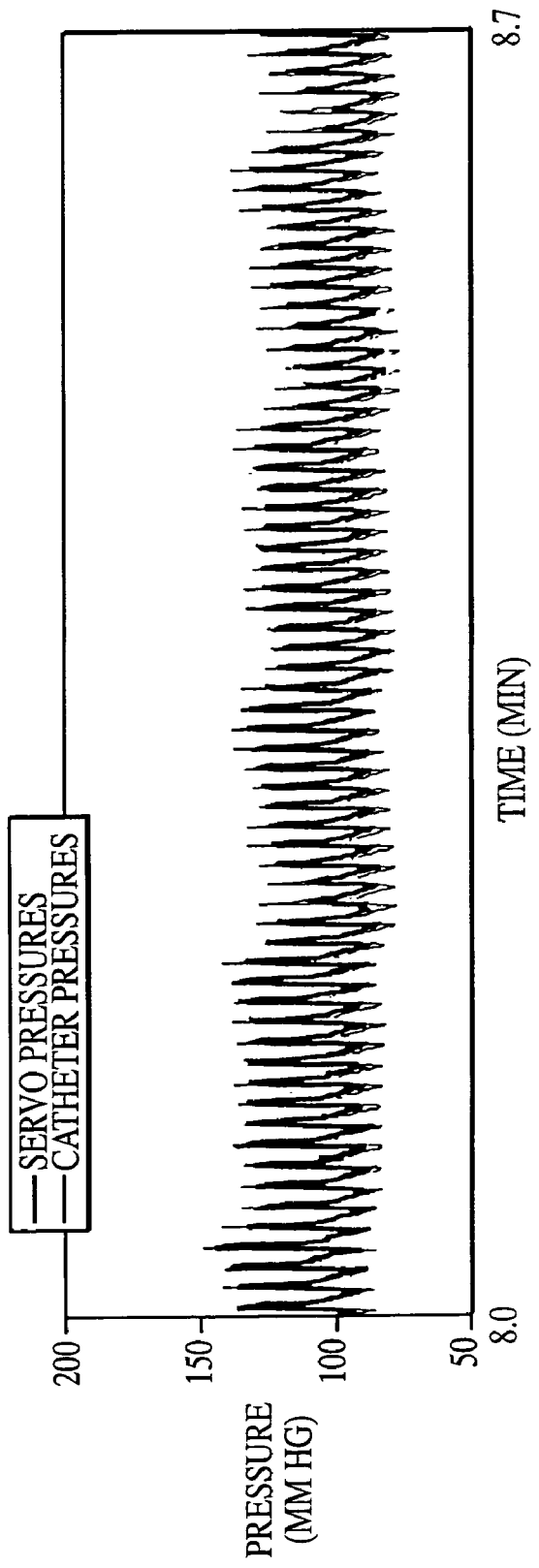
Figure 19:
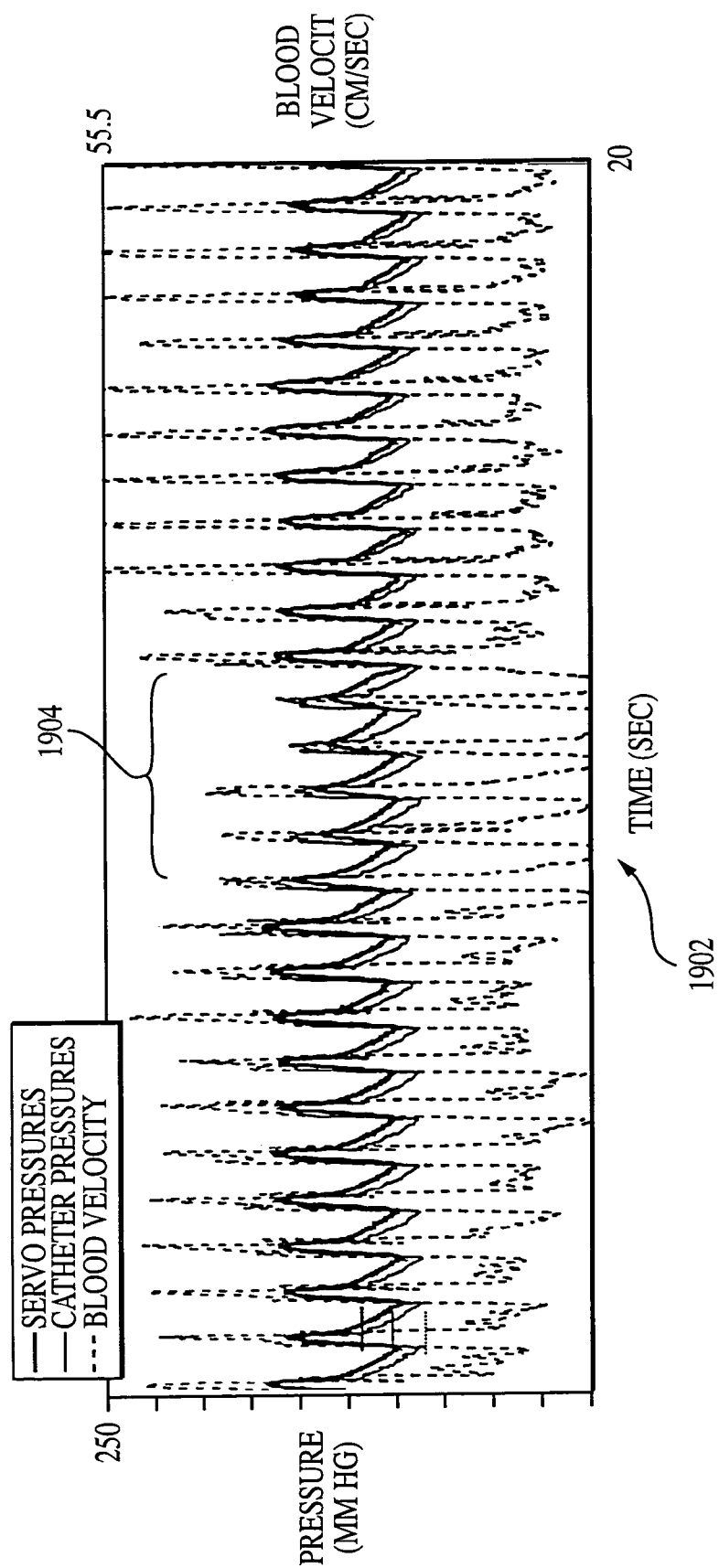
FIG. 19 is a graph illustrating a selected portion of the data presented in FIG. 17, demonstrating the self-correction response of the servo algorithm.

Between intermittent calibration sweeps, the applanation pressure is varied as previously described herein to continuously "servo" to the catheter MAP as the latter varies in time. A typical result obtained using the servo algorithm of the present invention is illustrated in FIGS. 17 through 19, and described in greater detail in Appendix C hereto. Referring to FIG. 17, the response of the algorithm to an observed 50 mm Hg drop in MAP over approximately 11 minutes for a single test subject (in response to epidural administration of the anesthetic bupivacaine) is illustrated. As shown in this Figure, the servo algorithm of the invention tracked the MAP accurately as shown by the overall correlation between servo pressure 1702 and catheter pressure 1704 over time. The mean error in tracking 552 pressure beats was 3±4 mm Hg. FIG. 18 is a detail view of FIG. 17, illustrating three forty (40) second windows of the catheter and servo data. FIG. 19 is a 20 second interval "snapshot" of the data of FIG. 17 that occurred at 6.5 minutes from onset of data recordation. As illustrated in FIG. 19, a significant drop 1902 in the end-diastolic velocity was corrected within 5 beats 1904.

By estimating the mean and diastolic pressures accurately using the foregoing method on an intermittent basis, the scaling factor, $F_1$, may be derived and applied for continuous estimation of systole and diastole, as well as the entire blood pressure waveform, $y_{scaled}(n)$:

$$y_{scaled}(n) = F_1(y_{servo}(n) - MAP_{servo}) + MAP_{servo}. \quad (13)$$

Scaling During Steady State Pressure

During periods of steady state pressures (i.e., when the catheter pressure does not vary significantly), a low constant applanation is applied externally to minimize trauma to the wrist of the subject. By estimating the catheter mean and diastolic pressures accurately, the scaling factor, $F_2$, may be derived and applied for continuous estimation of systole and diastole, as well as the entire blood pressure waveform:

$$y_{scaled}(n) = F_2(y_{ss}(n) - MAP_{ss}) + MAP(n'). \quad (14)$$

During continuous blood pressure estimation, the system will alternate between periods of servoing to the catheter MAP while blood pressure is in flux, and periods of applying a low constant applanation pressure while blood pressure is in steady state.

Blood Vessel Location and Positioning

As previously discussed, proper transverse positioning of the ultrasonic and pressure transducers of the apparatus is beneficial in terms of enhanced accuracy of measurement of hemodynamic parameters including arterial blood pressure. Such transverse positioning is generally predicated upon initial placement of the apparatus in the locale of the blood vessel of interest, and subsequently "fine tuning" the position of the transducer(s) such that optimal coupling is achieved. In the case of the human radial artery, the approximate location of the artery is known by the caregiver; i.e., running longitudinally down the inside surface of the wrist/forearm of the subject, within a narrow band corresponding to something less than the width of the wrist. However, for other blood vessels and/or species, the location and orientation of the blood vessel of interest may not be as easily identified. Even in the context of the human radial artery, where the approximate location and orientation of which is well known, improper placement of the apparatus by the caregiver can affect the consistency and "robustness" of blood pressure measurements obtained from that location. Movement by the patient (and other factors) may also affect the accuracy of the reading, and require periodic relocation/repositioning of the measurement apparatus.

Furthermore, there are other types of procedures, including for example carotid artery surgery (mapping of the vessel along the human neck), femoral artery catheterization, and temporal artery localization, wherein it is highly desirable to be able to either (i) readily and reliably locate a blood vessel within the tissue of the subject in a non-invasive manner, or (ii) maintain a monitoring or treatment device in a predetermined position and orientation with respect to the blood vessel once located.

Accordingly, the present invention advantageously provides such a non-invasive technique (and apparatus) for both locating the blood vessel of interest, and maintaining one or more selected apparatus in a predetermined relationship thereto. Specifically, in one exemplary application, backscattered acoustic energy is analyzed to initially locate the blood vessel which is embedded within the surrounding tissue of the subject. In another application, the backscattered energy is used to maintain a sensing or treatment apparatus (e.g., the pressure and/ultrasonic transducers assembly 800 of the NIBP device previously described herein, or that described in Assignee's U.S. Pat. No. 7,048,691 entitled "Method and Apparatus for Assessing Hemodynamic Parameters Within the Circulatory System of a Living Subject" filed Mar. 22, 2001, and incorporated by reference herein in its entirety) in optimal position with respect to the blood vessel.

In one embodiment, the method of detecting and locating the blood vessel of interest is accomplished by directly detecting the lumen associated with the blood vessel based on reduced levels of backscattered ultrasonic energy present in "A-mode" line scans; ultrasonic energy is more readily absorbed within the lumen (such as by the red blood cells and plasma present within the blood) than by the surrounding vessel walls and tissue. Hence, the vessel is located, and/or the monitoring device positioned, by identifying regions of reduced backscattered energy. Such regions may be found in one dimension (e.g., only in terms of depth within the tissue), or multiple dimensions, such as where it is desired to precisely locate the vessel both in terms of lateral or transverse position and depth.

Another embodiment of the invention detects the relative locations of both the front and rear walls of the blood vessel based on analysis of backscattered A-mode energy. This wall information is used to indirectly determine the effective diameter of the blood vessel; the variation in blood vessel diameter as a function of lateral or transverse position is then used to identify the optimal lateral position of the measurement or treatment device. Note that the act of "lateral" positioning as described herein may also include some component of longitudinal positioning (i.e., along the longitudinal axis of the blood vessel), since placement of the apparatus on the wrist/forearm of the subject is governed more by the physical attributes of the wrist, as opposed to the orientation of the blood vessel within the wrist/forearm. Specifically, in the cases where the point of measurement for the transducer (s) occurs at a location where the radial artery runs in a direction not perfectly parallel to the axis of the wrist bone, such "lateral" positioning inherently includes a longitudinal component as well. Furthermore, certain points along the blood vessel may be better suited to hemodynamic analysis (due, for example, to the existence of veins, cysts, or other components which potentially may interfere with the transmission/reflection of ultrasonic energy).

It is also noted that the term "A-mode" as used herein encompasses both traditional A-mode (i.e., display of amplitude versus depth (time) via repeatedly scanned lines) and other related modalities such as M-mode (i.e., grayscale image distributed over temporal dimension) and B-mode (i.e., "steered" grayscale image representative of depth (time) versus width), such alternate modalities being well known to those of ordinary skill in the ultrasound arts. Hence, it will be recognized that while the following discussion is cast in terms of traditional A-mode, the other associated modalities may be employed as well.

The A-mode ultrasonic energy of the present embodiment may also be used to complement the Doppler spectral modalities previously described herein, thereby providing both the system designer and ultimate end users of the apparatus with greatly enhanced flexibility in both design and operation. Specifically, in terms of modality space, at least three different operating schemes are contemplated by the present invention, including: (i) A-mode detection alone; (ii) Doppler-based detection alone; and (iii) a combination of the A-mode and Doppler modalities together. While not required, such use of complementary modalities as in (iii) may enhance the reliability and robustness of results obtained with the instrument.

Lumen Detection

Figure 20:
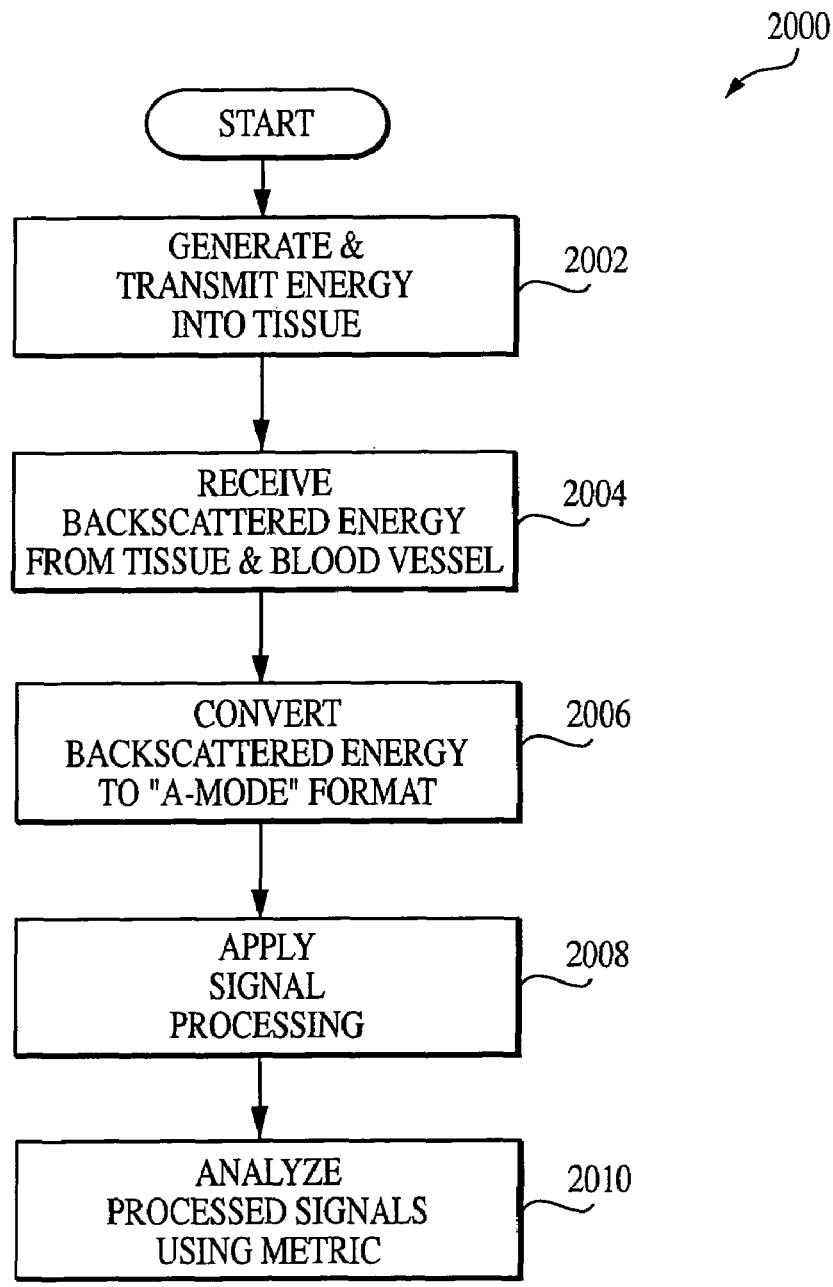
FIG. 20 is a logical flow diagram illustrating one exemplary embodiment of the method of locating a blood vessel using lumen detection according to the invention.

Referring now to FIG. 20, a first embodiment of the method of detecting a blood vessel within the tissue of a subject is described in detail. In the present context, the term "tissue" is meant to include all components present in the vicinity of the blood vessel being examined, including any interposed skin, musculature, tendons, veins. As shown in FIG. 20, the method 2000 comprises first generating and transmitting acoustic (e.g., ultrasonic) energy in the desired beam width into the tissue of the subject generally in the region of interest where the blood vessel is located (step 2002). For example, in the case of the radial artery, the ultrasonic transducer transmitting the waves can be physically or electronically "steered" laterally across the region of interest in a scan pattern so as to cut across at least a portion of the blood vessel with the ultrasonic beam. For example, an assembly which moves the ultrasonic transducer over the surface of the skin (such as the transverse positioning apparatus previously described herein) may be used. Alternatively, a larger dispersion beam may be used to obviate at least a portion of the scan function; the beam dispersion may be subsequently adjusted upon identification of the blood vessel or region of interest for better signal quality if desired. As yet another alternative, a phased-array or other electronically steerable device may be used to generate transmit/receive beams of comparatively narrow dispersion which scan the tissue without physical movement of the transducer element.

The tissue under examination may also be applanated as previously described to "pre-load" the tissue. Such pre-loading may be beneficial in the case where veins or other smaller blood vessels are interposed between the ultrasonic transducer and the blood vessel of interest, or generally in the vicinity thereof, such as in the case of the human radial artery. Specifically, controlled pre-loading preferentially collapses the smaller vein due to its smaller hoop stress and lower lumen (blood) pressure as compared to the artery, thereby effectively removing it from view of the lumen detection techniques described below. The Assignee hereof has determined that a pre-load applanation on the order of 30 mmHg is suitable in most cases to sufficiently collapse any veins interposed between the transducer and the radial bone, although it will be recognized that other values may be used depending on the specific application.

It will be recognized, however, that it may also be desirable to detect and locate other blood vessels such as the veins referred to above contemporaneously with the detection/location of the primary blood vessel of interest. Hence, the foregoing applanation may be used selectively as desired in order to "filter" what is viewed by the lumen detection apparatus. For example, if there is a high degree of clutter and other noise present in the A-mode signal for a given individual, it may be desirable to applanate the region under evaluation to remove the effects of energy backscatter from the vein(s) around the artery. Alternatively, if the noise level is sufficiently low, it may be desirable to detect the presence of the vein(s), such detection being potentially useful for determination of the tissue scaling or transfer function used in conjunction with non-invasive blood pressure measurements. Specifically, the presence of an interposed vein may affect the value of the transfer function somewhat, so it may be desirable to detect its presence and compensate for its effects.

Returning again to FIG. 20, backscattered energy reflected from the tissue, blood vessel and lumen contained in the region being scanned is next received by the same (or another) transducer element per step 2004, and converted by the processing within the apparatus to an A-mode or other desired modality in step 2006. Additional signal processing (described in greater detail below), including derivation of an "envelope-squared" value, is applied to the A-mode lines in step 2008 in order to enhance subsequent blood vessel detection. Lastly, in step 2010, the processed A-mode signals are further analyzed in terms of a predetermined metric or other criterion to identify the location within the region of interest where the blood vessel resides. In one variant, the metric is adapted to identify plateaus within the normalized integrated power profile resulting from the presence of the lumen within the blood vessel of interest. Hence, when a significant plateau in the integrated backscattered power is identified during the transverse "sweep", the lateral position of the transducer when the plateau is detected corresponds to the lateral position of the blood vessel. In another variant of the method 2000, the signal level of the envelope-squared parameter is analyzed to identify local minima, also resulting from the presence of the lumen.

Figure 20A:
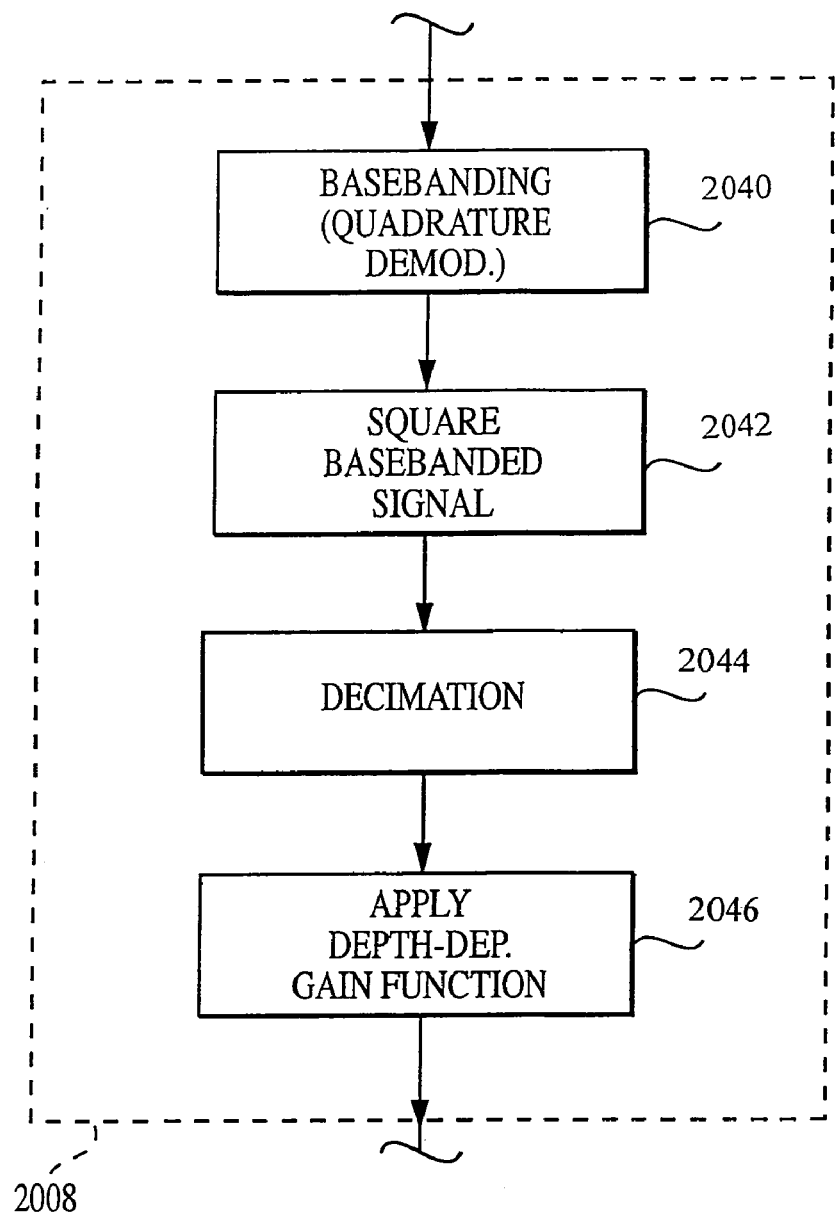
FIG. 20a is a logical block diagram illustrating one exemplary embodiment of the method of processing A-mode signals per the method of FIG. 20.

As shown in FIG. 20a, one embodiment of the signal processing (step 2008) associated with the basic A-mode lumen detection approach of FIG. 20 comprises basebanding (quadrature demodulation) the "raw" backscattered A-mode signal (step 2040), squaring the basebanded A-mode signal (step 2042), thereby producing the "envelope-squared" data, and decimation to a predetermined sampling rate (e.g. 2 MHz) per step 2044. The depth-dependent gain (e.g., TGC) is next applied to the envelope-squared data per step 2046 to adjust for propagation loss. These signal processing steps are described in greater detail in the following paragraphs.

Figure 21:
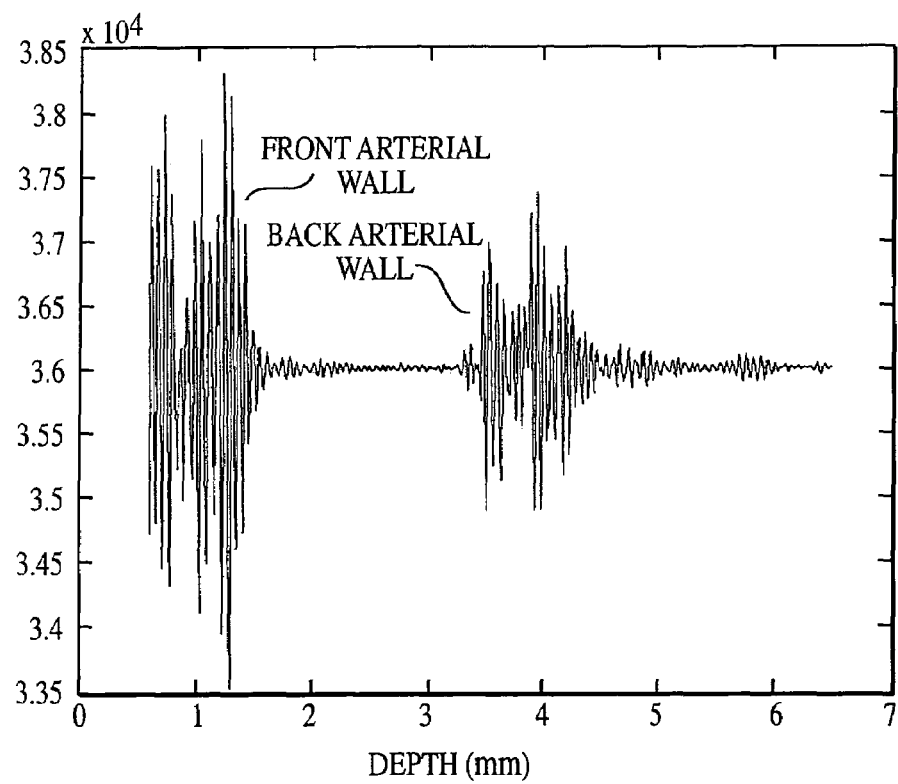
FIG. 21 is a graphical representation of a "raw" A-mode signal as a function of depth within the tissue of the subject being monitored.

FIG. 21 is a plot of the A-mode signal amplitude associated with the radial artery of a living subject, referred to as 'raw' A-mode data herein, versus time. It will be noted that the time axis of FIG. 21 has been converted to depth based on the propagation speed of the ultrasonic energy through the tissue. This conversion is performed since depth is considered a more readily interpreted quantity than time for the purposes of the invention, although it will be appreciated that time (or even other representations such as time-scale) may be used with equal success.

One important feature demonstrated in FIG. 21 is the level or amplitude of the A-mode signal as a function of depth. As illustrated in FIG. 21, there is an obvious range, from about 1.5 mm to 3.35 mm in this example, in which the signal level is quite low. This low signal amplitude is attributable to the low backscattering of energy associated with the blood (lumen) flowing the in blood vessel being located. Conversely, where no such blood vessel lies within the ensonified region of the tissue, no such reduction in signal level or backscattered power is identified. This is the primary feature used by the present embodiment for detecting the presence of the blood vessel.

Figure 22:
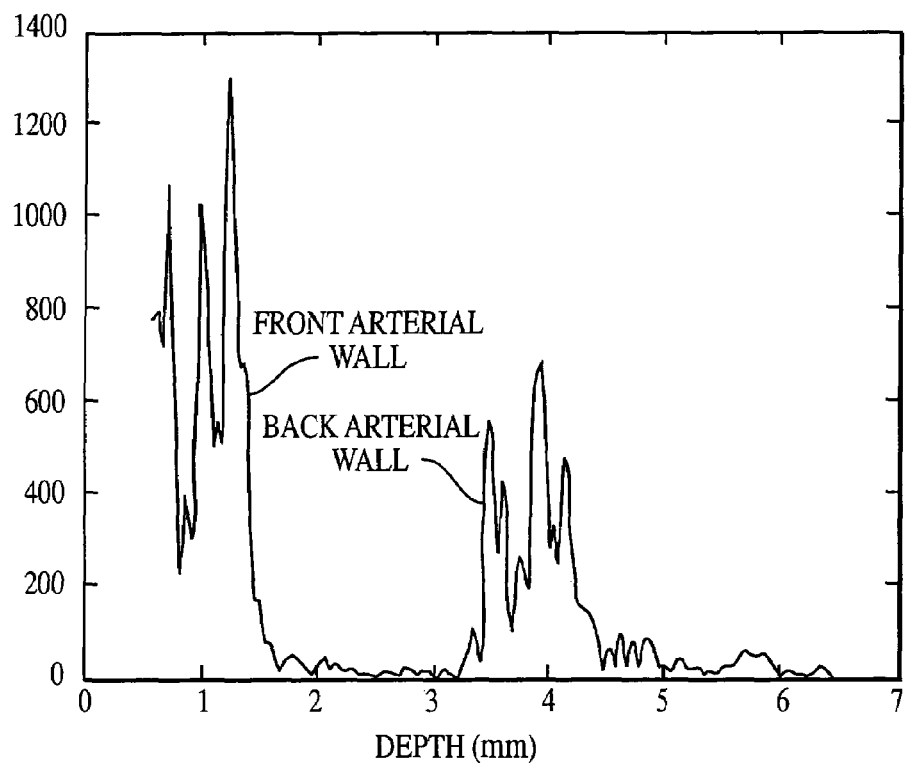
FIG. 22 is graphical representation of the envelope derived from the raw A-mode data of FIG. 21.

In addition, the 16 MHz center frequency used for this example is clearly depicted in FIG. 21. Since the center frequency conveys no information relevant to the location of the arterial walls, the first step of signal processing is to remove the center frequency. This process is denoted as quadrature demodulation (or envelope detection). The envelope detected signal associated with the exemplary A-mode signal of FIG. 21 is shown in FIG. 22.

Figure 23:
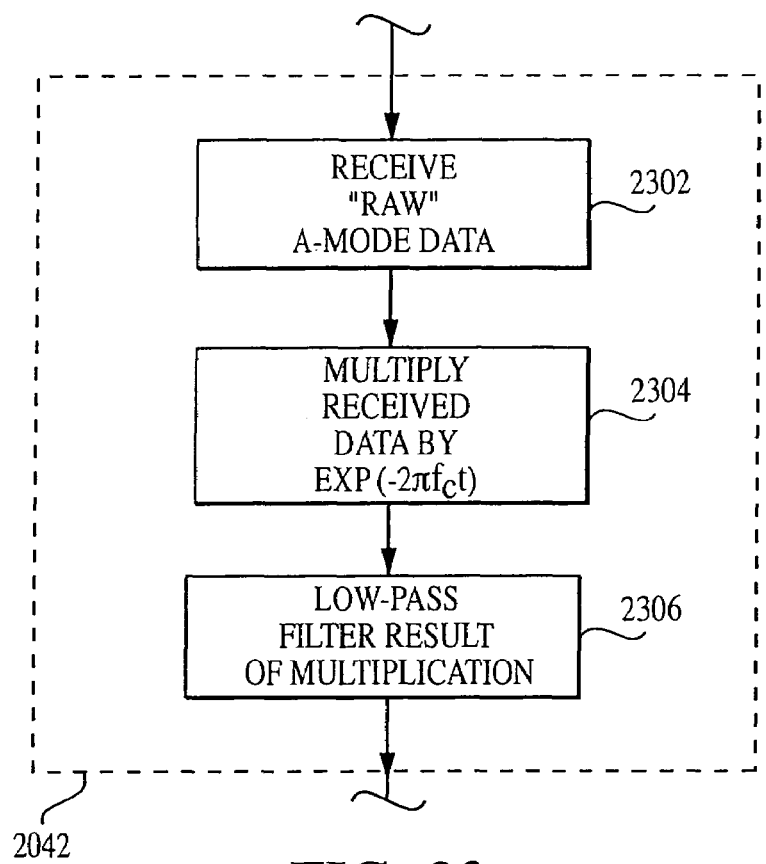
FIG. 23 is a logical flow diagram illustrating the general methodology of quadrature demodulation and A-mode signal filtering according to the invention.
Figure 24:
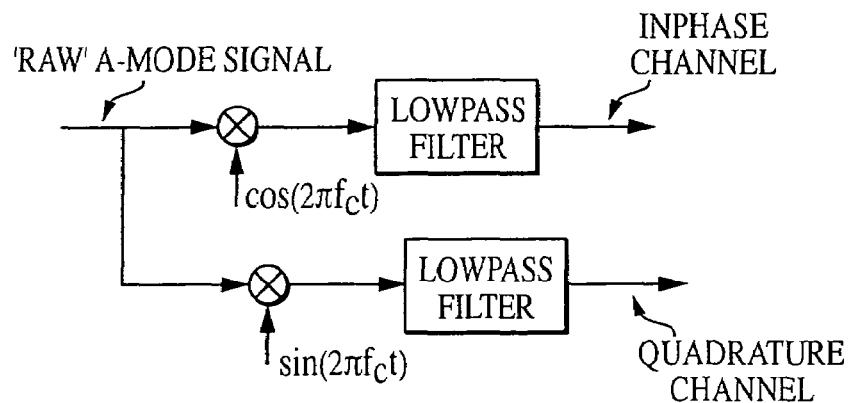
FIG. 24 is a block diagram illustrating the method of quadrature demodulation of the A-mode signal according to the present invention.

Quadrature demodulation as used in the present embodiment generally comprises multiplication of the A-mode signal by the sine and cosine functions, and lowpass filtering. The purpose of quadrature demodulation is to baseband the A-mode signal, through the removal of the transmit carrier frequency. This method is generally illustrated in FIG. 23. As shown in FIG. 23, quadrature demodulation consists receiving the backscattered "raw" A-mode signal (step. 2302) then multiplying of the received backscattered "raw" A-mode signal by the complex exponential, $\exp(-2\pi f_c t)$ where $f_c$ denotes the transmit center frequency of the signal (step 2304). This produces a series of values representing sum and difference frequencies of the complex exponential function and raw A-mode signal. Next, the resulting signal is lowpass filtered (step 2306) to retain only the difference (baseband) frequency components. Since the exponential function is complex, both an in-phase and quadrature channel are produced, designated I and Q, respectively. This process is also graphically depicted in FIG. 24.

In the illustrated embodiment, the frequency of the sinusoids is 16 MHz, corresponding to the center frequency, $f_c$, of the A-mode signal. The sampling interval of the sinusoids is equal to that of the digitized A-mode signal that is sampled at an effective rate of 64 MHz. Multiplication by the sine and cosine produces the following:

$$Y_{sin}(nT) = a(nT)\sin(2\pi f_c nT) \qquad \text{(Eqn. 15)}$$

$$Y_{cos}(nT) = a(nT)\cos(2\pi f_c nT) \qquad \text{(Eqn. 16)}$$

Where a(nT) denote the 'raw' A-mode signal with sampling interval $T=1/F_s$, and $F_s$ denotes the sample rate (e.g., 64 MHz). This multiplication is performed for the entire duration of the A-mode line. The in-phase and quadrature components, $X_I(nT_D)$ and $X_Q(nT_D)$ respectively, are produced by lowpass filtering $Y_{cos}(nT)$ and $Y_{sin}(nT)$. Here, $T_D$ denotes the decimated sampling interval.

Figure 25:
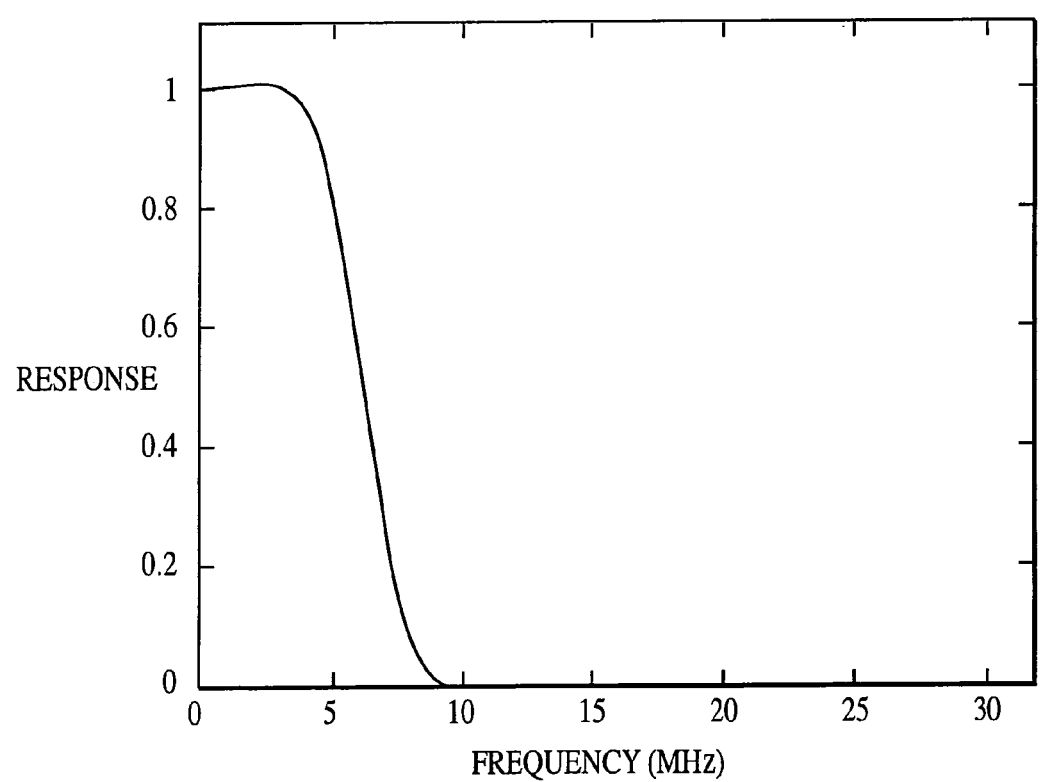
FIG. 25 is a graphical representation of the frequency response of one exemplary embodiment of the lowpass finite impulse response (FIR) filter of the present invention.

Lowpass filtering (step 2306 of FIG. 23) is accomplished in the illustrated embodiment with a finite impulse response (FIR) filter consisting of 37 coefficients. The filter is designed with a passband cutoff of 6 MHz corresponding to an A-mode transducer with 80% bandwidth. This provides for a decimation in sampling by a factor of four. That is, the filter output is produced at a rate of 16 MHz ($=T_D$). The frequency response is shown in FIG. 25. The coefficients associated with this exemplary low-pass design are shown in FIG. 26.

Note that for the illustrated case, the filter output advantageously need only be sampled at a rate of approximately 16 MHz in comparison with the original "raw" A-mode signal that is sampled at an effective rate of 64 MHz.

In the present embodiment of the invention, the magnitude of the complex envelope previously described is the only component required for subsequent processing, although other components of the processed or unprocessed A-mode signal may be used for other purposes if desired. Note that obtaining the magnitude of the complex envelope requires taking the square root of the sum of the squares of the lowpass filtered results. That is, since the result is complex, the magnitude equals the square root of the sum of the in-phase component squared and the quadrature component squared, as shown in Eqn. 17:

$$|E_{sq}(nT_D)| = \sqrt{X_I^2(nT_D) + X_Q^2(nT_D)} \quad \text{(Eqn. 17)}$$

Figure 27:
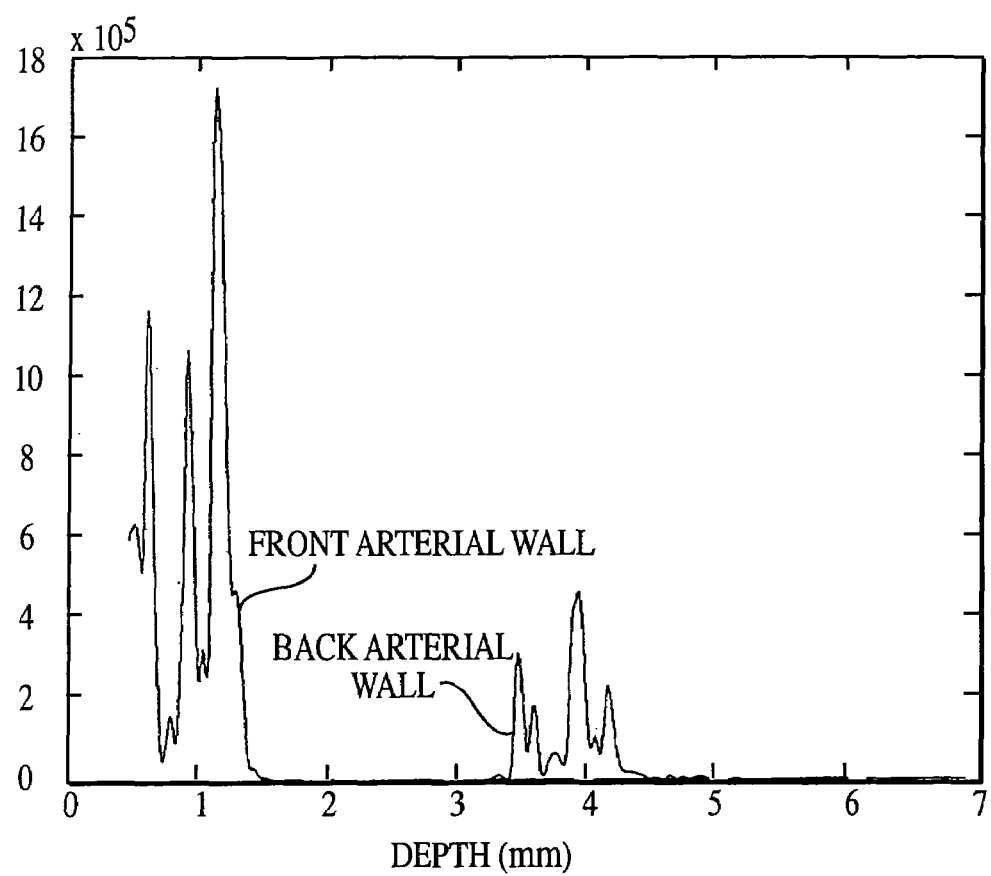
FIG. 27 is a graphical representation of the envelope-squared waveform derived from the A-mode signal of FIG. 21.

However, rather than calculate the magnitude of the envelope, the subsequent signal processing may be applied to the non-square-rooted signal, referred to herein as the "envelope-squared." This latter approach alleviates the need to perform the square root operation, thereby simplifying the resulting algorithmic implementation somewhat. The envelope-squared waveform is depicted in FIG. 27.

The envelope-squared, $E_{sq}(nT_D)$, is derived from the in-phase and quadrature components. This is computed as set forth in Eqn. 18:

$$E_{sq}(nT_D) = X_I^2(nT_D) + X_Q^2(nT_D) \quad \text{(Eqn. 18)}$$

Figure 28:
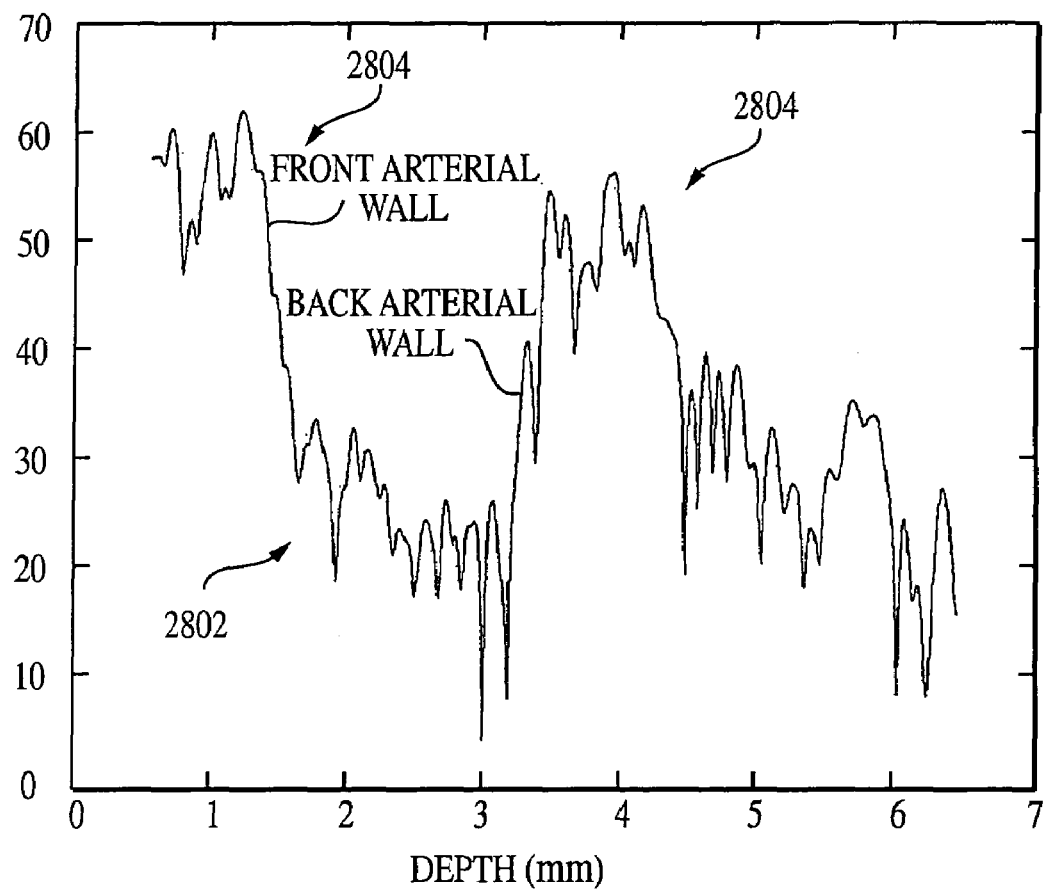
FIG. 28 is a graphical representation of the logarithm (base 10) of the envelope-squared waveform of FIG. 27.

In order to better assess the level of the signal associated with the lumen within the confines of the arterial walls, the logarithm (base 10) of the envelope-squared signal is obtained as shown in FIG. 28. Note that the level of the signal 2802 associated with the lumen is very roughly 30 dB below the signal 2804 associated with backscatter from the arterial walls.

It will be recognized, however, that in certain applications, "false" lumen detection might occur if the lumen detection methodology were based solely on the absolute value of the A-mode signal level. For example, lumen detection criterion based on the absolute signal level alone might erroneously detect lumen where there is none, or conversely miss lumen where it is actually present. Such false detections can arise from a variety of factors including, for example, backscatter and reflections from tissue (veins, musculature, etc) interposed between the transducer element and the blood vessel, movement of the subject during measurement, and the like. Hence, as described in greater detail below, the methodology of the present invention may be optionally modified to also examine signal artifacts proximate to those produced by the lumen in order to confirm the veracity of any given lumen detection, and positively locate both the lumen and contiguous vessel walls if desired.

A non-linear depth-dependent gain (step 2046 of FIG. 20a) is also applied to the envelope to account for the attenuation to the acoustic A-mode signal as it propagates through the skin, tissue and blood vessels. This depth-dependent gain is often referred to as Time Gain Compensation, or TGC; time and depth being implicitly related in this application as previously described. The expression for the gain is given by Eqn. 19 below:

$$\text{gain} = \text{depth} \quad \text{(Eqn. 19)}$$

Here the depth is assumed to be in millimeters, and the gain is applied to the envelope-squared. It will be recognized, however, that other gain functions may readily be applied either in place or in concert with that of Eqn. 19 above. Such gain functions may be empirically determined, such as through clinical testing, or determined via other means such as mathematical derivation or anecdotal or historical sampling of the A-mode signal or other parameters related thereto.

Figure 29:
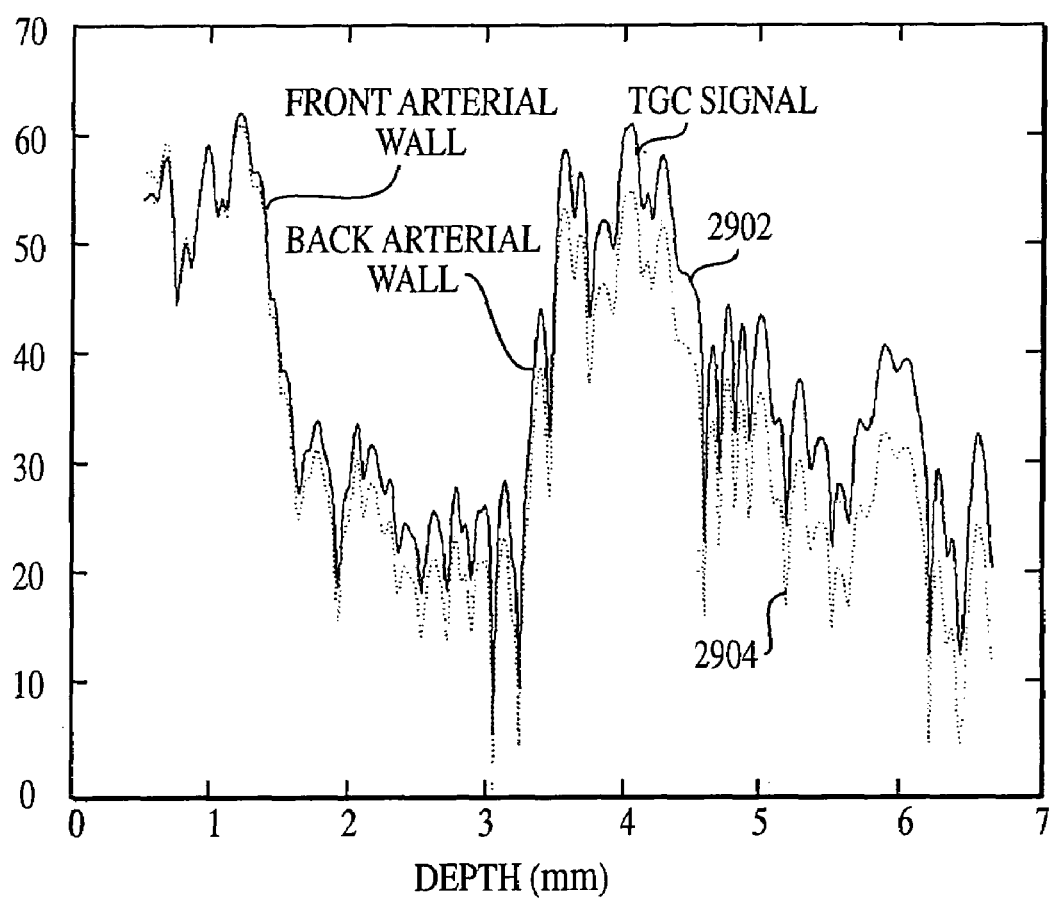
FIG. 29 is a graphical representation of the application of the gain function (TGC) to the envelope-squared of the A-mode signal of FIG. 27.

The application of the gain function to the envelope-squared of the A-mode signal is depicted in FIG. 29. Note that in FIG. 29, the solid curve 2902 corresponds to the A-mode signal with TGC applied, while the dashed curve 2904 corresponds to the A-mode signal without TGC.

It will further be recognized that while the foregoing discussion is cast in terms of signal processing including quadrature demodulation, envelope-squared calculation, and filtering, other types of signal processing and conditioning techniques may be employed consistent with the invention.

Figure 30A:
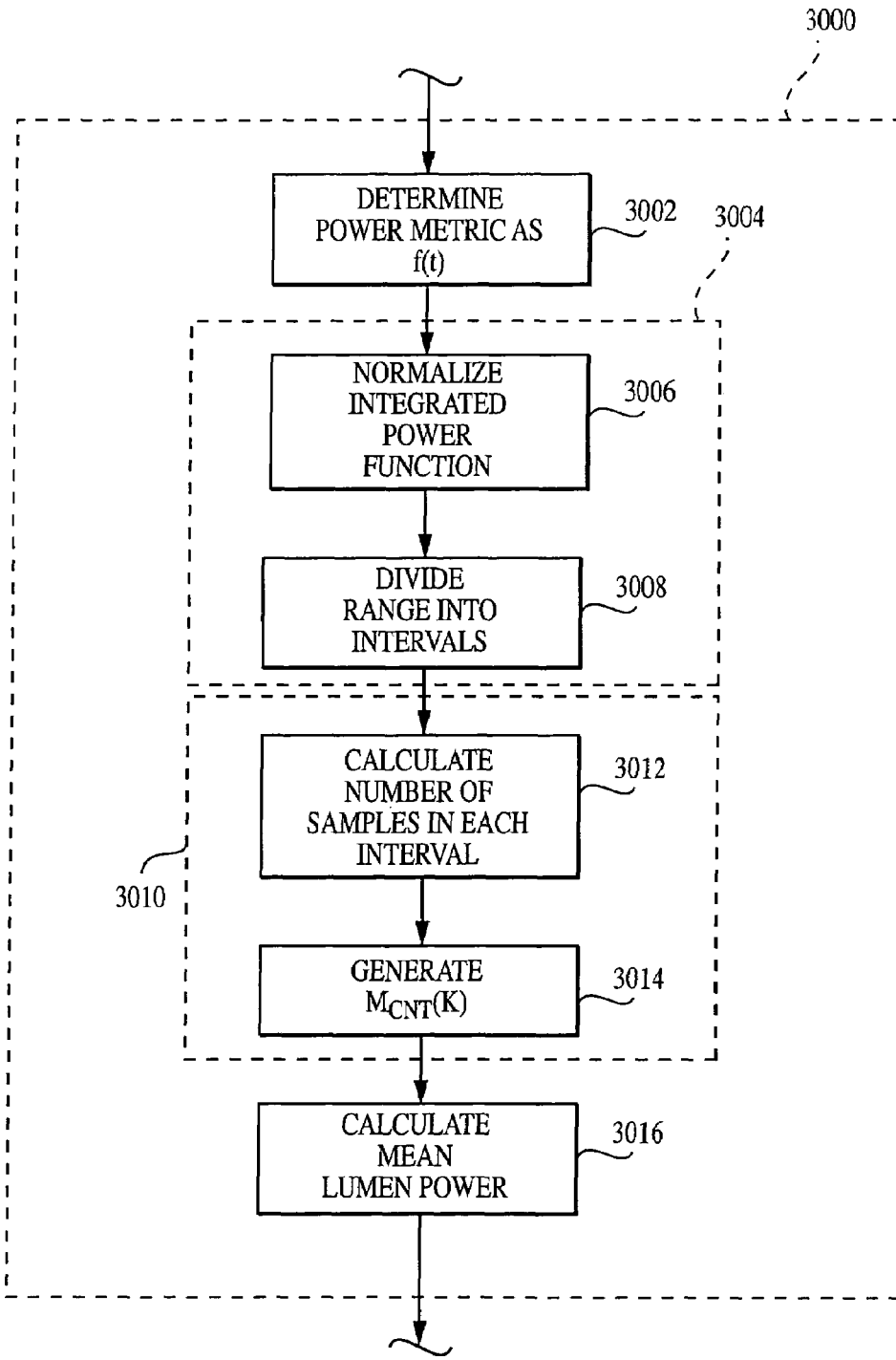
FIG. 30a is a logical flow diagram illustrating the "plateau" method of lumen detection according to the invention.
Figure 30B:
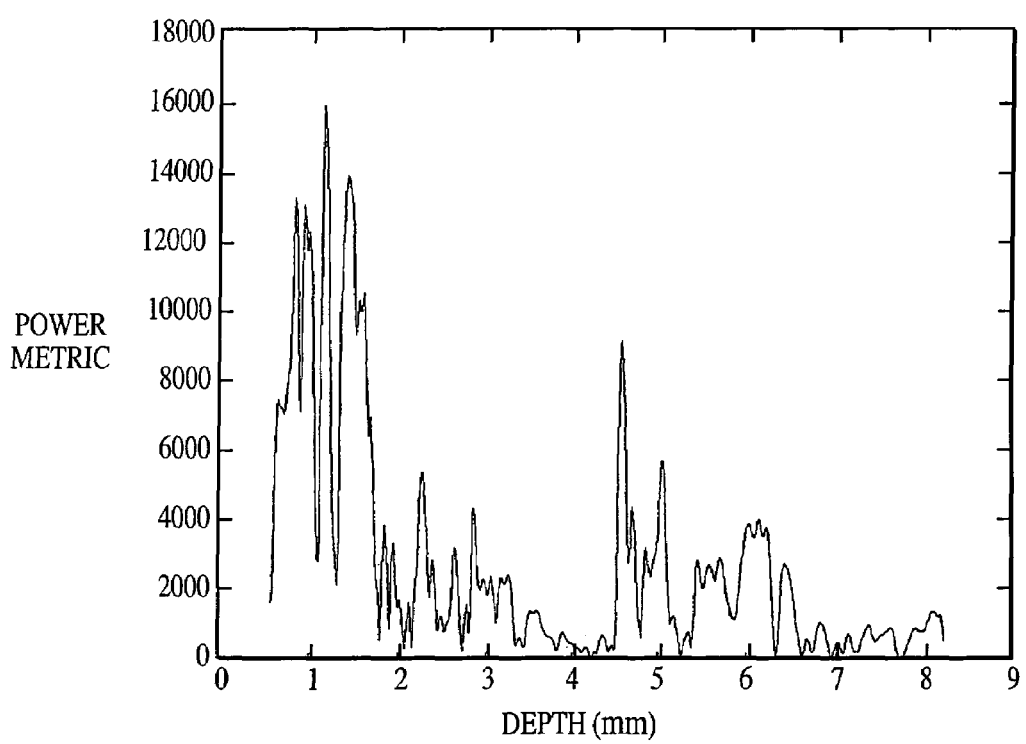
FIG. 30b is a plot illustrating measured backscattered power as a function of depth for a single A-mode line.

After completion of the signal processing, the next step 2010 of the method 2000 of FIG. 20 detects the lumen within the selected blood vessel (e.g., radial artery) for each A-mode line. In one exemplary embodiment, the lumen is detected in step 2010 according to the general methodology of FIG. 30a (hereinafter the "plateau" method). As illustrated in FIG. 30a, the plateau method 3000 of lumen detection generally comprises first determining a power metric as a function of depth (step 3002), the power metric being based on the aforementioned envelope-squared function. FIG. 30b illustrates backscattered power as a function of depth for a single A-mode line.

Figure 30C:
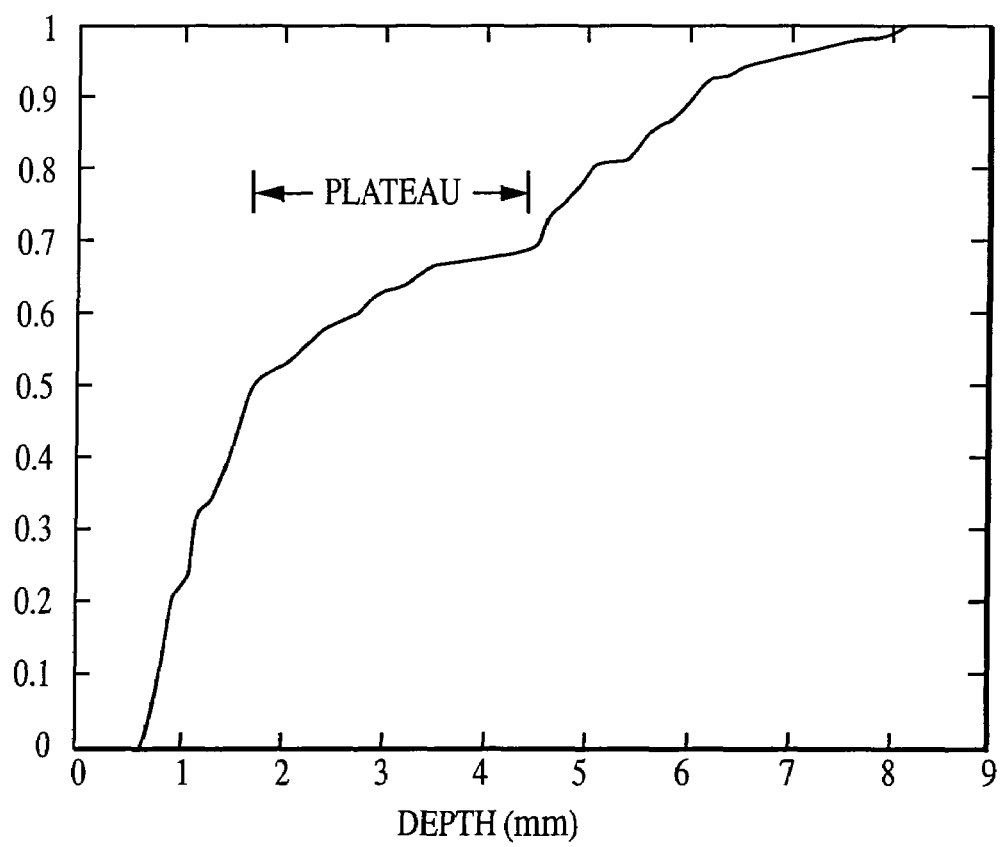

Next, the power metric is integrated according to Eqn. 20 below:

$$P_{int}(k) = P_{int}(k-1) + P(k) \quad \text{(Eqn. 20)}$$

where $P_{int}(k)$ denotes the power integrated up to the $k^{th}$ sample of the envelope-squared sequence, and $P(k)$ denotes the $k^{th}$ sample of the envelope-squared sequence. The second step 3004 of the plateau method 3000 consists of identifying the best estimate of the plateau associated with the weak backscatter from the blood within the lumen. As part of this step 3004, the integrated power function is first normalized to unity (step 3006), as is depicted in FIG. 30c. Next, in step 3008, the range from zero to unity is divided into a given number of intervals (e.g., eighty equal intervals in the present embodiment; that is, intervals of 0.0125 such that the first interval is 0 to 0.0125, the second from 0.0125 to 0.0250, and so forth). It will be recognized that other numbers of intervals and in fact, non-equal intervals (such as those determined by a function such as a logarithm) may be used as well if desired.

Figure 30D:
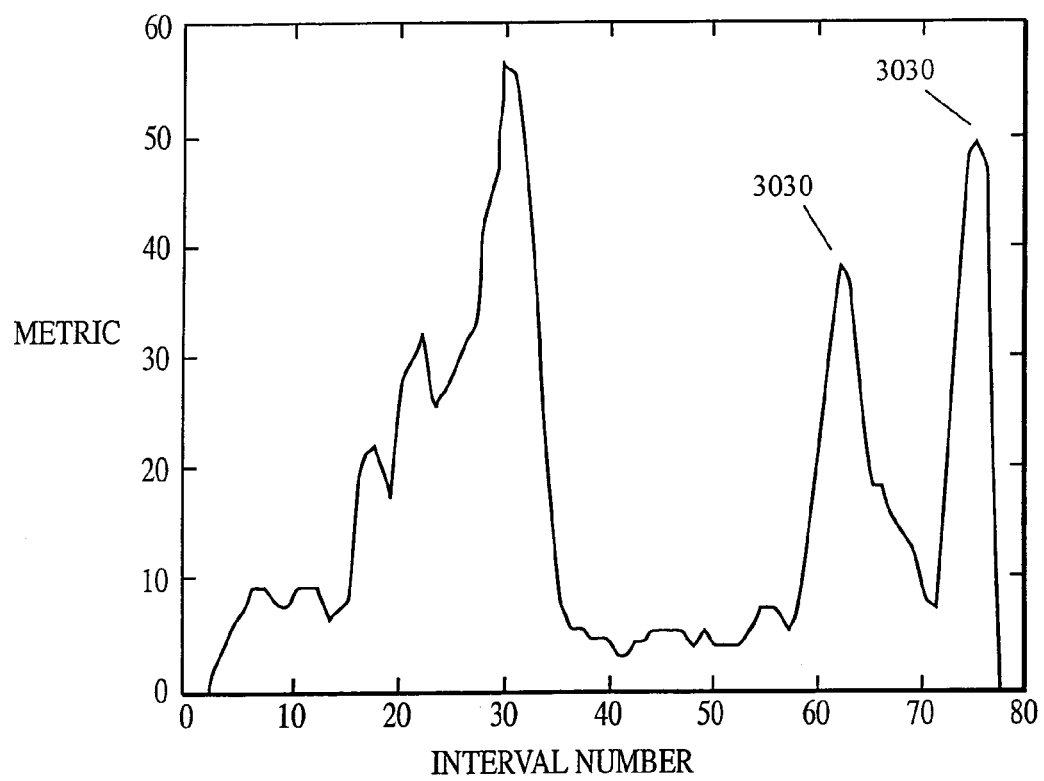

Next, the plateau is detected per step 3010. First, the number of samples occurring within each interval of normalized power is computed (step 3012). The rationale behind this computation is that when the power is low, corresponding to the backscatter from blood for example, many values must be integrated to cross from one integral to the next. Hence, an interval containing many samples is indicative of a plateau (and the lumen). In the illustrated embodiment of FIG. 30a, a test consisting of the number of points contained in three consecutive intervals is applied (step 3014), such that the metric is as shown in Eqn. 21 below:

$$M_{cnt}(k) = \sum_{n=k-2}^{k} m(n) \qquad \text{(Eqn. 21)}$$

where $M_{cnt}(k)$ denotes the sum of the counts in three consecutive intervals ending with the $k^{th}$ interval, and $m(n)$ denotes the number of samples in the $n^{th}$ interval. This metric is shown in FIG. 30d for A-mode line number 50 for a lateral sweep of the radial artery. Note the relatively large peaks 3030 in the intervals above interval number 60. These generally correspond to the low power occurring at deeper depths, which can often times result in false detection of the lumen.

An additional term was added to the foregoing metric to ensure that the plateau owing to low power towards the deeper depths does not trigger a false lumen detection. Specifically, the metric includes the requirement that the three consecutive intervals must be followed by an interval with a low count corresponding to the back arterial wall. Hence, the modified metric is given by Eqn. 22:

$$M_{cnt}(k) = \sum_{n=k-2}^{k} m(n) + \frac{1}{3}\sum_{n=k-2}^{k} m(n)\left(\frac{\frac{1}{3}\sum_{n=k-2}^{k} m(n)}{m(k+2)}\right)^2 \qquad \text{(Eqn. 22)}$$

Figure 30E:
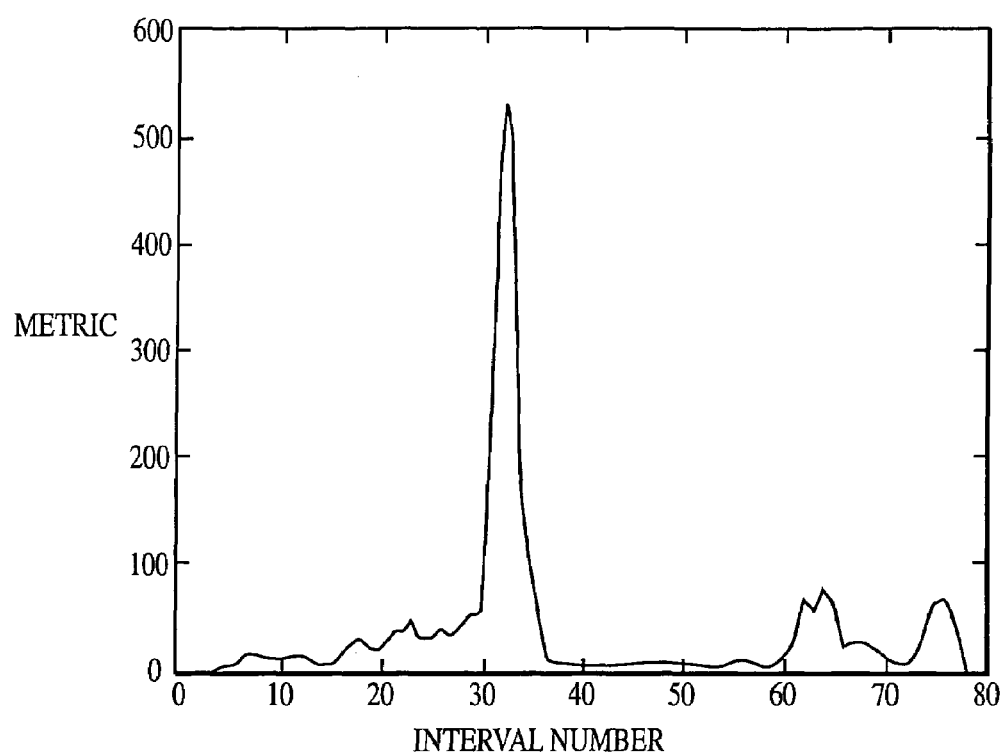
FIG. 30e is a graphical representation of the normalized plateau detection metric for a single A-mode line.

Note that the count, $m(k+2)$, two intervals ahead of the group of three consecutive intervals, is incorporated into Eqn. 22. A plot of this metric for a single A-mode line is shown in FIG. 30e for the normalized integrated power of the present example.

Detection of the peak results in the identification of the three consecutive intervals most likely to correspond to the lumen. The total count of samples in all intervals prior to the three intervals corresponding to the peak identifies the depth of the lumen.

In one exemplary embodiment, the sample point within the A-mode line associated with the lumen for the purpose of the subsequent arterial wall search (described below) is derived from the total number of samples in all intervals from the first interval up to (and including) the first interval in the three successive intervals. Hence, the sample associated with the lumen for the given A-mode line is estimated per Eqn. 23:

$$L = \sum_{k=1}^{K-2} m(k) \qquad \text{(Eqn. 23)}$$

where L denotes the number of samples prior to the lumen area, and K denotes the "pointer" to the third of the three consecutive intervals for which the peak was detected.

In addition, an estimate of the mean of the lumen power may be derived from the power contained in one or more of the three consecutive intervals (step 3016). For example, in one exemplary approach, mean lumen power is determined from the second of the three consecutive intervals by simply averaging the sample values of the envelope-squared that correspond to this interval. This estimate of the lumen back-scattered power may be used, for example, in conjunction with the estimated position of the detected lumen to detect the arterial walls, as described in greater detail below.

It is noted that in addition to arterial lumen, plateaus in the integrated power profile may result from other sources. Specifically, in the case of the human radial artery, such plateaus may also be induced by the presence of one or more veins located between the applanation device and the blood vessel of interest, or by the presence of cysts or other growths. While more common, plateaus due to veins are generally quite small in comparison to the "true" plateau of interest associated with compression of the radial artery, due largely to the comparatively smaller vein diameter (and wall thickness). As previously described, the methodology of the present invention effectively addresses this issue when required by conducting measurements of the tissue at applanation pressures above the level necessary to collapse the comparatively thin-walled veins. Such collapse of the veins generally occurs at pressures well below that necessary to significantly affect the diameter of the larger blood vessel (e.g., radial artery), thereby allowing for an elegant solution to the problem of potentially "false" plateaus due to veins.

In contrast to veins, cyst or growth-related artifacts generally occur only in a very small fraction of the population, and are frequently spatially localized to the extent that relocation of the transducer at another location over the artery will eliminate any effects resulting there from. Additionally, the cystic areas do not have corresponding pulse pressure or motion components related to pulse pressure, and hence can be readily identified and screened using any number of signal processing techniques well known to those of ordinary skill.

In a second embodiment, detection of the lumen in step 2010 of FIG. 20 is accomplished by computing the average power within a predetermined distance (e.g., 1 mm) interval along the A-mode line, hereinafter referred to as the "interval" method. The 1 mm interval corresponds to a time interval along the A-mode line of 1.33 usec, assuming the speed of propagation is 1500 met/sec and is derived from Eqn. 24:

$$D = ct/2 \qquad \text{(Eqn. 24)}$$

where:
D=depth,
c=speed of propagation,
t=time of propagation

The factor of 2 in Eqn. 24 accounts for bi-directional acoustic wave propagation. For a sampling rate of 16 MHz as previously described, 1.33 usec corresponds to approximately 22 samples along the de-sampled A-mode line.

The 1 mm interval for power calculation was selected in the illustrated embodiment based on the observation by the Assignee hereof that the diameter of the blood vessel under examination (e.g., radial artery) will exceed 1 mm in essentially all of the adult human population; hence, the power calculation is reasonably assured to constitute signal attributable only to the lumen. However, it will be recognized that this interval may be adjusted based on factors such as measurement of non-adult populations, use of other blood vessels, and/or use of the technique on other species. It is also noted that the 1 mm interval referenced above also advantageously provides a "reasonable" number of samples to average for an estimate of the A-mode signal power.

For a sampling rate of 16 MHz, the aforementioned 1 mm interval corresponds to a time interval of 1.33 usec, or approximately 22 samples. The estimate of power at time $nT_D$, $P_{1\,mm}(nT_D)$, is computed according to Eqn. 25:

$$P_{1mm}(nT_D) = \sum_{k=1}^{22} E_{sq}[(n - 11 + k)T_D]$$ (Eqn. 25)

Figure 31A:
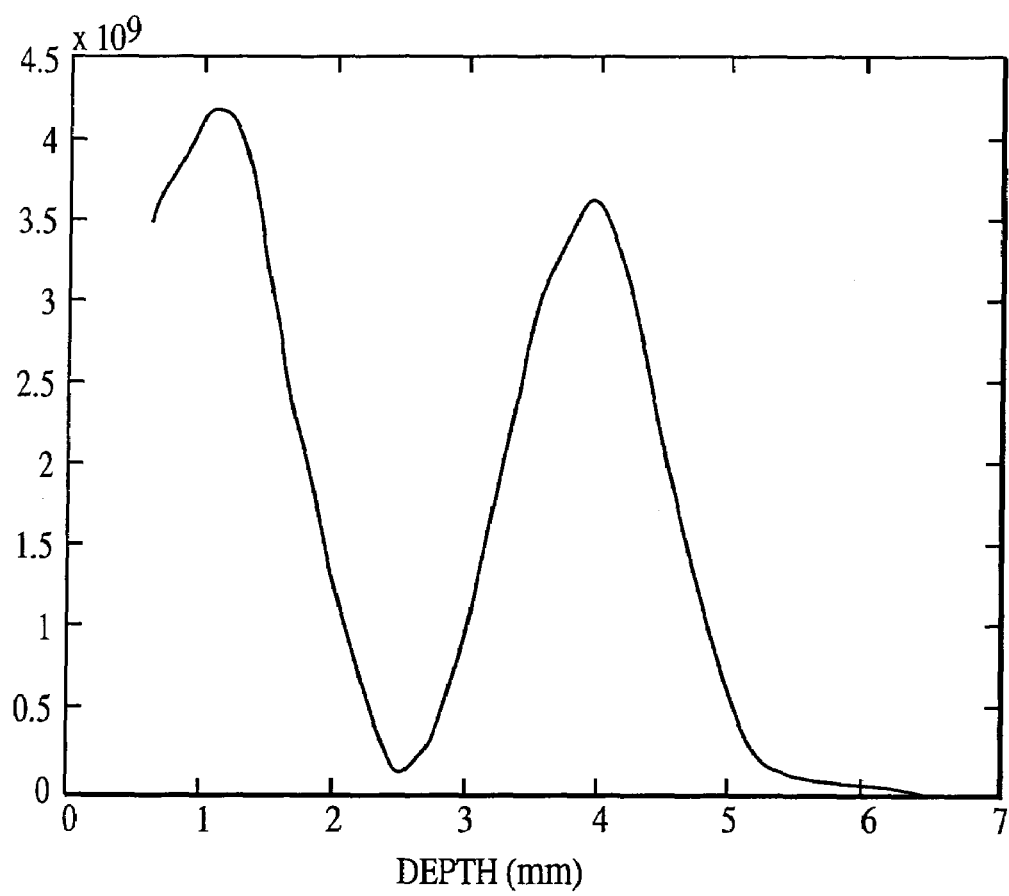
FIG. 31a is a graphical representation of the power profile (1 mm interval) along the TGC-corrected A-mode line of FIG. 29.

An exemplary plot of the acoustic power in a 1 mm interval along the line of TGC corrected A-mode data is depicted in FIG. 31a.

The location of the lumen (e.g., blood) within the confines of the radial artery is detected as the first minimum in the 1 mm average power calculation. The search for this minimum begins at a predetermined point along the A-mode line, (e.g. 1 mm), and continues to a second predetermined depth, chosen in the present illustration as 7 mm. This range of 1 mm to 7 mm was selected based on the observation that the front wall of the radial artery (i.e., that wall first encountered by the acoustic energy radiated from the transducer) will occur within this interval in essentially all of the adult human population. It will also be noted that the aforementioned minimum is clearly distinguishable in the plot of FIG. 31a, thereby advantageously allowing for ready detection in an A-mode signal of good quality (i.e., low noise level and other artifacts). The detection of minima within electronic signals may be accomplished by any number of techniques well known in the electronic arts, and accordingly is not described further herein.

Figure 31B:
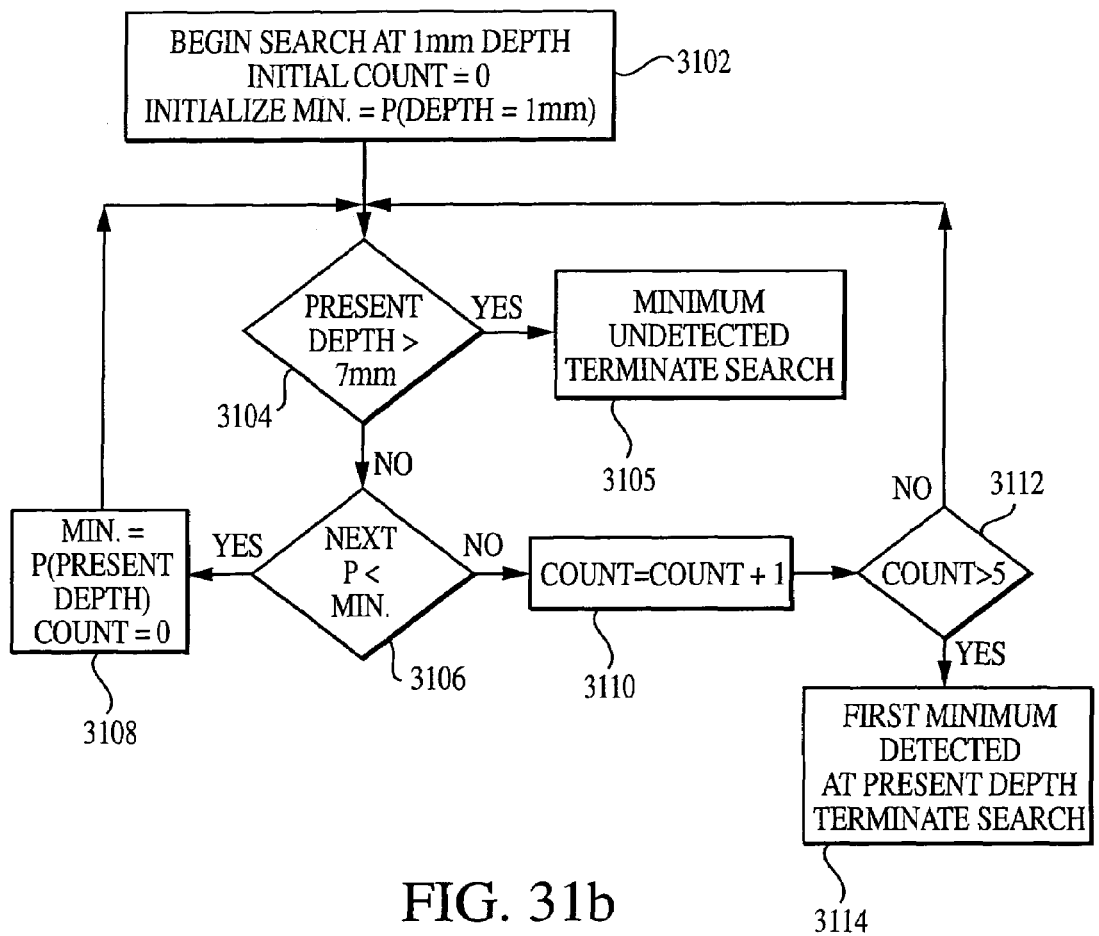
FIG. 31b is a logical flow chart illustrating the "interval" methodology of lumen detection using A-mode signals according to the invention.
Figure 31C:
FIG. 31c is a functional block diagram illustrating one exemplary embodiment of the methodology of FIG. 28b.

FIG. 31b graphically illustrates lumen detection using the aforementioned "interval" method. As illustrated in FIG. 31b, lumen detection comprises beginning the search for the artery wall at the pre-selected depth, 1 mm in the present case (step 3102). The minimum power is initialized at the power for depth=1 mm. Next, the relationship to the maximum specified depth (e.g., 7 mm in the foregoing example) is determined per step 3104. If the maximum depth has been exceeded, the minimum has not been detected, and the search is terminated (and optionally restarted) per step 3105. If the maximum specified depth has not been exceeded in step 3104, the next power sample is analyzed per step 3106. If less than the minimum value, the minimum is reset to the power level P associated with the sample of the current depth, and the count reset to zero (step 3108). Conversely, if the next power sample is not less than the current minimum, then the count is incremented by one (step 3110), and the integer number of the count analyzed (step 3112) to determine its relationship to a predetermined count limit parameter (e.g., 5 in the illustrated embodiment). If the current count exceeds the count limit parameter, the first minimum is assumed to have been detected at the current depth, and the search is terminated (step 3114). If not, steps 3104 through 3114 are repeated again as applicable. FIG. 31c further illustrates this process with respect to one exemplary signal processing architecture.

During the foregoing procedure, the level of the A-mode signal associated with backscatter from lumen, $E_{sq}$(blood), can be easily estimated once the region of lumen has been identified. The estimate is computed as a simple average over samples of the envelope-squared over a range centered at the depth for which lumen has been detected. The average is computed according to the exemplary relationship of Eqn. 26:

$$E_{sq}(\text{blood}) = \frac{1}{15}\sum_{k=1}^{15} E_{sq}[(N_{blood} - 7 + k)T_D]$$ (Eqn. 26)

where $N_{blood}$ denotes the index of the envelope squared corresponding to the depth of blood detection. Note that in Eqn. 26, the average is computed over fifteen samples of the envelope squared, although it will be recognized that other values may be substituted depending on the particular application.

Note also that the procedures of FIGS. 30a and 31b may be repeated as necessary for any number of spatially distributed scans; in this manner, "slices" of tissue may be examined in the depth (time) dimension sequentially (or even contemporaneously) in order to generate information regarding the lateral position of the blood vessel of interest as well the depth thereof. Such "slices" may also be electronically fused or combined to provide a multi-dimensional representation of the measured envelope-squared value (or integrated power, as described with respect to the previous embodiment) as is well known in the tomographic arts. The present invention further contemplates the use of multiple of such techniques for increasing the accuracy of the determination. For example, the techniques of "plateau" detection and "interval" detection may be combined to increase the robustness of the instrument.

Furthermore, it will be recognized that lumen (blood vessel) location information may be used to maintain the ultrasonic transducer or other measurement/treatment apparatus in any desired orientation with respect to the blood vessel; e.g., with a fixed lateral offset; with a lateral offset which is functionally related to the diameter of the blood vessel (as described below), etc. Similarly, the lumen detection information may be used to control the position of the transducer based on other parameters such as signal quality, the presence of cystic components or clutter, degree of applanation (if any), and the like.

Lumen and Wall Detection

Figure 32A:
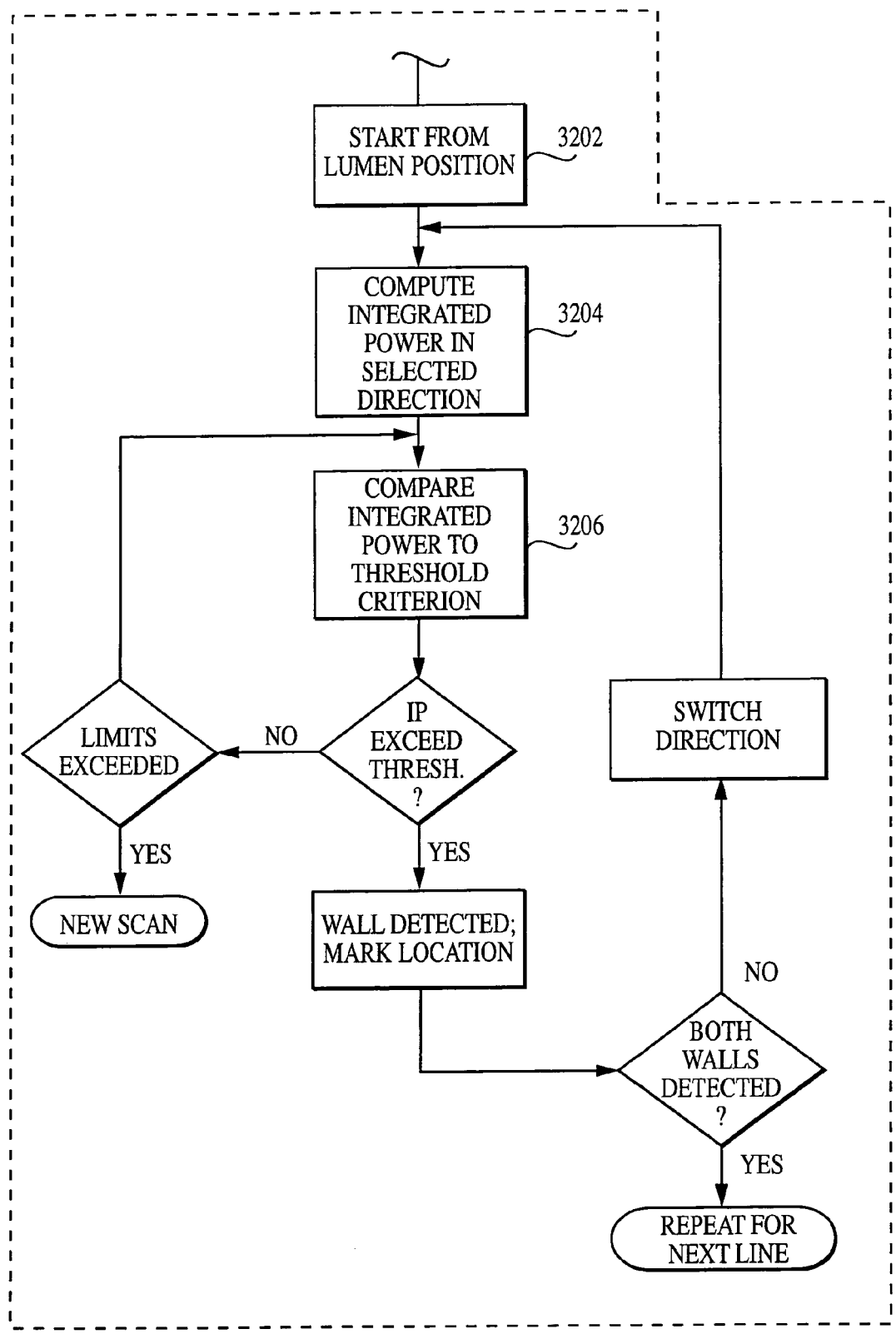
FIG. 32a is a logical flow chart illustrating a first exemplary methodology of front and back wall detection based on integrated power calculation.
Figure 32B:
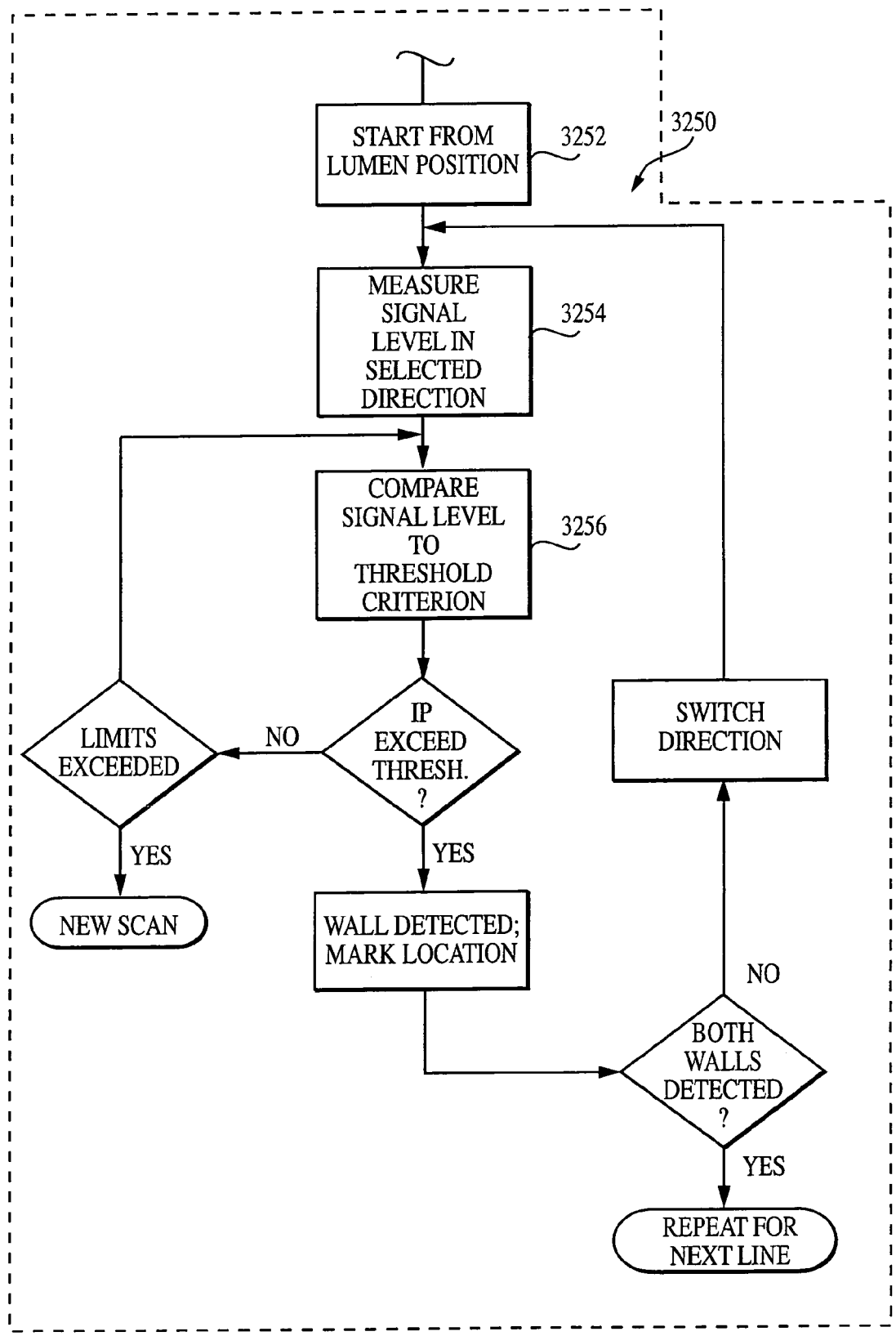
FIG. 32b is a logical flow chart illustrating a second exemplary methodology of front and back wall detection based on envelope-squared signal level determination.
Figure 33:
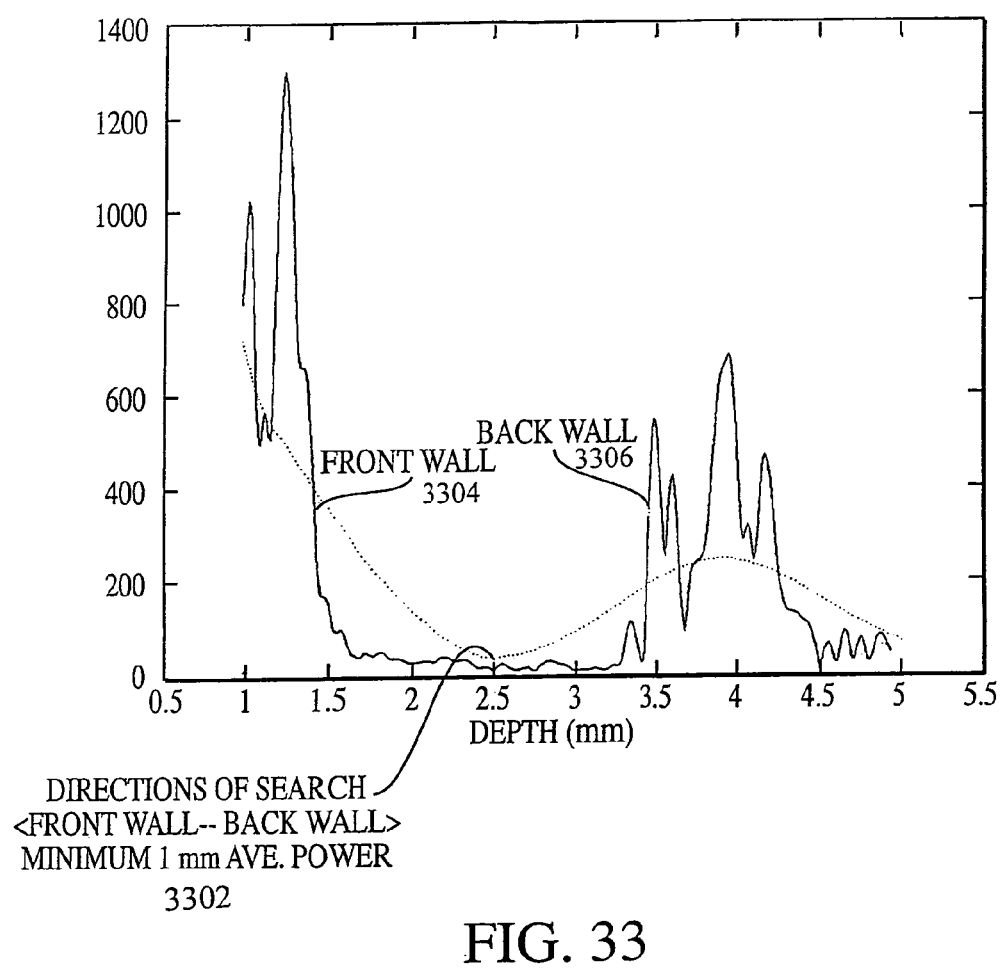
FIG. 33 is a graphical representation of the relationship between the average power calculation and the front and back wall artifacts present in the typical A-mode envelope according to the method of FIG. 32b.

Referring now to FIGS. 32a and 32b, an alternate embodiment of the method of detecting and locating a blood vessel within the tissue of a subject is disclosed. In this alternate embodiment, the foregoing techniques of lumen detection are used as a starting point for the analysis of the walls of the blood vessel of interest. Specifically, the backscattered energy associated with the front and back blood vessel walls is detected by searching forward and backward from the identified location of the lumen within the blood vessel. When the backscattered energy associated with the search in the backward direction (towards the transducer) satisfies one or more criteria, such as exceeding the mean lumen power or estimated level of the blood signal by a prescribed amount or factor (described below in greater detail), the front wall is detected and the location of the signal along the line is interpreted as the location of the front wall. Similarly, when the reflected energy associated with the search in the forward direction satisfies the relevant back wall criteria, the back wall is detected and the location of the signal along the line is interpreted as the location of the back wall. The front arterial wall is assumed to occur between the sensor unit and the depth of the detected lumen and in particular, generally in the vicinity where the A-mode signal is decreasing to the integrated power or signal level associated with the lumen. This assumption is founded on the knowledge that the lumen of the blood vessel is immediately adjacent the wall (i.e., on its far side with respect to the transducer). Similarly, the back arterial wall is assumed to occur at a depth greater than that of the lumen signal, and generally in the vicinity where the integrated power or signal level rises sharply above the level associated with the lumen. These changes in the A-mode integrated power or signal level corresponding to the front and back wall of the artery are readily observable, for example, in the TGC A-mode data.

Various methodologies for wall detection are now described in detail with respect to FIGS. 32a and 32b.

As used herein, the terms "front" and "back" infer no specific spatial orientation, but simply refer to the order in which the walls of the blood vessel are encountered during direct propagation by a moving ultrasonic wavefront emanated from an ultrasonic source. Hence, what may be the "front" wall when measuring hemodynamic properties in one transducer orientation may comprise the "rear" wall in another transducer orientation. Unique to the present invention is also the use of lumen detection as a means of front and back wall detection; i.e., due to the comparatively lower backscatter of ultrasonic energy by the lumen as compared to other blood vessel components, the position of the lumen may be readily identified from the backscattered energy, and the front and rear vessel walls identified relative thereto.

In a first exemplary embodiment (FIG. 32a), the method of wall detection utilizes (i) the detected position within the lumen from which to begin the search for the arterial walls, and (ii) the estimate of the mean lumen power from which to derive detection thresholds. The detected position of the lumen along the A-mode line serves as the start for the search for the back wall. Starting from this position (step 3202), the integrated power is computed by summing consecutive samples of the square of the envelope of the A-mode signal (step 3204). The formulation is given by Eqn. 27:

$$P_{bk}(m) = \sum_{k=K_{st}}^{m} P(k) \quad \text{(Eqn. 27)}$$

where $P_{bk}(m)$ denotes the integrated power in the direction of the back wall starting at sample $K_{st}$ up to sample m, and P(k) denotes the $k^{th}$ sample of the square of the envelope of the A-mode signal. When $P_{bk}(m)$ exceeds the prescribed threshold, the back wall is assumed detected and the corresponding sample value, m, denotes the depth of the back wall (step 3206). Note that the sample number along the A-mode line and depth are related; the actual depth is derived from the sample number as shown in Eqn 28:

$$D = cN_{samp}/2F_s \quad \text{(Eqn. 28)}$$

where c denotes the speed of propagation, $N_{samp}$ denotes the sample number, and $F_s$ denotes the sampling rate associated with the envelope-squared sequence.

The front wall is detected in much the same manner as the back wall. Starting from the same position used for the back wall, the integrated power is computed by summing consecutive samples of the square of the envelope of the A-mode signal in the direction of the front wall. Hence, the samples are taken in descending order from sample $K_{st}$. When the integrated power exceeds the prescribed threshold, the front wall is assumed detected and the corresponding sample value determines the depth of the front wall.

In the embodiment of FIG. 32a, a front wall threshold equal to 500 times the aforementioned lumen mean power, and a back wall threshold equal to 50 times the lumen mean power, are utilized. These values were determined empirically by the Assignee hereof with a specific depth-dependent gain (e.g., TGC) function. It will be recognized, however, that other threshold values and types of criteria may be used. For example, variable thresholds whose value varies as a function of other parameters (e.g., clutter in the lumen, or attenuation in interposed tissue) may be substituted. Furthermore, it will be recognized that the relationship between the front and back wall threshold criteria may or may not respect a predetermined relationship. For example, the front wall threshold may be determined as a function of the back wall threshold, or alternatively be completely independent there from. Other variations are possible; see for example the discussion of scoring and weighting below.

Furthermore, to facilitate the processing, inter-line averaging of the A-mode lines as is well known in the signal processing arts may be performed prior to lumen and wall detection. This technique can be used to improve performance and robustness of the system, both in terms of lumen detection and arterial wall depth estimation.

In an alternative embodiment of the method for detecting the arterial walls (FIG. 32b), the amplitude of the envelope squared, $E_{sq}(nT_D)$, is compared to the estimated signal level associated with backscatter from blood, $E_{sq}(blood)$. This is distinguished from the integral power calculation approach previously described. As before, the search for the front wall is in the direction towards the transducer element, that is, in the direction of decreasing depth. When the amplitude of the envelope-squared satisfies a designated criterion (e.g., exceeds four times the estimated signal level), this amplitude is attributed to backscatter from the front wall. The depth of this occurrence is designated to be the location of the front wall, subject to optional subsequent confirmatory processing, if desired. Note that alternatively (or simultaneously), criterion other than that relating to the amplitude of the envelope-squared variable may be employed.

The search for the back wall is performed in a similar manner to that described for the front wall. Specifically, the search begins at the depth of the detected lumen, but proceeds in the direction of increasing depth (i.e., away from the ultrasonic transducer). As with the front wall, when the amplitude of the envelope-squared exceeds satisfies a designated criterion, this amplitude is attributed to backscatter from the back wall. The depth of this occurrence is assumed to be the location of the back wall.

Accordingly, a simple search algorithm may be used in conjunction with the signal level (envelope-squared) methodology to identify the locations associated with the front and back arterial walls when the A-mode data is of "reasonable" quality. Specifically, as shown in FIG. 32b, the method 3250 comprises first comparing the A-mode signal level to the signal level of the lumen in both (i) the direction toward the transducer, and (ii) in the direction away from the transducer, starting at the depth where the lumen signal was detected (step 3252). The signal level is measured in the selected direction (step 3254); when the signal level is found to meet one or more predetermined criteria (e.g., the signal level of (i) or (ii) above being "n" times as great as the signal level associated with the lumen), the signal is assumed to correspond to the arterial wall (step 3256). The point along the A-mode line towards the transducer at which this criterion is met is denoted as the location of the front arterial wall, and similarly, the point along the A-mode line away from the transducer at which this criterion is met is denoted as the location of the back arterial wall. This is graphically depicted in FIG. 33, which illustrates the relationship between the average power calculation 3302 and the front and back wall artifacts 3304, 3306 present in the A-mode envelope.

Note that the processes of computing the envelope-squared, determining the corresponding average power in the designated interval (e.g., 1 mm) and the lumen signal, and detection of the front and back arterial walls, is performed in the present embodiment on an A-mode "line-by-line" basis.

Figure 34:
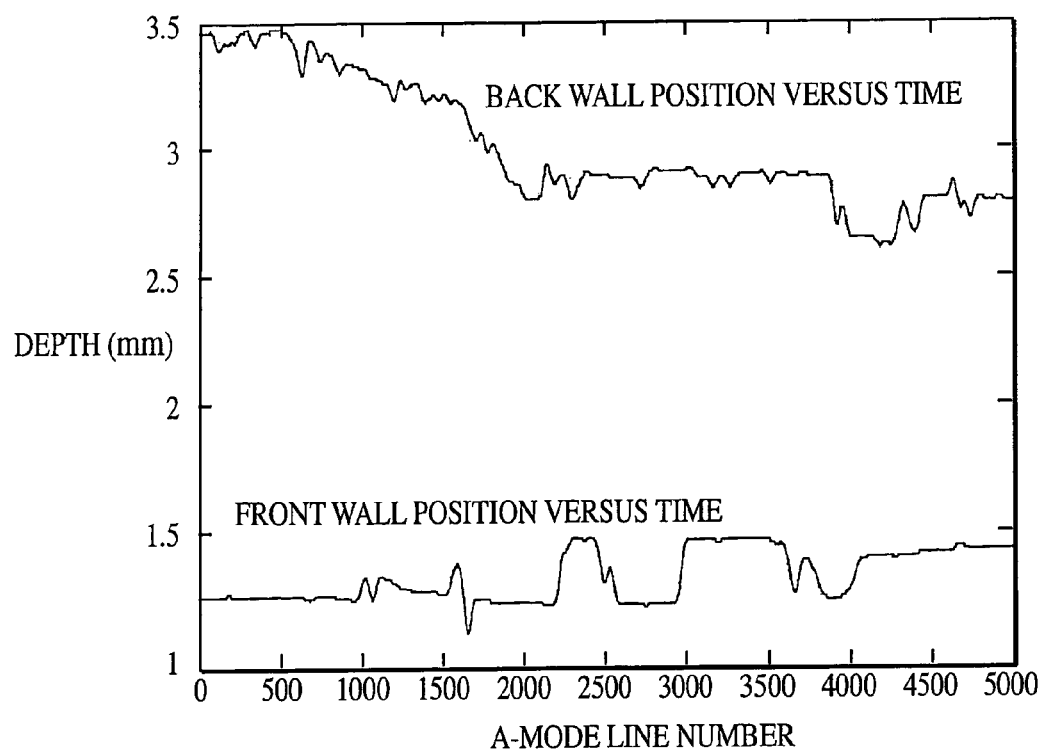
FIG. 34 is a graphical representation of the positions of the front and back walls of an exemplary blood vessel as a function of time (based on a sampling of 5000 A-mode signal lines) using the method of FIG. 32b.

The arterial wall positions determined in this manner for an exemplary A-mode data set consisting of 5000 lines is shown in FIG. 34. However, such line-by-line analysis may be substituted with other analytical approaches or increments, such as for example portions of a line, or groupings of multiple lines (whether contiguous or otherwise), or line averaging.

Once the relative wall positions are determined, the diameter of the blood vessel may be simply determined by taking the difference in depth between the rear and front walls. For example, if the rear wall occurs at a depth of 3.5 mm, and the front wall at a depth of 1.5 mm, the diameter of the blood vessel can be estimated at (3.5 mm−=1.5 mm)=2.0 mm. This determination is made in one embodiment using smoothed wall position estimates (i.e., those which are mathematically averaged of smoothed using other signal processing techniques) which are derived as previously described herein.

It will be appreciated however that due to a number of factors including the elasticity of the blood vessel walls, variations in output pressure of the cardiac muscle, and respiration, the effective diameter of a given blood vessel in a living subject will vary as a function of time. Hence, the foregoing wall detection methodologies must be adapted to account for these variation as a function of time. Consider, for example, the case where movement by the subject during measurement causes inadvertent repositioning of the ultrasonic transducer(s) with respect to the radial artery, such that the transducer is no longer situated directly "over" the artery. Under static conditions, such repositioning would be reflected as a reduction in measured blood vessel diameter, thereby inducing the control scheme for transducer position to attempt to relocate the transducer again to the optimal (i.e., maximal diameter) position over the artery. However, under normal "dynamic" conditions associated with a living subject, the diameter of the blood vessel will vary with no inadvertent movement or repositioning. Hence, the apparatus of the present invention is further adapted to compensate for transient or dynamic wall diameter effects using signal processing. Specifically, in one aspect, respiratory effects (which are comparatively low in frequency compared to cardiac rate) are electronically filtered. Similarly, cardiac effects (i.e., the natural expansion and contraction of the blood vessel due to changes in pressure within the blood vessel induced by the heart) are integrated or averaged out, thereby providing a wall diameter signal which is effectively independent of these effects. Specifically, in one exemplary embodiment, "raw" wall diameter measurements are integrated over several ("n") cardiac cycles before any control signal is generated to reposition the lateral transducer positioning assembly.

It will be appreciated that while the foregoing exemplary methodologies of wall detection (e.g., integrated power and envelope-squared signal level) are described in terms of both front and back walls of the blood vessel, either the front or back wall detection approaches may be applied to varying degrees. For example, if it is determined that for a certain subject being evaluated (or group of subjects having some common characteristic) that the front wall artifact is particularly weak or otherwise unreliable, back wall detection may be weighted more substantially in compensation. Similarly, if the clutter in the blood vessel under examination is significant, the more affected wall may be selectively de-emphasized in terms of weighting. Other such modifications may also be employed depending on the particular application.

Additionally, it will be recognized that the integrated power threshold and envelope-squared signal level approaches may be used either alone or in combination, or other methods (e.g., so-called "boxcar" averaging of the type well known in the signal processing arts) may be employed. For example, parallel computation of envelope-squared signal level and integrated power may be performed, and the calculated values compared to the applicable threshold criteria (e.g., 4 times lumen signal level, and 500 times mean lumen power, respectively). The results of these comparisons may then be used to determine the relative reliability or confidence in the wall detection, such as by calculation of a "confidence level" metric which can be subsequently used by system and/or user. If the wall detection scores for both the integrated power and envelope-squared approaches are high, the resulting confidence metric is high; if the wall detection scores for one technique is high and the other low, then the value of the confidence metric is reduced, and subsequent confirmatory processing is indicated.

Furthermore, it will be appreciated that in the context of wall detection as a whole, various forms of scoring or weighting known in the signal processing arts may be used in substitution for, or conjunction with, the aforementioned criteria. Such techniques advantageously increases the robustness of the system under actual clinical use. For example, in one alternative embodiment, A-mode signals having an envelope-squared or integrated power value meeting or exceeding a discrete value (e.g., 4 times estimated signal level in the case of signal level, or 500 times the mean lumen power in the case of the integration approach) are assigned a score of "1.0". Signals having a value less that this discrete value are assigned scores based on their relationship to a window function $w(x)$, such that values falling below a predetermined threshold (e.g., 2 times estimated signal level, or 250 times mean lumen) are given a score of 0.0, and values between the predetermined threshold and the designated criterion are assigned scores between 0.0 and 1.0 according to the function $w(x)$.

As yet another alternative, the envelope-squared or integrated power values associated with given A-mode measurement may be weighted based on some extrinsic or intrinsic "quality factor" which is related to the quality of data sampled during that interval. As a simple example, if the subject under evaluation moves during a given series of A-mode lines, the quality of data may be reduced, and accordingly any lumen/wall detection computations performed based on this data may be artificially reduced in weighting with respect to other samples.

As yet another alternative, "locational" weighting and/or scoring may be applied, such that envelope-squared or integrated power values generated by A-mode lines corresponding to certain depths may be adjusted. For example, as previously described, the likelihood of finding the front wall of the radial artery in an adult human less than 1 mm from the surface of the skin is exceedingly low; accordingly, an envelope-squared or integrated power value derived from the first "N" A-mode lines (corresponding to the depth of 1 mm) would be heavily de-valued or even eliminated (i.e., zero-weighted).

Similarly, interval-to-interval processing may be conducted such that wall artifact determined in non-contiguous A-mode line intervals is marked as an ambiguity requiring resolution. If a front wall artifact is detected in the first 1 mm depth interval, and again in the third, it can be assumed with some level of confidence that either (i) the wall artifact detected in the first interval is the front wall, and the artifact detected in the third interval is the back wall, or (ii) the first artifact was noise, and the third-interval artifact is the true front wall signal. Such ambiguity can be resolved through any number of techniques, such as the application of the aforementioned "locational" weighting to eliminate the first artifact based on low likelihood of occurrence in the adult population, or the use of sampling of subsequent A-mode signals for those intervals.

The present methodology also includes significant smoothing/filtering of the signal where needed. Such smoothing/filtering furthermore eliminates the time variations that occur from systole to diastole, as well as beat-to-beat variations caused by respiration. Such signal smoothing/filtering is generally well understood in the signal processing arts, and accordingly is not described further herein.

Figure 35:
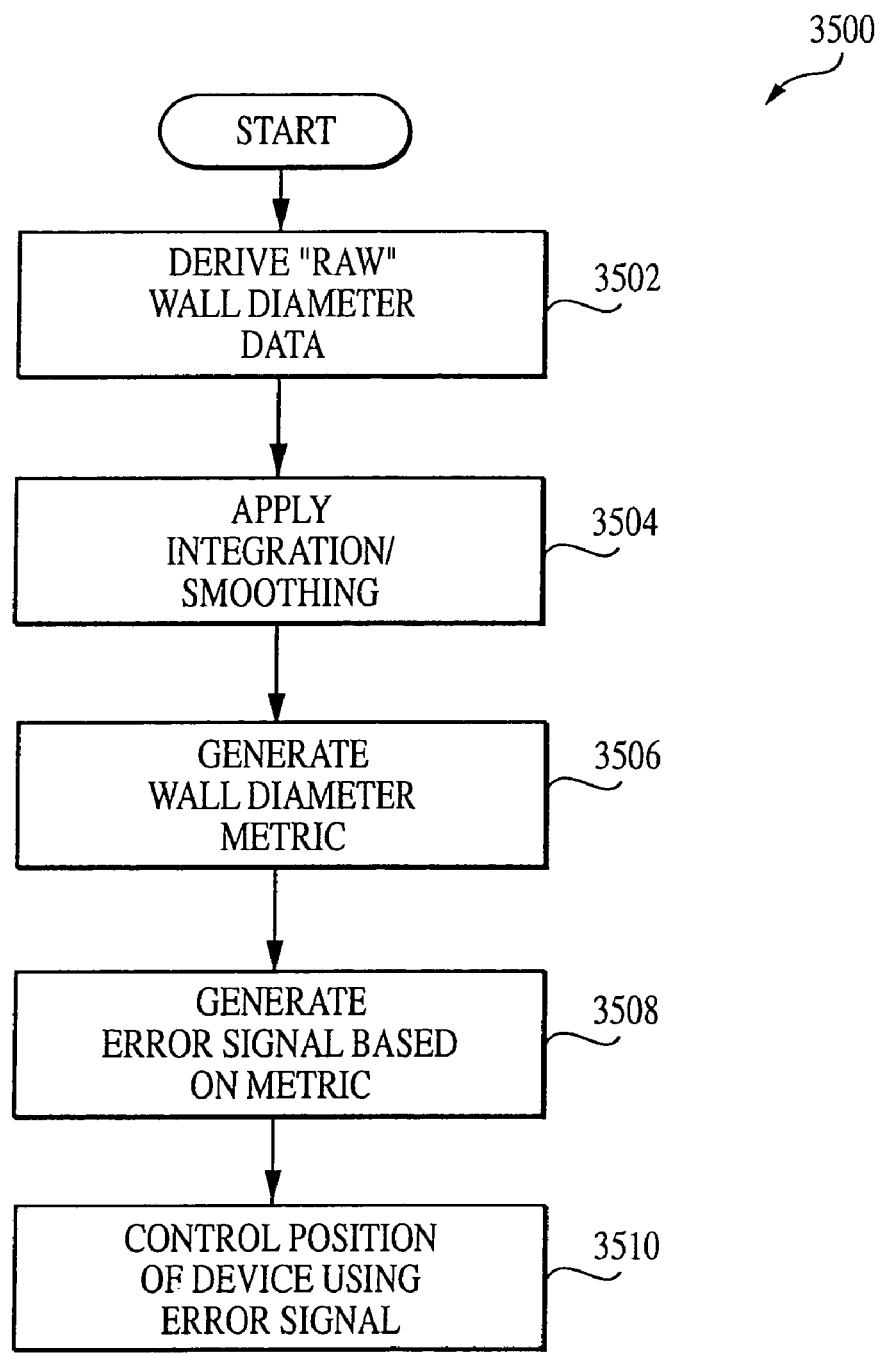
FIG. 35 is a logical flow diagram illustrating one exemplary embodiment of the method of locating a blood vessel using lumen and wall detection according to the invention.

Referring now to FIG. 35, one exemplary embodiment of the method of utilizing wall diameter information to position measurement or other treatment devices with respect to a blood vessel is described. It is noted that while the following discussion is cast in terms of a lateral positioning assembly (such as that previously described herein) used to reposition an ultrasonic transducer with respect to the radial artery of a human being, the general methodology may be readily adapted to other applications.

As shown in FIG. 35, the method 3500 generally comprises deriving "raw" wall diameter information which varies as a function of time (step 3502), as previously discussed herein. Next, in step 3504, the wall diameter information of step 3502 is integrated over a pre-selected finite time interval to "smooth" the raw data and eliminate most or all artifact relating to respiration and cardiac cycle. This produces a wall diameter metric (step 3506) which varies as a function of time. The wall diameter metric is then used to generate an error signal (step 3508) which is functionally related to the value of the absolute metric. This error signal is then fed to the aforementioned controller device which varies the lateral position of the transducer element (step 3510) so as to effectively maintain the magnitude of the error signal as small as possible (or alternatively, the value of the wall diameter metric as large as possible)

It will be recognized that the wall diameter information referenced above may be used as the basis for any number of different control schemes, including for example the fuzzy logic control approach previously described herein. Such variations and applications are well known to those of ordinary skill in the controller arts, and accordingly are not described further herein.

It is lastly noted that many variations of the methods described above may be utilized consistent with the present invention. Specifically, certain steps are optional and may be performed or deleted as desired. Similarly, other steps (such as additional data sampling, processing, filtration, calibration, or mathematical analysis for example) may be added to the foregoing embodiments. Additionally, the order of performance of certain steps may be permuted, or performed in parallel (or series) if desired. Hence, the foregoing embodiments are merely illustrative of the broader methods of the invention disclosed herein.

While the above detailed description has shown, described, and pointed out novel features of the invention as applied to various embodiments, it will be understood that various omissions, substitutions, and changes in the form and details of the device or process illustrated may be made by those skilled in the art without departing from the spirit of the invention. The foregoing description is of the best mode presently contemplated of carrying out the invention. This description is in no way meant to be limiting, but rather should be taken as illustrative of the general principles of the invention. The scope of the invention should be determined with reference to the claims.

APPENDIX A

Algorithm Experiments

To demonstrate the maximum time-frequency principle, 10 learning data files were selected from past applanation sweeps that possessed high quality ultrasound, overcompression, and generally large mean arterial pressure (MAP) difference. MAP difference was calculated by comparing estimated MAP to the average of two cuff MAPs measured immediately before and after an applanation sweep. Two additional files were acquired with an additional constraint of sweeping down to a minimum diastolic value less than 30 mm Hg below the true diastole (specifically files 11 and 12). The data files were acquired using a variety of sensor geometries, position angles (steel mount angles are varied and unknown), and subjects, as illustrated in Table 1.

TABLE 1

Learning Data

| File | Subject | Sensor | Sensor Position | Mean Cuff Avg. Pressure (mm hg) | Arterial Max Pulsatile Estimate (mm Hg) | Time-Frequency Estimate (mm Hg) |
|---|---|---|---|---|---|---|
| 1 | 1 | mo30 | steel mount | 108 | 122 | 103 |
| 2 | 2 | mo30 | steel mount | 88 | 90 | 82 |
| 3 | 3 | mo30 | steel mount | 68 | 85 | 84 |
| 4 | 4 | mo30 | steel mount | 88 | 83 | 83 |
| 5 | 4 | dc22 | 0° pitch, 0° roll | 85 | 90 | 86 |
| 6 | 5 | dc22 | −10° pitch, +10° roll | 63 | 51 | 58 |
| 7 | 2 | dc22 | −10° pitch, −10° roll | 84 | 90 | 92 |
| 8 | 6 | dc29 | 0° pitch, 0° roll | 77 | 104 | 105 |
| 9 | 7 | dc29 | +10° pitch, −10° roll | 88 | 107 | 81 |
| 10 | 8 | Mo30 | steel mount | 98 | 135 | 105 |
| 11 | 6 | Dc33 | 0° pitch, 0° roll | 82 | 124 | 87 |
| 12 | 3 | Dc19 | 0° pitch, 0° roll | 73 | 102 | 71 |
| | | | MAP error (mm Hg): | | 15 ± 17 | 3 ± 11 |

In each file, MAP was estimated by searching for the maximal pulsatile pressure. MAP was also estimated by determining the MAP associated with a pressure waveform with the maximal mean time-frequency distribution. The Pseudo Wigner distribution of the velocity, with k=0, calculated. Within each pressure waveform time interval, the mean distribution value was then calculated. The algorithm for calculating the maximal time-frequency distribution was "tuned" to the 12 files. By tuning, secondary algorithm steps such as the determination of the choice of the first pressure and velocity waveforms to be analyzed within a sweep were optimized. Also, the MAP differences using the maximum mean distribution versus maximum diastolic distribution were evaluated. While the results from both methods were insignificantly different, the maximum mean distribution was easier to calculate.

Once the mean time-frequency algorithm was tuned, the MAP in 6 new data files (again, with various sensor geometries, position angles, and subjects; see Table 2) was estimated and compared to the cuff MAP. For each comparison, the mean and standard deviation of the MAP difference was calculated. The paired, two-sided t test was used to assess significant differences between methods, using a 95% confidence interval.

TABLE 2

Testing Data

| File | Subject | Sensor | Sensor Position | Mean Cuff Avg. Pressure (mm Hg) | Arterial Max Pulsatile Estimate (mm Hg) | Time-Frequency Estimate (mm Hg) |
|---|---|---|---|---|---|---|
| 13 | 9 | Mo30 | steel mount | 73 | 93 | 73 |
| 14 | 4 | Dc18 | 0° pitch, 0° roll | 79 | 97 | 89 |
| 15 | 8 | Mo30 | steel mount | 88 | 114 | 95 |
| 16 | 2 | Mo30 | steel mount | 88 | 101 | 85 |
| 17 | 5 | Dc22 | +10° pitch, −10° roll | 64 | 60 | 64 |
| 18 | 2 | Dc33 | +10° pitch, −10° roll | 79 | 120 | 85 |
| | | | MAP error (mm Hg): | | 19 ± 15 | 3 ± 5 |

Results

For the learning data (Table 1), the maximum pulsatile MAP difference was 15±17 mm Hg; the maximum time-frequency MAP difference was 3±11 mm Hg. For the testing data (Table 2), the maximum pulsatile MAP difference was 19±15 mm Hg; the maximum time-frequency MAP difference was 3±5 mm Hg. In both the learning and testing data sets, the results obtained from the maximum time-frequency method were significantly different from those obtained using the maximum pulsatile method ($p \leq 0.02$ and $p \leq 0.03$, respectively).

APPENDIX B

Mechanical Impulse Response

In obtaining experimental verification of the methods disclosed herein, Applicant obtained data in 10 second intervals from three different human subjects in a hospital operating room. During these 10 second intervals, data was sampled at 400 Hz, and decimated to 100 Hz. The mean arterial pressures (MAPs) measured for each of the three subjects were 73, 126, and 83 mm Hg, respectively. These means were subtracted from the respective data sets for each subject, and fit to the ARX model using various combinations of N and M, as illustrated in Table B-1:

TABLE B-1

Combinations of Model Orders (N) and Number of Feedforward Coefficients (M)

| N | M |
|---|---|
| 4 | 3 |
| 10 | 9 |
| 2 | 1 |
| 1 | 1 |
| 0 | 1 |

For all three subjects, the optimum model was a zeroeth order model with one feedforward coefficient. The identified feedforward coefficients and their associated standards of deviation are shown in Table B-2.

TABLE B-2

Identified Feedforward Coefficients

| Subject | Mean (mm Hg) | $b_0$ | Standard Deviation |
|---|---|---|---|
| 1 | 77 | 0.75 | 0.003 |
| 2 | 121 | 0.86 | 0.001 |
| 3 | 81 | 0.80 | 0.003 |

Estimate of Diastolic Pressure

Using the time-frequency algorithm for estimating catheter MAP (such as that described with respect to FIGS. 3a and 3b herein) in conjunction with the wavelet algorithm for estimating catheter diastolic pressure (FIG. 16 herein), pressures were estimated in 156 decreasing applanation sweeps experimentally obtained from 7 human subjects in a hospital operating room. The applanation sweeps were obtained during conditions having a variety of prevailing catheter MAP values, ranging from 48 to 132 mm Hg. A prototype ultrasound circuit having comparatively low sensitivity was used during these experiments. Estimated and catheter pressures were compared, with the mean error in MAP being 2±15 mm Hg, and the mean error in diastolic pressure being 5±14 mm Hg. The reported catheter pressure was averaged from the first, middle, and last waveforms obtained during a decreasing applanation sweep. Using one prior art tonometry approach of estimating the MAP when the peak-to-peak pressure was maximum (i.e., the maximum pulsatile method), the mean error in MAP was 11±20 mm Hg. The squared correlation coefficients, $r^2$, for these estimates were 0.67 (p=0.030), 0.56 (p=0.038), and 0.61 (p=0.034), respectively. These three estimates (i.e., MAP, estimated diastole, and maximum pulsatile) are plotted as functions of catheter pressures in FIGS. B-1, B-2, and B-3, respectively.

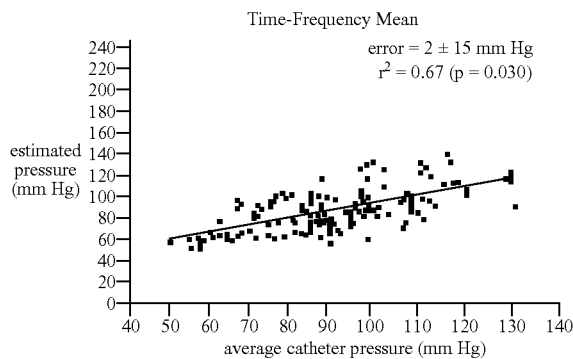

FIG. B-1. Time-Frequency Estimated MAP Versus Average Catheter MAP

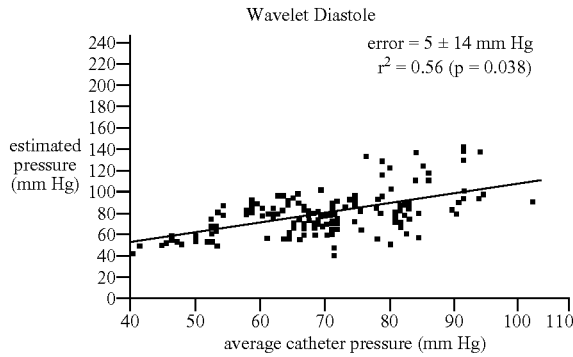

FIG. B-2. Wavelet Estimated Diastole Versus Average Catheter Diastole

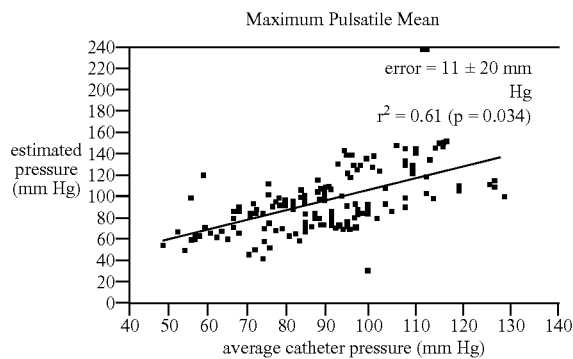

FIG. B-3. Maximum Pulsatile Estimated MAP Versus Average Catheter MAP

While the squared correlation coefficients for all three methods were significant, thereby indicating that approximately 60% of the variance in the estimates may be attributed to variation in catheter pressures, only the time-frequency and wavelet approaches resulted in low mean errors. It is believed that the standard deviation values observed for these errors are in part a reflection of the low sensitivity in the prototype ultrasound circuit.

APPENDIX C

When the ultrasonic/pressure sensor is positioned with respect to the subject's blood vessel to measure a pressure equivalent to the catheter mean, the end-diastolic velocity is maximized. In the controller example illustrated in FIGS. 17-19 herein, the catheter MAP dropped dramatically over 11 minutes. The maximum catheter MAP was 132 mm Hg; the minimum catheter MAP was 79 mm Hg. Over 552 beats, the mean error of the controller, compared to catheter MAP pressure, was 3±4 mm Hg. As shown in the 20 second snapshot that occurred at 6.5 minutes, (FIG. 19), a significant drop in the end-diastolic velocity was corrected within 5 beats.

Preliminary studies have been conducted by the Applicant herein to assess the accuracy of the fuzzy logic controller. Over a two hour period, two anesthetized operating room subjects were subjected to continuous two 20 minute intervals of measurement, followed by 5 minute intervals of rest. During each 20 minute measurement, an applanation pressure sweep was conducted, followed by continuous servo control. The catheter MAPs ranged from 69 to 106 mm Hg. Over 3,103 beats, the mean error of the controller MAPs, compared to catheter MAPs, was −3±5 mm Hg. Individual data sets are summarized in Table C-1 below.

TABLE C-1

Preliminary results of MAP servo control.
[Note: Following results are based on different subjects than the results used as the basis for FIGS. 17-19]

| Patient | Data Set | Pressure Range | # Beats | Error (mm Hg) |
|---|---|---|---|---|
| 1 | 1 | 69-106 | 653 | −1 ± 5 |
| 1 | 2 | 82-93 | 830 | −6 ± 6 |
| 2 | 1 | 73-83 | 747 | −1 ± 4 |
| 2 | 2 | 81-93 | 873 | −4 ± 6 |
| | | | TOTAL: 3,103 | MEAN: −3 ± 5 |

What is claimed is:

1. A method of positioning a blood pressure sensor including locating a blood vessel disposed within surrounding tissue, comprising:
    transmitting acoustic energy into said tissue including said blood vessel;
    evaluating reflections of said acoustic energy from said tissue and said blood vessel,
    identifying at least one region of reduced energy reflection within said tissue, said at least one region corresponding to said blood vessel,
    said act of identifying comprising automatically detecting a local minimum indicative of both lateral position and depth; and
    positioning said blood pressure sensor based at least in part on said act of identifying.

2. The method of claim 1, wherein said blood pressure sensor comprises a tonometric sensor, and said act of evaluating comprises analyzing at least one A-mode line.

3. The method of claim 2, further comprising correlating said at least one region to a depth location within said tissue based on said act of analyzing said at least one A-mode line.

4. The method of claim 2, wherein said act of identifying comprises:
forming at least one integrated power representation based on said reflections; and
identifying at least one artifact within said at least one integrated power representation, said at least one artifact corresponding to the lumen of said blood vessel.

5. The method of claim 4, wherein said act of identifying at least one artifact comprises identifying at least one plateau within a normalized integrated power profile.

6. The method of claim 1, wherein said act of identifying comprises:
measuring the signal level of said reflections as a function of depth within said tissue; and
identifying the lumen of said blood vessel based on at least one feature identified during said act of measuring.

7. The method of claim 1, wherein the act of identifying comprises:
determining a power metric from said reflections;
integrating said power metric to produce a power function;
normalizing said power function;
dividing said normalized power function into a plurality of intervals; and
evaluating at least one of said intervals to identify an artifact.

8. The method of claim 1, wherein said act of evaluating further comprises detecting an envelope associated with said reflections.

9. The method of claim 8, wherein said act of envelope detecting comprises:
providing an A-mode representation of said reflections;
multiplying at least a portion of said A-mode representation by a sine and a cosine function to produce a demodulated signal; and
lowpass filtering said demodulated signal.

10. The method of claim 9, wherein said act of lowpass filtering comprises filtering with a FIR filter, said FIR filter having a plurality of coefficients associated therewith.

11. The method of claim 9, further comprising applanating at least a portion of said tissue in order to reduce interference.

12. The method of claim 1, wherein said blood pressure sensor comprises a tonometric pressure sensor, and said act of transmitting comprises transmitting from an ultrasonic device, said pressure sensor and said ultrasonic device being substantially co-located.

13. A method of positioning a pressure transducer including locating a blood vessel in tissue, comprising:
generating at least one beam of acoustic waves;
transmitting said at least one beam of acoustic waves into said tissue, said beam moving with respect to said tissue so as to ensonify different portions of said tissue as a function of time;
receiving energy backscattered by said tissue and said blood vessel;
analyzing said backscattered energy to identify at least one plateau therein, said at least one plateau resulting from the lumen of said blood vessel;
correlating said at least one plateau to the location of said blood vessel; and
positioning said pressure transducer based at least in part on said location of said blood vessel.

14. Blood pressure sensor positioning apparatus, comprising:
a pressure sensor;
apparatus adapted to move said pressure sensor;
at least one transducer capable of transmitting an acoustic wave into tissue containing a blood vessel and receiving a plurality of echoes therefrom, said at least one transducer configured to generate first signals related to said echoes;
a processor, operatively connected to said at least one transducer, and configured to process said first signals to determine the location of the lumen of said blood vessel by comparing a region of reduced energy reflection within said tissue as compared with higher levels of energy reflection in surrounding tissue; and
a controller, operatively coupled to said apparatus adapted to move, said controller positioning said pressure sensor based at least in part on said location of the lumen;
wherein said transmitting an acoustic wave further comprises sweeping transversely across said tissue.

15. The apparatus of claim 14, wherein said processor is adapted to determine a power profile associated with said echoes, and identify at least one artifact therein, said at least one artifact corresponding at least in part to said lumen.

16. The apparatus of claim 15, wherein said power profile is integrated over a variable corresponding to the propagation of said acoustic wave, and said at least one artifact comprises a plateau within said integrated power profile.

17. The apparatus of claim 14, wherein said processor is adapted to determine a Doppler shift associated with blood present in said blood vessel.

18. The apparatus of claim 14, wherein said processor is adapted to compare the signal level of at least a portion of said echoes and identify at least one artifact therein.

19. The apparatus of claim 18, wherein said signal level comprises an envelope-squared metric, and said at least one artifact comprises a reduction in the magnitude of said envelope-squared metric, said reduction corresponding to said lumen of said blood vessel.

20. A method of positioning a blood pressure sensor including locating a blood vessel disposed within surrounding tissue, comprising the steps of:
transmitting acoustic energy into said tissue including said blood vessel to generate reflections thereof;
receiving said reflections of said acoustic energy from said tissue and said blood vessel;
forming at least one integrated power representation to identify at least one region of reduced energy reflection within said tissue, said at least one region corresponding to the lumen of said blood vessel;
locating said blood vessel based on the location of said lumen; and
positioning said sensor based at least in part on said act of locating.

21. Blood vessel locating apparatus, comprising:
at least one first transducer capable of transmitting an acoustic wave into a blood vessel and receiving a plurality of echoes therefrom, said first transducer configured to generate first signals related to said echoes;
at least one pressure transducer capable of obtaining a plurality of pressure signals from said blood vessel;
at least one signal converter, operatively coupled to said at least one first transducer and adapted to produce second signals from said first signals;
at least one digital processor, operatively coupled to an analog-to-digital converter, and configured to process said second signals; and a computer program running at least in part on said digital processor, said computer program being adapted to determine a power profile based on said second signals, and to determine the location of the lumen of said blood vessel based at least in part on one or more artifacts present within said power profile; said computer program further being adapted to measure pressure within said blood vessel based at least in part on said pressure signals.

22. A method of positioning a pressure sensor by locating a blood vessel disposed within surrounding tissue, comprising:
    transmitting acoustic energy into said tissue including said blood vessel;
    receiving reflections of said acoustic energy from said tissue and said blood vessel;
    basebanding at least a portion of said received reflections to produce baseband data;
    developing an envelope squared representation of said baseband data;
    applying a depth-dependent gain to at least a portion of said envelope squared representation;
    identifying said blood vessel based at least in part on an output of said act of applying; and
    positioning said sensor based at least in part on said act of identifying.

23. The method of claim 22, further comprising decimating at least a portion of said data or said envelope squared.

24. A method of locating at least one wall of a blood vessel, comprising:
    purposely compressing tissue surrounding at least a portion of said vessel so as to collapse interposed vessels;
    transmitting acoustic energy into the blood vessel;
    receiving reflected energy from said blood vessel;
    detecting at least one region associated with the lumen in said blood vessel from said reflected energy;
    starting at said at least one region, computing an integrated power in a first direction;
    evaluating said integrated power as a function of said direction; and
    detecting the location of said at least one wall of the blood vessel based at least in part on said act of evaluating.

25. The method of claim 24, wherein said received reflected energy is used to form A-mode signals, and said act of computing an integrated power comprises summing consecutive samples of a square of an envelope of said A-mode signals in said first direction.

26. A method of locating a first blood vessel disposed within surrounding tissue, comprising:
    applanating at least said tissue, said applanating comprising at least partly compressing one or more second blood vessels proximate to said first blood vessel;
    transmitting acoustic energy into said tissue including said first blood vessel;
    evaluating reflections of said acoustic energy from said tissue and said first blood vessel; and
    identifying at least one region of reduced energy reflection within said tissue as compared with higher levels of energy reflection in surrounding tissue, said at least one region corresponding to said first blood vessel.

27. The method of claim 26, wherein said act of at least partly compressing results in reducing interference with said act of identifying, said reducing of interference resulting at least in part from compression of said one or more second blood vessels.

28. A method of positioning a blood pressure sensor including locating a blood vessel disposed within surrounding tissue, comprising:
    a step for transmitting acoustic energy into said tissue including said blood vessel;
    a step for evaluating reflections of said acoustic energy from said tissue and said blood vessel;
    a step for identifying at least one region of reduced energy reflection within said tissue, said at least one region corresponding to said blood vessel, said step for identifying comprising at least a step for automatically detecting a local minimum indicative of both lateral position and depth; and
    a step for positioning said blood pressure sensor based at least in part on said step for detecting.

29. A method of positioning a pressure transducer including locating a blood vessel in tissue, comprising:
    generating acoustic waves;
    transmitting said acoustic waves into said tissue so as to ensonify different portions of said tissue as a function of time;
    receiving energy backscattered by said tissue and said blood vessel;
    analyzing said backscattered energy to identify at least one plateau therein, said at least one plateau resulting from the lumen of said blood vessel;
    correlating said at least one plateau to the a location of said blood vessel; and
    positioning said pressure transducer based at least in part on said location of said blood vessel.

30. A method of positioning a tonometric blood pressure sensor including locating a blood vessel disposed within surrounding tissue, comprising:
    transmitting acoustic energy into said tissue including said blood vessel to generate reflections thereof, and receiving said reflections of said acoustic energy from said tissue and said blood vessel;
    forming at least one integrated power representation using at least said reflections;
    identifying at least one region of reduced energy reflection within said tissue, said at least one region corresponding to the lumen of said blood vessel;
    locating said blood vessel based on the location of said lumen; and
    positioning said sensor based at least in part on said act of locating.

31. Blood vessel locating apparatus further adapted for measuring blood pressure, comprising:
    apparatus for transmitting an acoustic wave into a blood vessel and receiving a plurality of echoes therefrom;
    apparatus for generating first signals related to said echoes;
    apparatus for obtaining pressure signals from said blood vessel;
    apparatus for converting said first signals to second signals;
    apparatus for processing said second signals, said apparatus for processing being operatively coupled to said apparatus for converting; and
    apparatus for determining a power profile based on said second signals, and for determining the location of the lumen of said blood vessel based at least in part on one or more artifacts present within said power profile; said apparatus for determining further comprising apparatus for determining pressure within said blood vessel based at least in part on said pressure signals.

32. A method of positioning a blood pressure sensor by locating a blood vessel disposed within surrounding tissue, comprising:

a step for transmitting acoustic energy into said tissue including said blood vessel;
a step for receiving reflections of said acoustic energy from said tissue and said blood vessel;
a step for producing basebanded data from at least a portion of said received reflections;
a step for developing an envelope squared representation of said baseband data;

a step for applying a depth-dependent gain to at least a portion of said envelope squared representation;
a step for identifying said blood vessel based at least in part on an output of said step of applying; and
a step for positioning said blood pressure sensor above said identified blood vessel.

* * * * *